United States Patent
Rajendiran et al.

(10) Patent No.: US 9,951,098 B2
(45) Date of Patent: Apr. 24, 2018

(54) SYNTHESIS OF 5-AZACYTIDINE

(75) Inventors: Chinnapillai Rajendiran, Hyderabad (IN); Periyandi Nagarajan, Hyderabad (IN); Jasti Venkateswarlau, Hyderabad (IN)

(73) Assignee: Pharmion LLC, Summit, NJ (US)

( * ) Notice: Subject to any disclaimer, the term of this patent is extended or adjusted under 35 U.S.C. 154(b) by 706 days.

(21) Appl. No.: 14/007,955

(22) PCT Filed: Mar. 29, 2012

(86) PCT No.: PCT/US2012/031059
§ 371 (c)(1),
(2), (4) Date: Jan. 27, 2014

(87) PCT Pub. No.: WO2012/135405
PCT Pub. Date: Oct. 4, 2012

(65) Prior Publication Data
US 2014/0128593 A1    May 8, 2014

Related U.S. Application Data

(60) Provisional application No. 61/470,392, filed on Mar. 31, 2011.

(51) Int. Cl.
C07H 19/12 (2006.01)
C07H 1/00 (2006.01)
C07H 1/06 (2006.01)

(52) U.S. Cl.
CPC ............. C07H 19/12 (2013.01); C07H 1/00 (2013.01); C07H 1/06 (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 3,350,388 A | 10/1967 | Sorm et al. | |
| 3,817,980 A | 6/1974 | Vorbruggen et al. | |
| 3,891,623 A | 6/1975 | Vorbruggen et al. | |
| 4,082,911 A | 4/1978 | Vorbruggen | |
| 4,209,613 A | 6/1980 | Vorbruggen | |
| 6,642,206 B2 | 11/2003 | Ramasamy et al. | |
| 6,887,855 B2 | 5/2005 | Ionescu et al. | |
| 6,943,249 B2 | 9/2005 | Ionescu et al. | |
| 7,038,038 B2 | 5/2006 | Ionescu et al. | |
| 7,078,518 B2 | 7/2006 | Ionescu et al. | |
| 7,189,740 B2 | 3/2007 | Zeldis | |
| 7,192,781 B2 | 3/2007 | Luna et al. | |
| 7,642,247 B2 | 1/2010 | Daifuku et al. | |
| 7,700,770 B2 | 4/2010 | Ionescu et al. | |
| 7,759,481 B2 | 7/2010 | Gevenda et al. | |
| 7,772,199 B2 | 8/2010 | Ionescu et al. | |
| 7,858,774 B2 | 12/2010 | Ionescu et al. | |
| 8,058,424 B2 | 11/2011 | Ionescu et al. | |
| 8,211,862 B2 | 7/2012 | Ionescu et al. | |
| 8,212,021 B2 * | 7/2012 | Henschke ............. | C07H 13/04 536/28.3 |
| 8,513,406 B2 | 8/2013 | Ionescu et al. | |
| 8,614,313 B2 | 12/2013 | Ionescu et al. | |
| 2006/0063735 A1 | 3/2006 | Redkar et al. | |
| 2006/0069060 A1 | 3/2006 | Redkar et al. | |
| 2006/0074046 A1 | 4/2006 | Redkar et al. | |
| 2006/0247432 A1 | 11/2006 | Ionescu et al. | |
| 2007/0190022 A1 | 8/2007 | Bacopoulos et al. | |
| 2008/0057086 A1 | 3/2008 | Etter et al. | |
| 2009/0286752 A1 | 11/2009 | Etter et al. | |
| 2010/0035354 A1 | 2/2010 | Bigatti et al. | |
| 2010/0036112 A1 | 2/2010 | Henschke et al. | |
| 2010/0062992 A1 | 3/2010 | Redkar et al. | |
| 2010/0210833 A1 | 8/2010 | Jungmann et al. | |
| 2010/0292180 A1 | 11/2010 | Ionescu et al. | |
| 2010/0311683 A1 | 12/2010 | Beach et al. | |
| 2011/0042247 A1 | 2/2011 | Kocherlakota et al. | |
| 2011/0092694 A1 | 4/2011 | Ionescu et al. | |
| 2011/0201800 A1 | 8/2011 | Cherukupally et al. | |
| 2011/0245485 A1 | 10/2011 | De Ferra et al. | |
| 2012/0029181 A1 | 2/2012 | Ionescu et al. | |

FOREIGN PATENT DOCUMENTS

| | | |
|---|---|---|
| CZ | 114716 | 11/1964 |
| CZ | 116297 | 4/1965 |
| DE | 1922702 | 11/1969 |
| DE | 2012888 | 9/1971 |
| FR | 2123632 | 9/1972 |
| GB | 1227691 | 4/1971 |
| GB | 1227692 | 4/1971 |
| WO | 2004/082618 | 9/2004 |
| WO | 2004/082619 A2 | 9/2004 |
| WO | 2006/034154 A2 | 3/2006 |
| WO | 2008/088779 A2 | 7/2008 |
| WO | 2009/016617 | 2/2009 |

OTHER PUBLICATIONS

Toshima, K. et al., Chemical Reviews, "Recent Progress in O-Glycosylation Methods and Its Application to Natural Products Synthesis", 1993, vol. 93, pp. 1503-1531.*

(Continued)

*Primary Examiner* — Shaojia Anna Jiang
*Assistant Examiner* — Bahar Craigo
(74) *Attorney, Agent, or Firm* — Jones Day

(57) ABSTRACT

Provided herein are processes for the preparation of 5-azacytidine, useful for treating, preventing, and/or managing diseases or conditions including cancer, disorders related to abnormal cell proliferation, hematologic disorders, and myelodysplastic syndromes (MDS), wherein 5-azacytidine is represented by the structure:

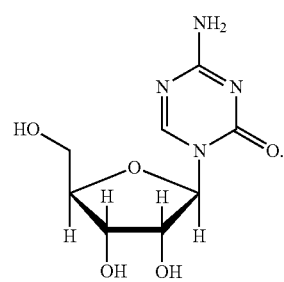

35 Claims, 20 Drawing Sheets

(56) References Cited

OTHER PUBLICATIONS

Turdi, S. et al., Toxicology Letters, "Amidization of Doxorubicin Alleviates Doxorubicin-Induced Contractile Dysfunction and Reduced Survival in Murine Cardiomyocytes", 2008, vol. 178, No. 3, pp. 197-201.*
Dintaman et al., "Inhibition of P-glycoprotein by D-α-tocopheral polyethylene glycol 1000 succinate (TPGS)," Pharm. Res., 16(10):1550-1556 (1999).
Dover et al., "5-azacytidine increases HbF production and reduces anemia in sickle cell disease: dose-response analysis of subcutaneous and oral dosage regimens," Blood, 66(3):527-532 (1985).
Gaubert et al., "Unnatural enantiomers of 5-azacytidine analogues: syntheses and enzymatic properties," Nucleosides, Nucleotides & Nucleic Acids, 20(4-7):837-840 (2001).
Gut et al., "Aza Analogs of Pyrimidine and Purine Bases of Nucleic Acids," in Advances in Heterocyclic Chemistry, vol. 1, Katritzky ed., pp. 189-251 (1963).
Hanka et al., "Microbiological production of 5-azacytidine. I. Production and biological activity," Antimicrobial Agents Chemother., 6:619-624 (1966).
ISA/EP International Search Report dated Sep. 21, 2004 for International Application No. PCT/US2004/007894, filed Mar. 16, 2004.
Lin et al., "High-performance liquid chromatographic analysis of chemical stability of 5-aza-2'-deoxycytidine," J. Pharm. Sci., 70(11):1228-1232 (1981).
Notice of Allowability in U.S. Appl. No. 10/390,526, dated Dec. 1, 2005.
Notice of Allowability in U.S. Appl. No. 10/390,530, dated May 13, 2005.
Notice of Allowability in U.S. Appl. No. 10/390,578, dated Dec. 29, 2004.
Notice of Allowability in U.S. Appl. No. 11/052,615, dated Mar. 9, 2006.
Notice of Allowability in U.S. Appl. No. 11/198,550, dated Feb. 24, 2009.
Notice of Allowability in U.S. Appl. No. 11/198,550, dated Jul. 31, 2009.
Notice of Allowability in U.S. Appl. No. 11/198,550, dated Dec. 2, 2009.
Notice of Allowability in U.S. Appl. No. 11/458,365, dated Jan. 26, 2010.
Notice of Allowability in U.S. Appl. No. 12/208,238, dated Aug. 26, 2010.
Notice of Allowability in U.S. Appl. No. 12/729,116, dated May 4, 2012.
Filing Receipt in U.S. Appl. No. 14/137,907, dated Jan. 9, 2014.
Notice of Allowability in U.S. Appl. No. 12/973,701, dated Jul. 5, 2010.
O'Neil et al. (eds.), The Merck Index, 13th Edition, Merck & Co., Inc., Whitehouse Station, NJ, p. 154-155 (2001).
O'Neil et al. (eds.), The Merck Index, 14th Edition, Merck & Co., Inc., Whitehouse Station, NJ, p. 150 (2006).
Office Action in U.S. Appl. No. 10/390,526, dated Dec. 3, 2003.
Office Action in U.S. Appl. No. 10/390,526, dated Oct. 21, 2004.
Office Action in U.S. Appl. No. 10/390,526, dated Apr. 6, 2005.
Office Action in U.S. Appl. No. 10/390,578, dated Jul. 1, 2004.
Office Action in U.S. Appl. No. 11/198,550, dated Aug. 1, 2007.
Office Action in U.S. Appl. No. 11/198,550, dated May 12, 2008.
Office Action in U.S. Appl. No. 11/198,550, dated Oct. 2, 2008.
Office Action in U.S. Appl. No. 11/381,275, dated Dec. 18, 2007.
Office Action in U.S. Appl. No. 11/381,275, dated Mar. 8, 2007.
Office Action in U.S. Appl. No. 11/458,365, dated Aug. 4, 2009.
Office Action in U.S. Appl. No. 11/458,365, dated Feb. 27, 2008.
Office Action in U.S. Appl. No. 11/458,365, dated Mar. 12, 2007.
Office Action in U.S. Appl. No. 11/458,365, dated Nov. 28, 2008.
Office Action in U.S. Appl. No. 12/208,238, dated May 12, 2010.
Office Action in U.S. Appl. No. 12/208,238, dated Nov. 13, 2009.
Office Action in U.S. Appl. No. 12/466,213, dated Aug. 1, 2011.
Office Action in U.S. Appl. No. 12/466,213, dated Feb. 28, 2012.
Office Action in U.S. Appl. No. 12/466,213, dated Aug. 29, 2013.
Office Action in U.S. Appl. No. 12/973,701, dated Mar. 11, 2011.
Piskala et al., "Direct synthesis of a 5-azapyrimidine ribonucleoside by the trimethylsilyl procedure," Nucleic Acid Chem., 1:435-41 (1978).
Piskala et al., "Direct synthesis of 5-azapyrimidine ribonucleosides," Nucleic Acids Research, Special Pub. No. 1: s17-20 (1975).
Seddon, "Pseudopolymorph: a polemic," Crystal Growth & Design, 4(6):1087 (2004).
Vippagunta et al., "Cyrstalline solids," Adv. Drug Deliv. Rev., 48(1):3-26 (2001).
Vorbruggen et al. In Organic Reactions, L.A. Paquette ed., John Wiley & Sons, New York, vol. 55, p. 100, (2000).
Vorbruggen et al., "Nucleoside synthesis with trimethylsilyl triflate and perchlorate as catalysts," Chem. Ber., 114: 1234-1255 (1981).
Vorbruggen et al., "A new simplified nucleoside synthesis," Chem. Ber., 114:1279-1286 (1981).
Winkley et al., "Direct glycosylation of 1,3,5-triazinones. A new approach to the synthesis of the nucleoside antibiotic 5-azacytidine (4-amino-1-β-D-ribofuranosyl-1,3,5-triazine-2-one) and related derivatives," J. Org. Chem., 35(2):491-95 (1970).
Wittenburg et al., "A new synthesis of nucleosides," Zeitschrift fur Chemie, 4:303-04 (1964).
Zaitseva et al., "Convergent synthesis and cytostatic properties of 2-chloro-2'-deoxy-2-;fluorodenosine and its N7-isomer," Bioorg. & Med. Chem. Lett., 5(24):2999-3002 (1995).
Notice of Allowability in U.S. Appl. No. 12/787,214, dated Oct. 24, 2013.
Office Action in U.S. Appl. No. 12/787,214, dated Jun. 5, 2013.
Office Action in U.S. Appl. No. 12/787,214, dated Mar. 6, 2012.
Office Action in U.S. Appl. No. 12/787,214, dated Sep. 23, 2011.
Aparicio et al., "Review of the clinical experience with 5-azacytidine and 5-aza-2'-deoxycytidine in solid tumors," Curr. Opin. Invest. Drugs, 3(4):627-633 (2002).
Asgharnejad, "Transport Processes in Pharmaceutical Systems," Amidon et al., ed., Marcell Dekker, pp. 185-218 (2000).
Balant et al., "Prodrugs for the improvement of drug absorption via different routes of administration," Eur. J. Drug Metab. Pharmacokinet., 15:143-153 (1990).
Balimane et al., "Involvement of multiple transporters in the oral absorption of nucleoside analogues," Adv. Drug Delivery Rev., 39:183-209 (1999).
Beisler, "Isolation, characterization, and properties of a labile hydrolysis product of the antitumor nucleoside, 5-azacytidine," J. Med. Chem., 21(2):204-208 (1978).
Bennett et al., "Proposed revised criteria for the classification of acute myeloid leukemia," Ann. Intern. Med., 103 (4):620-625 (1985).
Besa, "Myelodysplastic syndromes (refractory anemia). A perspective of the biologic, clinical, and therapeutic issues.," Med. Clin. North Am., 76(3):599-617 (1992).
Browne, "Fosphenytoin (cerebyx)," Clin. Neuropharmacol., 20:1-12 (1997).
Bundgaard, "Means to enhance penetration. Prodrugs as a means to improve the delivery of peptide drugs," Adv. Drug Delivery Rev., 8:1-38 (1992).
Bundgaard, "Bioreversible derivatization of drugs, principle and applicability to improve the therapeutic effects of drugs," Arch. Pharm. Chem., 86:1-39 (1979).
Bundgaard, "Improved drug delivery by the prodrug approach," Controlled Drug Delivery, 17:179-196 (1987).
Chan et al., "5-azacytidine hydrolysis kinetics measured by high-pressure liquid chromatography and 13C-NMR spectoscopy," J. Pharm. Sci., 68(7):807-812 (1979).
Farquhar et al., "Biologically reversible phosphate-protective groups," J. Pharm. Sci., 72:324-325 (1983).
Fenaux et al., "Efficacy of azacitidine compared with that of conventional care regimens in the treatment of higher-risk myelodysplastic syndromes: a randomised, open-label, phase III study," Lancet Oncol., 10(3):223-232 (2009).

(56) References Cited

OTHER PUBLICATIONS

Fleisher et al., "Improved oral drug delivery: solubility limitations overcome by the use of prodrugs," Adv. Drug Delivery Rev., 19:115-130 (1996).
Fleisher et al., "Design of prodrugs for improved gastrointestinal absorption by intestinal enzyme targeting," Methods Enzymol., 112:360-381 (1985).
Freeman et al., "Bioreversible protection for the phospho group: chemical stability and bioactivation of di(4-acetoxybenzyl) methylphosphonate with carboxyesterase," J. Chem. Soc. Chem. Commun., 875-877 (1991).
Friis et al., "Prodrugs of phosphates and phosphonates: Novel lipophilic α-acyloxyalkyl ester derivatives of phosphate- or phosphonate containing drugs masking the negative charges of these groups," Eur. J. Pharm. Sci., 4:49-59 (1996).
Wermuth et al., "Designing prodrugs and bioprecursors. I: carrier prodrugs," in the Practice of Medicinal Chemistry, Academic Press Limited, San Diego, CA, pp. 671-696 (1996).
Roche et al., Des. Biopharm. Prop. Prodrugs Analogs, American Pharmaceutical Association, Washington, D.C., pp. 409-421 (1977).
Harper, "Drug Latentiation," Progress in Drug Research, 4:221-294 (1962).
Kornblith et al., "Impact of azacytidine on the quality of life of patients with myelodysplastic syndrome treated in a randomized phase III trial: a cancer and leukemia group B study," J. Clin. Oncol., 20(10):2441-2452 (2002).
List et al., "The myelodysplastic syndromes: biology and implications for management," J. Clin. Oncol., 8:1424-1441 (1990).
Mizen et a., "The use of esters as prodrugs for oral delivery of β-lactam antibiotics," Pharm. Biotech., 11:345-365 (1998).
Nathwani et al., "Penicillins. A Current review of their clinical pharmacology and therapeutic use," Drugs, 45:866-894 (1993).
Niedballa et al., "A general synthesis of n-glycosides, V. synthesis of 5-azacytidines," J. Org. Chem., 39 (25):3672-3674 (1974).
Notari et al., "Kinetics and mechanisms of degradation of the antileukemic agent 5-azacytidine in aqueous solutions," Pharm. Sci., 64(7):1148-1157 (1975).
Pauletti et al., "Improvement of oral peptide bioavailability: peptidomimetics and prodrug strategies," Adv. Drug. Delivery Rev., 27:235-256 (1997).
Piskala et al., "Nucleic acids components and their analogues. Synthesis of 1-glycosyl derivatives of 5-azauracil and 5-azacytosine," Collect. Czech. Chem. Commun., 29:2060-2076 (1964).
Silverman et al., "Response rates using international working group (IWG) criteria in patients with myelodyplastic syndromes (MDS) treated with azacitidine," Blood 106(11):Abstract 2526 (2005).

Silverman et al., "Randomized controlled trial of azacitidine in patients with the myelodysplastic syndrome: a study of the cancer and leukemia group B," J. Clin. Oncol., 20(10):2429-2440 (2002).
Sinhababu et al., "Prodrugs of anticancer agents," Adv. Drug Delivery Rev., 19:241-273 (1996).
Stella et al., "Prodrugs. Do they have advantages in clinical practice," Drugs, 29:455-473 (1985).
Tan et al., "Development and optimization of anti-HIV nucleoside analogs and prodrugs: a review of their cellular pharmacology, structure-activity relationships and pharmacokinetics," Adv. Drug Delivery Rev., 39:117-151 (1999).
Taylor, "Improved passive oral drug delivery via prodrugs," Adv. Drug Delivery Rev., 19:131-148 (1996).
The Merck Manual, 17th Edition, Merck & Company, West Point, PA, pp. 953-954 (1999).
Gangwar, "Prodrug strategies to enhance the intestinal absorption of peptides," Drug Discovery Today, 2:148-155 (1997).
Vujjini et al., "An improved and scalable process for the synthesis of 5-azacytidine: an antineoplastic drug," Org. Process Res. Dev., 17:303-306 (2013).
Waller et al., "Prodrugs," Br. J. Clin. Pharmac., 28:497-507 (1989).
Wang et al., "Prodrug approaches to the improved delivery of peptide drugs," Curr. Pharm. Design., 5:265-287 (1999).
Wiebe, "Concepts for the design of anti-HIV nucleoside prodrugs for treating cephalic HIV infection," Adv. Drug Delivery Rev., 39:63-80 (1999).
ISA/EP International Search Report dated Jul. 27, 2012, for International Application No. PCT/US2012/031059, filed Mar. 29, 2012.
ISA/EP Written Opinion dated Jul. 27, 2012, for International Application No. PCT/US2012/031059, filed Mar. 29, 2012.
Ault, Techniques and Experiments for Organic Chemistry, 6th ed., University Science Books, 59-60 (1998).
Beers et al. (eds.), Chapter 142, Section 11, in the Merck Manual of Diagnosis and Therapy, 18th Edition, pp. 1114-1116 (2006).
Beisler et al., "Chemistry of antitumor triazine nucleosides, an improved synthesis of dihydro-5-azacytidine," J. Carbohydrates Nucleosides Nucleotides, 4(5): 281-299 (1977).
Beisler et al., "Synthesis and antitumor activity of dihydro-5-azacytidine, a hydrolytically stable analogue of 5-azacytidine," J. Med. Chem., 20(6): 806-812 (1977).
Bergy et al., "Microbiological production of 5-azacytidine. II. Isolation and chemical structure," Antimicrob. Agents Chemother. ,6:625-630 (1966).
Cabri et al., "Polymorphisms and patent, market, and legal battles: Cefdinir case study," Organic Process Res. Dev., 11:64-72 (2007).
Dean, Analytical Chemistry Handbook, McGraw-Hill, Inc., pp. 10.23-10.26 (1995).

* cited by examiner

SYNTHESIS OF 5-AZACYTIDINE

This application is a 371 of International Application No. PCT/US2012/031059, filed Mar. 29, 2012, which claims priority to U.S. provisional application No. 61/470,392, filed Mar. 31, 2011, each of which is hereby incorporated by reference in its entirety.

I. FIELD

Provided herein are processes for the preparation of 5-azacytidine (also known as azacitidine). 5-Azacytidine is useful for treating, preventing, and/or managing diseases or conditions, including cancer, disorders related to abnormal cell proliferation, hematologic disorders, and myelodysplastic syndromes (MDS), among others.

II. BACKGROUND

Cancer is a major public health problem worldwide. In the United States alone, approximately 560,000 people died of cancer in 2006. See, e.g., U.S. Mortality Data 2006, National Center for Health Statistics, Centers for Disease Control and Prevention (2009). Many types of cancer have been described in the medical literature. Examples include cancer of the blood, bone, skin, lung, colon, breast, prostate, ovary, brain, kidney, bladder, pancreas, and liver. The incidence of cancer continues to climb as the general population ages and as new forms of cancer develop. A continuing need exists for effective therapies to treat subjects with cancer.

Myelodysplastic syndromes (MDS) are a diverse group of hematopoietic cell disorders. MDS affect approximately 40,000-50,000 people in the U.S. and 75,000-85,000 people in Europe. MDS may be characterized by a cellular marrow with impaired morphology and maturation (dysmyelopoiesis), peripheral blood cytopenias, and a variable risk of progression to acute leukemia, resulting from ineffective blood cell production. See, e.g., The Merck Manual 953 (17th ed. 1999); List et al., J. Clin. Oncol. 8:1424 (1990).

MDS are grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS may develop complications related to anemia, neutropenia (infections), and/or thrombocytopenia (bleeding). From about 10% to about 70% of patients with MDS may develop acute leukemia. In the early stages of MDS, the main cause of cytopenias is increased programmed cell death (apoptosis). As the disease progresses and converts into leukemia, a proliferation of leukemic cells overwhelms the healthy marrow. The disease course differs, with some cases behaving as an indolent disease and others behaving aggressively with a very short clinical course that converts into an acute form of leukemia. The majority of people with higher risk MDS eventually experience bone marrow failure. Up to 50% of MDS patients succumb to complications, such as infection or bleeding, before progressing to AML.

Primary and secondary MDS are defined by taking into account patients' prior history: previous treatments with chemotherapy, radiotherapy or professional exposure to toxic substances are factors delineating secondary MDS (sMDS) from primary MDS. Cytogenetically, one difference between the two groups is the complexity of abnormal karyotypes; single chromosome aberrations are typical for primary MDS, while multiple changes are more frequently seen in secondary disorders. Some drugs may have specific targets such as hydroxyurea for 17p and topoisomerases inhibitors for 11q23 and 21q22. The genetic changes in the malignant cells of MDS result mainly in the loss of genetic material, including probable tumor suppressor genes.

An international group of hematologists, the French-American-British (FAB) Cooperative Group, classified MDS into five subgroups, differentiating them from acute myeloid leukemia. See, e.g., The Merck Manual 954 (17th ed. 1999); Bennett J. M., et al., Ann. Intern. Med., 103(4): 620-25 (1985); and Besa E. C., Med. Clin. North Am. 76(3): 599-617 (1992). An underlying trilineage dysplastic change in the bone marrow cells of the patients is found in all subtypes. Information is available regarding the pathobiology of MDS, certain MDS classification systems, and particular methods of treating and managing MDS. See, e.g., U.S. Pat. No. 7,189,740 (issued Mar. 13, 2007), which is incorporated by reference herein in its entirety.

Nucleoside analogs have been used clinically for the treatment of viral infections and cancer. Most nucleoside analogs are classified as anti-metabolites. After they enter the cell, nucleoside analogs are successively phosphorylated to nucleoside 5'-mono-phosphates, di-phosphates, and tri-phosphates.

5-Azacytidine (National Service Center designation NSC-102816; CAS Registry Number 320-67-2), also known as azacitidine, AZA, 4-amino-1-(3,4-dihydroxy-5-hydroxymethyl-tetrahydrofuran-2-yl)-1H-[1,3,5]triazin-2-one, 4-amino-1-β-D-ribofuranosyl-1,3,5-triazin-2(1H)-one, or 4-amino-1-β-D-ribofuranosyl-S-triazin-2(1H)-one, is currently marketed as the drug product VIDAZA®. 5-Azacytidine is a nucleoside analog, more specifically a cytidine analog. 5-Azacytidine is an antagonist of its related natural nucleoside, cytidine. 5-Azacytidine is also an antagonist of deoxycytidine. A structural difference between 5-azacytidine and cytidine is the presence of a nitrogen at position 5 of the cytosine ring in place of a carbon. 5-Azacytidine may be defined as having the molecular formula $C_8H_{12}N_4O_5$, a molecular weight of about 244.2 grams per mole, and the following structure:

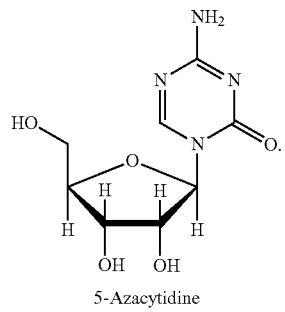

5-Azacytidine

After its incorporation into replicating DNA, 5-azacytidine forms a covalent complex with DNA methyltransferases. DNA methyltransferases are responsible for de novo DNA methylation and for reproducing established methylation patterns in daughter DNA strands of replicating DNA. Inhibition of DNA methyltransferases by 5-azacytidine leads to DNA hypomethylation, thereby restoring normal functions to morphologically dysplastic, immature hematopoietic cells and cancer cells by re-expression of genes involved in normal cell cycle regulation, differentiation and death. The cytotoxic effects of 5-azacytidine cause the death of rapidly dividing cells, including cancer cells, that are no longer responsive to normal cell growth control mechanisms. 5-Azacytidine also incorporates into RNA. The cytotoxic effects of 5-azacytidine may result from multiple mechanisms, including inhibition of DNA, RNA and protein synthesis, incorporation into RNA and DNA, and activation of DNA damage pathways.

5-Azacytidine has been tested in clinical trials and showed significant anti-tumor activity, such as, for example, in the treatment of myelodysplastic syndromes (MDS). See, e.g., Aparicio et al., *Curr. Opin. Invest. Drugs* 3(4): 627-33 (2002). 5-Azacytidine has undergone NCI-sponsored trials for the treatment of MDS and has been approved for treating all FAB subtypes of MDS. See, e.g., Kornblith et al., *J. Clin. Oncol.* 20(10): 2441-52 (2002); Silverman et al., *J. Clin. Oncol.* 20(10): 2429-40 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., *Lancet Oncol.*, 2009, 10(3):223-32; Silverman et al., *Blood* 106(11): Abstract 2526 (2005).

5-Azacytidine has been difficult to synthesize, particularly for manufacturing at large commercial scales, in part because of its instability in water. For example, the s-triazine ring of 5-azacytidine is prone to degradation in water. In aqueous solutions at neutral pH, hydration of the 5,6-imine double bond occurs rapidly, followed by bond cleavage to yield the formyl derivative, N-(formylamidino)-N'-β-D-ribofuranosylurea, which deformylates to give 1-β-D-ribofuranosyl-3-guanylurea irreversibly. See, e.g., J. A. Beisler, *J. Med. Chem.*, 1978, 21(2):204-08; K. K. Chan et al., *J. Pharm. Sci.* 1979, 68(7):807-12. In addition, the hydrolytic degradation of 5-azacytidine was studied as a function of pH, temperature, and buffer concentration. See, e.g., R. E. Notari et al., *Pharm. Sci.* 1975, 64(7):1148-57. At pH 1, the main degradation products were 5-azacytosine and 5-azauracil from the hydrolysis of 5-azacytidine. The instability of 5-azacytidine in water presents a challenge for the isolation and purification of 5-azacytidine from a solvent system that contains water, such as solvent systems used during the work-up stage of a reaction.

5-Azacytidine was first prepared via a multi-step synthesis starting from peracetylated 1-glycosylisocyanate. See Piskala et al., *Collect. Czech. Chem. Commun.*, 1964, 29:2060-76. This method involves a reactive starting material (isocyanate) with a controlled stereochemistry (1-β configuration), which is not suitable for the production of large scale batches of 5-azacytidine. Many other existing methods for preparing 5-azacytidine involve steps that are difficult to scale-up, or involve the use of expensive reagents. Other methods do not describe purification steps necessary to produce Active Pharmaceutical Ingredient (API) that meets the purity standards for human use, or give poor overall yields of the purified 5-azacytidine product.

U.S. Pat. No. 7,038,038, issued May 2, 2006, which is incorporated herein by reference in its entirety, describes a process for preparing 5-azacytidine, comprising, inter alia, the steps of coupling a silylated 5-azacytosine with a protected β-D-ribofuranose in the presence of a non-metallic Lewis acid, such as trimethylsilyl trifluoromethanesulfonate (TMS-triflate), and deprotecting the product to give 5-azacytidine.

Metallic Lewis acids, such as stannic chloride, are generally less expensive and more readily available than non-metallic Lewis acids, such as TMS-triflate. However, the use of metal-based reagents in the synthesis of API intended for human use generally requires appropriate purification steps to remove metal-based impurities in order to consistently control the levels of residual metals in the final API. For the production of a drug substance intended for use in humans, current Good Manufacturing Practices (cGMP) are applicable. Procedures need to be in place that can control the levels of impurities and ensure that API batches are produced which consistently meet their predetermined specifications. For example, in a GMP environment, it is not acceptable to have one batch having a heavy metal content that is within a desired specification, and then have a batch run under similar circumstances having heavy metal impurities well over the desired specification.

A great need remains for a process to prepare pure 5-azacytidine suitable for human use, particularly on a commercial scale, that is, inter alia, safe, scalable, efficient, economically viable, and/or having other potential advantages.

Citation of any references in this Section of the application is not to be construed as an admission that such reference is prior art to the present application.

III. SUMMARY

Provided herein are, inter alia, safe, efficient, cost effective, and/or readily scaleable processes useful for the production of 5-azacytidine, or a salt, solvate, hydrate, or polymorph thereof. In one embodiment, provided herein are processes useful for the production of 5-azacytidine, or a salt, solvate, hydrate, or polymorph thereof, that is substantially pure. In one embodiment, provided herein are processes useful for the production of 5-azacytidine, or a salt, solvate, hydrate, or polymorph thereof, that is substantially chemically pure. In one embodiment, provided herein are processes useful for the production of 5-azacytidine, or a salt, solvate, hydrate, or polymorph thereof, that is substantially physically pure. In one embodiment, provided herein are processes useful for the production of 5-azacytidine, or a salt, solvate, hydrate, or polymorph thereof, suitable for use in humans.

In one embodiment, provided herein are processes for preparing 5-azacytidine, or a salt, solvate, hydrate, or polymorph thereof, comprising the steps of reacting a silylated 5-azacytosine with a protected β-D-ribofuranose in the presence of a metallic Lewis acid to yield a protected 5-azacytidine, deprotecting the protected 5-azacytidine to yield 5-azacytidine, and purifying the 5-azacytidine to yield 5-azacytidine, or a salt, solvate, hydrate, or polymorph thereof, that is substantially free of one or more impurities, including but not limited to, a metal-based impurity.

In one embodiment, provided herein is a salt of 5-azacytidine, including, but not limited to, hydrochloric acid salt, sulfuric acid salt, hydrobromic acid salt, and methanesulfonic acid salt. In one embodiment, provided herein is 5-azacytidine hydrochloric acid salt. In one embodiment, provided herein is a salt of 5-azacytidine that is substantially free of one or more impurities, such as for example, a metal-based impurity. In one embodiment, provided herein is a pharmaceutically acceptable salt of 5-azacytidine, including, but not limited to hydrochloric acid salt, sulfuric acid salt, hydrobromic acid salt, and methanesulfonic acid salt. In one embodiment, provided herein is a pharmaceutically acceptable salt of 5-azacytidine that is substantially free of one or more impurities, such as for example, a metal-based impurity.

In specific embodiments, provided herein are processes for preparing 5-azacytidine, or a salt, solvate, hydrate, or polymorph thereof, comprising any one, two, three, four, five, or six of the steps of:

(a) reacting 5-azacytosine with a silylating reagent to yield a silylated 5-azacytosine;
(b) reacting the silylated 5-azacytosine with an acyl protected β-D-ribofuranose in the presence of a metallic Lewis acid; and quenching the reaction with water and at least one neutralizing reagent to yield a protected 5-azacytidine;
(c) reacting the protected 5-azacytidine with a base, selected from the group consisting of alkoxide, ammonia, and tetra-substituted ammonium hydroxide, in an alcohol to yield 5-azacytidine;
(d) contacting the 5-azacytidine from step (c) with an acid in an organic solvent to yield a salt of 5-azacytidine;
(e) contacting the salt of 5-azacytidine from step (d) with a base in an organic solvent to yield 5-azacytidine as a free base; and
(f) re-crystallizing the 5-azacytidine from step (e).

In one embodiment, the silylated 5-azacytosine is a compound of formula (A):

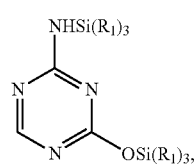

(A)

wherein each $R_1$ is independently optionally substituted $C_1$-$C_{10}$ alkyl, optionally substituted $C_3$-$C_{10}$ cycloalkyl, or optionally substituted $C_6$-$C_{10}$ aryl. In some embodiments, $R_1$ is straight chain alkyl, branched alkyl, cycloalkyl, or aryl, including but not limited to, methyl, ethyl, i-propyl, t-butyl, phenyl, xylyl, and benzyl. In some embodiments, $R_1$ is methyl.

In one embodiment, the silylating reagent used in step (a) is a trimethylsilyl (TMS) reagent, including but not limited to, hexamethyldisilazane (HMDS) and chlorotrimethylsilane (TMSCl).

In one embodiment, the silylation reaction of step (a) is carried out in the presence of ammonium sulfate. In one embodiment, the silylation reaction of step (a) is carried out at elevated temperature. In one embodiment, the silylation reaction of step (a) is carried out under an inert atmosphere. In some embodiments, the silylated 5-azacytosine is isolated as a solid. In other embodiments, the silylated 5-azacytosine is used directly in step (b) without isolation.

In one embodiment, the acyl protected β-D-ribofuranose is a compound of formula (B):

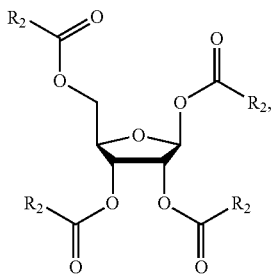

(B)

wherein each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl. In some embodiments, $R_2$ is optionally substituted methyl or optionally substituted phenyl. In some embodiments, $R_2$ is methyl. In some embodiments, $R_2$ is phenyl. In some embodiments, the acyl protected β-D-ribofuranose is:

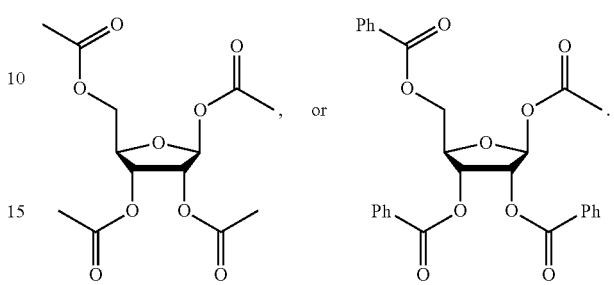

In one embodiment, the metallic Lewis acid is stannic chloride or ferric chloride. In one embodiment, the metallic Lewis acid is stannic chloride. In one embodiment, the metallic Lewis acid is ferric chloride.

In one embodiment, the protected 5-azacytidine is a compound of formula (C):

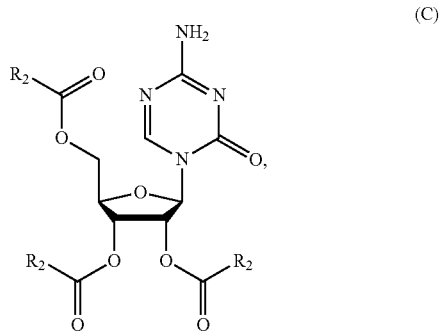

(C)

wherein each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl. In some embodiments, $R_2$ is optionally substituted methyl or optionally substituted phenyl. In some embodiments, $R_2$ is methyl. In some embodiments, $R_2$ is phenyl. In some embodiments, the protected 5-azacytidine is:

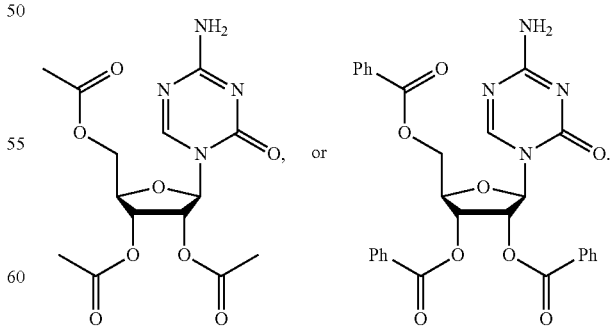

In one embodiment, the reaction of step (b) is carried out in a solvent with low water solubility. In some embodiments, the reaction of step (b) is carried out in dichloromethane. In one embodiment, the reaction of step (b) is carried out at a temperature of less than about 10° C. In one embodiment, the reaction of step (b) is carried out at a temperature of less than about 5° C. In one embodiment, the reaction of step (b) is carried out at a temperature of greater than about −20° C. In one embodiment, the reaction of step (b) is carried out at a temperature of greater than about −10° C. In one embodiment, the reaction of step (b) is carried out at a temperature of greater than about 0° C. In one embodiment, the reaction of step (b) is carried out at a temperature of between about 0° C. and about 5° C.

In one embodiment, the neutralizing reagent in step (b) is an inorganic reagent. In one embodiment, the neutralizing reagent in step (b) is an inorganic base. In one embodiment, the neutralizing reagent in step (b) is an inorganic salt. In one embodiment, the neutralizing reagent in step (b) is a carbonate or bicarbonate salt, or a mixture thereof. In one embodiment, the neutralizing reagent in step (b) is sodium bicarbonate. In one embodiment, the neutralizing reagent in step (b) is sodium carbonate.

In one embodiment, the reaction of step (b) is quenched with water and one or more neutralizing reagents(s) to yield a quenched composition. In one embodiment, the reaction of step (b) is quenched at a temperature of less than about 10° C. In one embodiment, the quenched composition of the reaction of step (b) is filtered. In one embodiment, the quenching composition of the reaction of step (b) is filtered at a temperature of less than about 10° C. In one embodiment, the filtrate of the quenched composition of the reaction of step (b) is washed with an aqueous EDTA (ethylenediaminetetraacetic acid) salt solution. In one embodiment, the filtrate of the quenched composition of the reaction of step (b) is washed with an aqueous EDTA disodium salt solution.

In one embodiment, the base in step (c) is an alkoxide. In one embodiment, the base in step (c) is a sodium alkoxide. In one embodiment, the base in step (c) is sodium methoxide. In one embodiment, the alcohol in step (c) is methanol. In one embodiment, the 5-azacytidine from step (c) is collected by filtration. In one embodiment, the 5-azacytidine from step (c) is washed with a non-aqueous solvent, including but not limited to, an alcohol, such as methanol.

In one embodiment, the acid in step (d) is an organic or an inorganic acid, including, but not limited to, hydrochloric acid, hydrobromic acid, sulfuric acid, and methanesulfonic acid. In some embodiments, the acid used in step (d) is hydrochloric acid. In one embodiment, the organic solvent in step (d) is an alcohol. In some embodiments, the organic solvent in step (d) is methanol. In some embodiments, the organic solvent in step (d) is isopropanol.

In one embodiment, the salt of 5-azacytidine from step (d) is collected by filtration. In one embodiment, the salt of 5-azacytidine from step (d) is washed with an organic solvent, including but not limited to, an alcohol, such as methanol.

In one embodiment, the base in step (e) is an organic base, including but not limited to, triethylamine, diisopropylethyl amine, pyridine, diisopropylamine, 2,6-lutidine, N-methylmorpholine, and N,N-dicyclohexylmethyl amine. In some embodiments, the base in step (e) is triethylamine. In one embodiment, the organic solvent in step (e) is an alcohol. In some embodiments, the organic solvent in step (e) is methanol. In one embodiment, the free base of 5-azacytidine from step (e) is collected by filtration. In one embodiment, the free base of 5-azacytidine from step (e) is washed with an organic solvent, including but not limited to, an alcohol, such as methanol. In one embodiment, the free base of 5-azacytidine from step (e) is substantially free of one or more impurities, including but not limited to, a metal-based impurity and an acidic salt counter ion, such as for example, chloride.

In one embodiment, step (f) comprises the steps of:
(1) dissolving 5-azacytidine free base from step (e) in dimethylsulfoxide (DMSO) at a temperature sufficient to allow the 5-azacytidine to dissolve; and optionally filtering the solution to remove insoluble particles;
(2) adding an anti-solvent to the solution of step (1); and
(3) cooling the mixture of step (2) wherein 5-azacytidine re-crystallizes.

In one embodiment, the optional filtration in step (f)(1) is carried out at an elevated temperature, such as for example, a temperature greater than about 85° C. In one embodiment, the anti-solvent of step (f)(2) is an alcohol. In one embodiment, the anti-solvent of step (f)(2) is methanol.

In one embodiment, step (f) further comprises the steps of:
(4) collecting the re-crystallized 5-azacytidine from step (3) by filtration; and
(5) drying the 5-azacytidine from step (4) under vacuum.

In one embodiment, provided herein are processes for preparing 5-azacytidine, or a pharmaceutically acceptable salt, solvate, hydrate, or polymorph thereof, for treating, preventing, and/or managing diseases or conditions including cancer, disorders related to abnormal cell proliferation, hematologic disorders, and myelodysplastic syndromes (MDS), among others.

IV. BRIEF DESCRIPTION OF THE FIGURES

V. DETAILED DESCRIPTION

Figure 1:
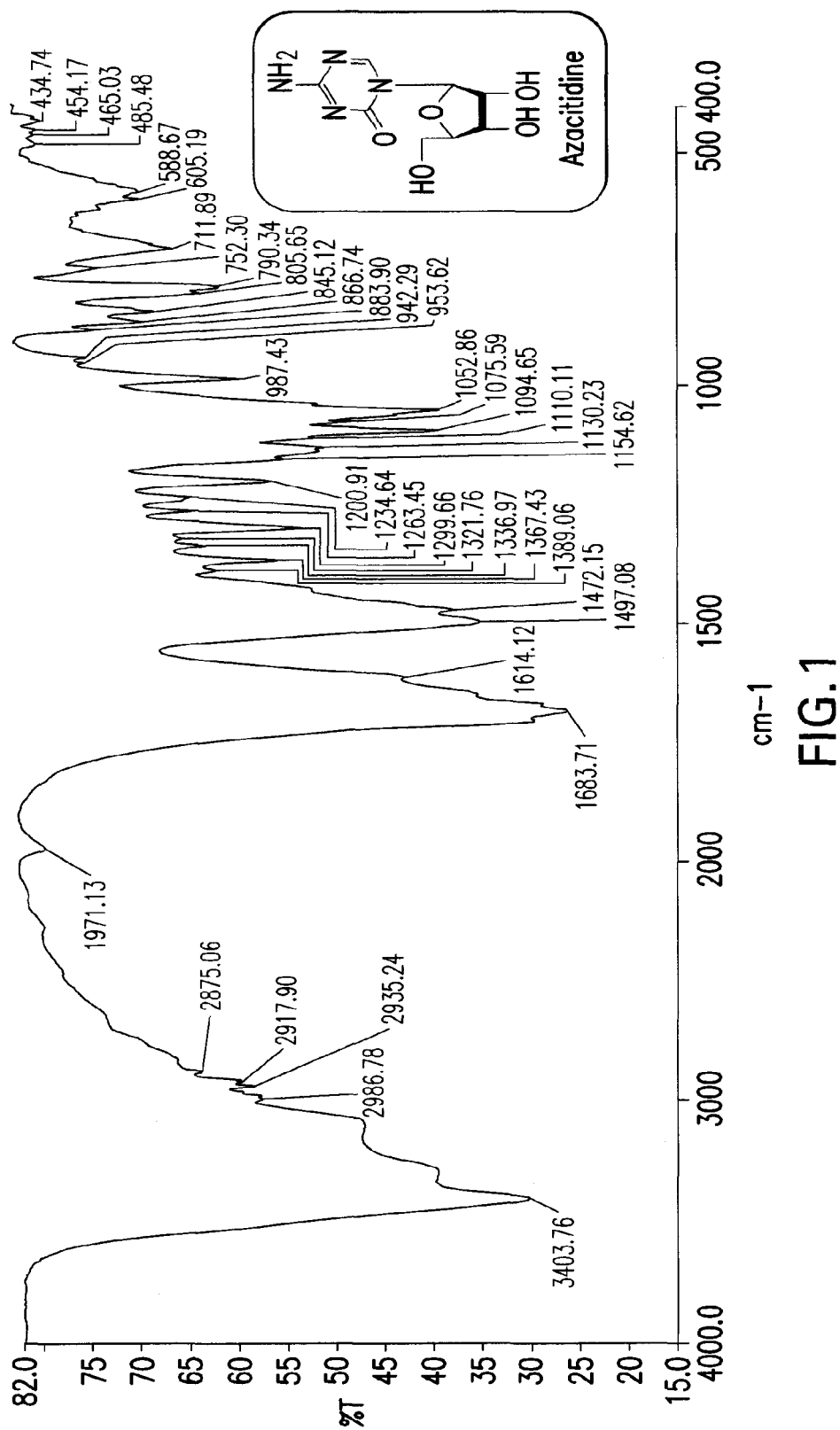
FIG. 1 represents an Infrared (IR) spectrum of 5-azacytidine.

Unless defined otherwise, all technical and scientific terms used herein have the same meaning as those commonly understood by one of ordinary skill in the art. All publications and patents referred to herein are incorporated by reference herein in their entireties.

A. Definitions

As used herein, and unless otherwise specified, the term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, i-propyl, butyl (including all isomeric forms), n-butyl, i-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

As used herein, and unless otherwise specified, the term "cycloalkyl" refers to a cyclic saturated bridged and/or non-bridged monovalent hydrocarbon radical, which may be optionally substituted one or more substituents as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

As used herein, and unless otherwise specified, the term "aryl" refers to a monocyclic aromatic group and/or multi-cyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

As used herein, and unless otherwise specified, the term "halo," "halogen," or "halide" refers to fluorine, chlorine, bromine, and/or iodine.

As used herein, and unless otherwise specified, the term "hydrogen" encompasses proton ($^1H$), deuterium ($^2H$), tritium ($^3H$), and/or mixtures thereof.

As used herein, and unless otherwise specified, the term "optionally substituted" is intended to mean that a group, such as an alkyl, alkenyl, alkynyl, cycloalkyl, aryl, aralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more (in specific embodiments, one, two, three, or four) substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more (in specific embodiments, one, two, three, or four) substituents $Q^1$; or (iii) R$^b$ and R$^c$ together with the N atom to which they are attached form heteroaryl or heterocyclyl, optionally substituted with one or more (in specific embodiments, one, two, three, or four) substituents $Q^1$. As used herein, all groups that can be substituted are "optionally substituted," unless otherwise specified.

In specific embodiments, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "alkenyl" refers to a linear or branched monovalent hydrocarbon radical, which contains one or more (in specific embodiments, one to five) carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more (in specific embodiments, one to five) carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the term "arylalkyl" or "aralkyl" refers to a monovalent alkyl group substituted with aryl. In certain embodiments, both alkyl and aryl may be optionally substituted with one or more substituents.

As used herein, and unless otherwise specified, the term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzopyranyl, benzimidazolyl, benzoisoxazolyl, benzopyranyl, benzothiadiazolyl, benzothiazolyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl groups may be optionally substituted with one or more substituents.

As used herein, and unless otherwise specified, the term "heterocycloalkyl," "heterocyclyl," or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may be optionally substituted with one or more substituents.

As used herein, and unless otherwise specified, the term "methylene" refers to a divalent —$CH_2$— group.

As used herein, and unless otherwise specified, the term "carbonyl" refers to a divalent —C(=O)— group.

As used herein, and unless otherwise specified, the term "heteroalkyl" or "heteroalkyl group" refers to a univalent group derived from an alkyl group, where at least one methylene group is replaced by a heteroatom or a heterogroup such as O, S, or NR, where R is H or an organic group.

As used herein, and unless otherwise specified, the term "organic group" refers to a group containing at least one carbon atom. Examples of the organic group include, but are not limited to, alkyl, alkenyl, alkynyl, carboxyl, acyl, cycloalkyl, aryl, heteroaryl, heteroalkyl, and heterocycloalkyl.

As used herein, and unless otherwise specified, the term "alkoxy" or "alkoxy group" refers to an alkyl group that is linked to another group via an oxygen atom (i.e., —O-alkyl). An alkoxy group can be unsubstituted or substituted with one or more suitable substituents. Examples of alkoxy groups include, but are not limited to, ($C_1$-$C_6$)alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, —O-3-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl, and —O-hexyl. An alkoxy group can be unsubstituted or substituted with one or two suitable substituents. In some embodiments, the alkyl chain of an alkyloxy group is straight or branched, and has from 1 to 8 carbon atoms, referred to herein as "($C_1$-$C_8$)alkoxy".

As used herein, and unless otherwise specified, the term "aryloxy" or "aryloxy group" refers to an O-aryl group, wherein aryl is as defined herein elsewhere. An aryloxy group can be unsubstituted or substituted with one or two suitable substituents. In some embodiments, the aryl ring of an aryloxy group is a monocyclic ring, wherein the ring comprises 6 carbon atoms, referred to herein as "($C_6$) aryloxy."

As used herein, and unless otherwise specified, the term "alkoxycarbonyl" or "alkoxycarbonyl group" refers to a monovalent group of the formula —C(=O)-alkoxy. In some embodiments, the hydrocarbon chain of an alkoxycarbonyl group is straight or branched, and has from 1 to 8 carbon atoms, referred to herein as a "lower alkoxycarbonyl" group.

As used herein, and unless otherwise specified, the term "alkylsulfanyl" or "alkylsulfanyl group" refers to a monovalent group of the formula —S-alkyl. In some embodiments, the hydrocarbon chain of an alkylsulfanyl group is straight or branched, and has from 1 to 8 carbon atoms, referred to herein as a "lower alkylsulfanyl" group.

As used herein, and unless otherwise specified, the term "acyloxy" or "acyloxy group" refers to a monovalent group of the formula —O—C(=O)-alkyl or —O—C(=O)-aryl, wherein alkyl and aryl are as defined herein elsewhere.

As used herein, and unless otherwise specified, the term "acyl" or "acyl group" refers to a monovalent group of the formula —C(=O)H, —C(=O)-alkyl, or —C(=O)-aryl, wherein alkyl and aryl are as defined herein elsewhere.

When a compound provided herein contains one or more acidic or basic moieties, the compound may exist as a salt. As used herein, and unless otherwise specified, the term "salt" or "salts" of a compound refers to salt(s) of a compound having basic or acidic groups, and the salts are prepared from the compound and one or more acids, including inorganic acids and organic acids; or one or more bases, including inorganic bases and organic bases. In certain embodiments, the compounds provided herein are basic in nature and are capable of forming a wide variety of salts with various inorganic or organic acids. The acids that may be used to prepare salts of such basic compounds are described herein elsewhere. In certain embodiments, the compounds provided herein are acidic in nature and are capable of forming a wide variety of salts with various inorganic or organic bases. Non-limiting examples of such salts with inorganic bases include alkali metal or alkaline earth metal salts. In certain embodiments, the salt of a compound provided herein comprises one or more acidic or basic counter-ions, including, but not limited to: acetate, ascorbate, benzenesulfonate, benzoate, bicarbonate, bitartrate, bromide, calcium edetate, camsylate, carbonate, chloride, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, malonate, mandelate, mesylate, methanesulfonate, muscate, napsylate, nitrate, oxalate, panthothenate, phosphate, diphosphate, polygalacturonate, salicylate, stearate, succinate, sulfate, bisulfate, hemisulfate, sulfite, tannate, tartrate, teoclate, triethiodide, and/or pamoate, and the like; or lithium, sodium, potassium, magnesium, calcium, zinc, iron, and/or ammonium ions, and the like; or N,N-dicyclohexylmethyl amine, diisopropylamine, diisopropylethyl amine, ethanolamine, 2,6-lutidine, N-methylmorpholine, pyridine, and/or triethylamine, and the like; or amino acids, and/or protected amino acids, and the like.

When a compound provided herein contains an acidic or basic moiety, it may also be provided as a pharmaceutically acceptable salt (See, e.g., "Handbook of Pharmaceutical Salts, Properties, and Use," Stahl and Wermuth, Ed.; Wiley-VCH and VHCA, Zurich, 2002). As used herein, and unless otherwise specified, the term "pharmaceutically acceptable salts" refers to salts prepared from pharmaceutically acceptable non-toxic acids, including inorganic acids and organic acids, or pharmaceutically acceptable non-toxic bases, including inorganic bases and organic bases.

Suitable acids for use in the preparation of "salts" or "pharmaceutically acceptable salts" include, but are not limited to, acetic, 2,2-dichloroacetic, acylated amino, adipic, alginic, anthranilic, ascorbic, aspartic, L-aspartic, D-aspartic, benzenesulfonic, benzoic, 4-acetamidobenzoic, boric, camphoric, (+)-camphoric, (−)-camphoric, camphorsulfonic, (1R)-(−)-10-camphorsulfonic, (1S)-(+)-10-camphorsulfonic, capric, caproic, caprylic, cinnamic, citric, cyclamic, cyclohexanesulfamic, dodecylsulfuric, ethane-1,2-disulfonic, ethenesulfonic, 2-hydroxy-ethanesulfonic, formic, fumaric, furoic, galactaric, galacturonic, gentistic, glucarenic, glucoheptonic, gluconic, D-gluconic, L-gluconic, glucuronic, D-glucuronic, L-glucuronic, glutamic, D-glutamic, L-glutamic, glutaric, oxoglutaric, α-oxoglutaric, β-oxoglutaric, glycolic, glycidic, hippuric, hydrobromic, hydrochloric, hydroiodic, isethionic, lactic, D-lactic, L-lactic, lactobionic, lauric, maleic, malic, D-malic, L-malic, malonic, mandelic, (+)-mandelic, (−)-mandelic, methanesulfonic, mucic, naphthalene-2-sulfonic, naphthalene-1,5-disulfonic, 1-hydroxy-2-naphthoic, nicotinic, nitric, oleic, orotic, oxalic, palmitic, pamoic, pantothenic, perchloric, phenylacetic, phosphoric, propionic, pyroglutamic, L-pyroglutamic, D-pyroglutamic, saccharic, salicylic, 4-aminosalicylic, sebacic, stearic, succinic, sulfanilic, sulfuric, tannic, tartaric, D-tartaric, L-tartaric, thiocyanic, p-toluenesulfonic, trifluoroacetic, trifluoromethanesulfonic, undecylenic, and valeric acid. In one embodiment, the salt or pharmaceutically acceptable salt is formed from hydrochloric acid. In one embodiment, the salt or pharmaceutically acceptable salt is formed from sulfuric acid. In one embodiment, the salt or pharmaceutically acceptable salt is formed from methanesulfonic acid. In one embodiment, the salt or pharmaceutically acceptable salt is formed from hydrobromic acid. In one embodiment, the salt or pharmaceutically acceptable salt is formed from acetic acid.

Suitable bases for use in the preparation of "salts" or "pharmaceutically acceptable salts", including, but not limited to, inorganic bases, such as magnesium hydroxide, calcium hydroxide, potassium hydroxide, zinc hydroxide, lithium hydroxide, or sodium hydroxide; and organic bases, such as primary, secondary, tertiary, and quaternary, aliphatic and aromatic amines, including L-arginine, benethamine, benzathine, choline, deanol, N,N-dicyclohexylmethyl amine, diethanolamine, diethylamine, dimethylamine, dipropylamine, diisopropylamine, diisopropylethyl amine, 2-(diethylamino)-ethanol, ethanolamine, ethylamine, ethylenediamine, isopropylamine, N-methyl-glucamine, hydrabamine, 1H-imidazole, L-lysine, 2,6-lutidine, morpholine, N-methyl-morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, "salt," "salts" or "pharmaceutically acceptable salt" of 5-azacytidine refers to acid addition salt(s) of 5-azacytidine, derived from inorganic acids and/or organic acids, as described herein elsewhere. In some embodiments, the salt is formed from hydrochloric, hydrobromic, boric, phosphoric, or sulfuric acid. In one embodiment, the salt is formed from hydrochloric acid. In one embodiment, the salt is formed from sulfuric acid. In one embodiment, the salt is formed from methanesulfonic acid. In some embodiments, the salt is formed from acetic, citric, fumaric, maleic, malic, malonic, oxalic, succinic, tartaric, p-toluenesulfonic, trifluoromethanesulfonic, or trifluoroacetic acid.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate (e.g., mono-hydrate, dihydrate, trihydrate, tetrahydrate, and the like).

As used herein, and unless otherwise indicated, the term "polymorph" refers to a solid crystalline form of a compound provided herein or a salt or complex thereof. Different polymorphs of the same compound can exhibit different physical, chemical, biological, and/or spectroscopic properties, among others.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

As used herein, and unless otherwise specified, the term "racemic" or "racemate" refers to about 50% of one enantiomer and about 50% of the corresponding enantiomer relative to all chiral centers in the molecule.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

Unless otherwise specified, the compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

It should be noted that where structural isomers are inter-convertible, the compound provided herein may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, a composition that is "substantially free" of a compound means that the composition contains less than about 20% by weight, less than about 10% by weight, less than about 5% by weight, less than about 3% by weight, less than about 1% by weight, less than about 0.1% by weight, less than about 0.01% by weight, less than about 0.001% by weight, or less than about 0.0001% by weight of the compound.

As used herein, and unless otherwise specified, a composition that is "substantially pure" means that the composition has a purity level of greater than about 80% by weight, greater than about 90% by weight, greater than about 95% by weight, greater than about 97% by weight, greater than about 99% by weight, greater than about 99.5% by weight, greater than about 99.9% by weight, greater than about 99.95% by weight, greater than about 99.99% by weight, greater than about 99.995% by weight, greater than about 99.999% by weight, greater than about 99.9995% by weight, or greater than about 99.9999% by weight.

As used herein, and unless otherwise specified, the term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins (2005); *Handbook of Pharmaceutical Excipients,* 5th Edition, Rowe et al., eds., The Pharmaceutical Press and the American Pharmaceutical Association (2005); and *Handbook of Pharmaceutical Additives,* 3rd Edition, Ash & Ash eds., Gower Publishing Company (2007); *Pharmaceutical Preformulation and Formulation,* 2nd Edition, Gibson ed., CRC Press (2009).

As used herein, and unless otherwise specified, the terms "active ingredient," "active substance," or "active pharmaceutical ingredient" refers to a compound or a substance, which is administered, alone or in combination with other pharmaceutically active compound(s), and/or one or more pharmaceutically acceptable excipients, to a subject for treating, preventing, and/or ameliorating one or more symptoms of a condition, disorder, or disease. As used herein, "active ingredient," "active substance," and "active pharmaceutical ingredient" may be a pharmaceutically acceptable salt, solvate, hydrate, polymorph, or optically active isomer of a compound described herein.

As used herein, and unless otherwise specified, the terms "drug" and "therapeutic agent" refer to a compound, or a pharmaceutical composition thereof, which is administered to a subject for treating, preventing, managing, and/or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human.

Unless otherwise specified, the compound provided herein may be provided as a prodrug, which is a functional derivative of the compound, for example, 5-azacytidine, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See *Prodrugs: Challenges and Rewards,* Valentino J. Stella et al., eds., Springer Press, 2007; Harper, *Progress in Drug Research,* 1962, 4, 221-294; Morozowich et al. in "Design of Biopharmaceutical Properties through Prodrugs and Analogs," Roche ed., APHA Acad. Pharm. Sci., 1977; "Bioreversible Carriers in Drug in Drug Design, Theory and Application," Roche ed., APHA Acad. Pharm. Sci., 1987; "Design of Prodrugs," Bundgaard, Elsevier, 1985; Wang et al., *Curr. Pharm. Design,* 1999, 5, 265-287; Pauletti et al., *Adv. Drug. Delivery Rev.,* 1997, 27, 235-256; Mizen et al., *Pharm. Biotech.,* 1998, 11, 345-365; Gaignault et al., *Pract. Med. Chem.,* 1996, 671-696; Asgharnejad in "Transport Processes in Pharmaceutical Systems," Amidon et al., ed., Marcell Dekker, 185-218, 2000; Balant et al., *Eur. J. Drug Metab. Pharmacokinet.,* 1990, 15, 143-53; Balimane and Sinko, *Adv. Drug Delivery Rev.,* 1999, 39, 183-209; Browne, *Clin. Neuropharmacol.,* 1997, 20, 1-12; Bundgaard, *Arch. Pharm. Chem.,* 1979, 86, 1-39; Bundgaard, *Controlled Drug Delivery,* 1987, 17, 179-96; Bundgaard, *Adv. Drug Delivery Rev.,* 1992, 8, 1-38; Fleisher et al., *Adv. Drug Delivery Rev.,* 1996, 19, 115-130; Fleisher et al., *Methods Enzymol.,* 1985, 112, 360-381; Farquhar et al., *J. Pharm. Sci.,* 1983, 72, 324-325; Freeman et al., *J. Chem. Soc., Chem. Commun.,* 1991, 875-877; Friis and Bundgaard, *Eur. J. Pharm. Sci.,* 1996, 4, 49-59; Gangwar et al., *Des. Biopharm. Prop. Prodrugs Analogs,* 1977, 409-421; Nathwani and Wood, *Drugs,* 1993, 45, 866-94; Sinhababu and Thakker, *Adv. Drug Delivery Rev.,* 1996, 19, 241-273; Stella et al., *Drugs,* 1985, 29, 455-73; Tan et al., *Adv. Drug Delivery Rev.,* 1999, 39, 117-151; Taylor, *Adv. Drug Delivery Rev.,* 1996, 19, 131-148; Valentino and Borchardt, *Drug Discovery Today,* 1997, 2, 148-155; Wiebe and Knaus, *Adv. Drug Delivery Rev.,* 1999, 39, 63-80; and Waller et al., *Br. J. Clin. Pharmac.,* 1989, 28, 497-507.

Unless otherwise specified, the compounds described herein, including intermediates useful for the preparation of the compounds, which contain reactive functional groups (such as, without limitation, carboxy, hydroxy, and amino moieties), also encompass suitable protected derivatives thereof. "Protected derivatives" are those compounds in which a reactive site or sites are blocked with one or more protecting groups (also known as blocking groups). Suitable protecting groups for carboxy moieties include benzyl, t-butyl, and the like. Suitable protecting groups for amino and amido groups include acetyl, t-butyloxycarbonyl, benzyloxycarbonyl, silyl, and the like. Suitable protecting groups for hydroxy include benzyl, acetyl, silyl, and the like. Other suitable protecting groups are well known to those of ordinary skill in the art. The choice and use of protecting groups and the reaction conditions to install and remove protecting groups are described, for example, in T. W. Greene & P. G. M. Wuts, "Protective Groups in Organic Synthesis", Third Ed., John Wiley & Sons, Inc. 1999.

As used herein, and unless otherwise indicated, the term "process" refers to the methods disclosed herein which are useful for preparing a compound provided herein. Modifications to the methods disclosed herein (e.g., starting materials, reagents, protecting groups, solvents, temperatures, reaction times, purification) that are well known to those of ordinary skill in the art are also encompassed by the present disclosure.

As used herein, and unless otherwise indicated, the term "adding," "reacting," "mixing," or the like means contacting one reactant, reagent, solvent, catalyst, reactive group, or the like with another reactant, reagent, solvent, catalyst, reactive group, or the like. Unless otherwise specified, reactants, reagents, solvents, catalysts, reactive group, or the like can be added individually, simultaneously, or separately, or can be added in any order. They can be added in the presence or absence of heat, and can optionally be added under an inert atmosphere. "Reacting" can refer to in situ formation or intra-molecular reaction where the reactive groups are in the same molecule.

As used herein, and unless otherwise indicated, a reaction that is "substantially complete" or is driven to "substantial completion" means that the reaction contains more than about 50% by percent yield, more than about 60% by percent yield, more than about 70% by percent yield, more than about 80% by percent yield, more than about 90% by percent yield, more than about 95% by percent yield, or more than about 97% by percent yield of the desired product. Alternatively, the terms "substantially complete" or "substantial completion" means that the reaction contains less than about 50% of a starting material relative to its starting amount, less than about 40%, less than about 30%, less than about 20%, less than about 10%, less than about 5%, less than about 3%, less than about 1%, less than about 0.5%, less than about 0.1%, less than about 0.05%, or less than about 0.01% of a starting material relative to its starting amount.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

B. Processes

Provided herein are processes for the preparation of 5-azacytidine, or a salt, solvate, hydrate, or polymorph thereof. In general, the processes provided herein encompass safe, efficient, cost effective, and/or readily scaleable processes useful for the large scale or commercial production of 5-azacytidine, or a salt, solvate, hydrate, or polymorph thereof.

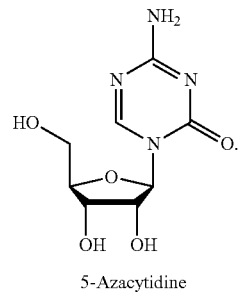

5-Azacytidine

In one embodiment, provided herein are processes for the production of 5-azacytidine, or a salt, solvate, hydrate, or polymorph thereof, that is substantially pure. In one embodiment, provided herein are processes for the production of 5-azacytidine, or a salt, solvate, hydrate, or polymorph thereof, that is substantially chemically pure. In one embodiment, provided herein are processes for the production of 5-azacytidine, or a salt, solvate, hydrate, or polymorph thereof, that is substantially physically pure. In one embodiment, provided herein are processes for the production of 5-azacytidine, or a salt, solvate, hydrate, or polymorph thereof, suitable for use in humans, such as for treating, preventing, and/or managing diseases or conditions including cancer, disorders related to abnormal cell proliferation, hematologic disorders, and myelodysplastic syndromes (MDS), among others.

In one embodiment, the processes provided herein encompass safe, cost-effective, and/or efficient means for the large scale or commercial production of 5-azacytidine, or a salt, solvate, hydrate, or polymorph thereof. In one embodiment, the processes provided herein produce 5-azacytidine, or a salt, solvate, hydrate, or polymorph thereof, on a scale of greater than 1 gram, greater than 10 gram, greater than 25 gram, greater than 50 gram, greater than 100 gram, greater than 250 gram, greater than 500 gram, greater than 1,000 gram, greater than 5,000 gram, greater than 10,000 gram, greater than 50,000 gram, or greater than 100,000 gram.

In one embodiment, the processes provided herein produce 5-azacytidine, or a salt, solvate, hydrate, or polymorph thereof, in an overall yield of greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95%, wherein the yield is calculated based on starting material, such as, e.g., 5-azacytosine or a protected β-D-ribofuranose (e.g., a compound of formula B).

In one embodiment, the processes provided herein produce 5-azacytidine, or a salt, solvate, hydrate, or polymorph thereof, that is substantially pure. In one embodiment, the purity of the 5-azacytidine, or a salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch. In one embodiment, the total impurities in the 5-azacytidine, or a salt, solvate, hydrate, or polymorph thereof, is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w relative to the total batch. In one embodiment, an individual impurity component in the 5-azacytidine, or a salt, solvate, hydrate, or polymorph thereof, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w relative to the total batch. In one embodiment, the processes provided herein produce 5-azacytidine, or a salt, solvate, hydrate, or polymorph thereof, that is substantially physically and/or chemically pure.

In one embodiment, the processes provided herein produce 5-azacytidine, or a salt, solvate, hydrate, or polymorph thereof, that is substantially physically pure. In one embodiment, the processes provided herein produce a polymorph or a crystalline form of 5-azacytidine that is substantially physically pure. In one embodiment, the physical purity of the 5-azacytidine, or a salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch. In one embodiment, the total impurities in the 5-azacytidine, or a salt, solvate, hydrate, or polymorph thereof, is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w relative to the total batch. In one embodiment, an individual impurity component in the 5-azacytidine, or a salt, solvate, hydrate, or polymorph thereof, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w relative to the total batch.

In one embodiment, the processes provided herein produce 5-azacytidine, or a salt, solvate, hydrate, or polymorph thereof, that is substantially chemically pure. In one embodiment, the processes provided herein produce a polymorph or a crystalline form of 5-azacytidine that is substantially chemically pure. In one embodiment, the chemical purity of the 5-azacytidine, or a salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch. In one embodiment, the total impurities in the 5-azacytidine, or a salt, solvate, hydrate, or polymorph thereof, is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w relative to the total batch. In one embodiment, an individual impurity component in the 5-azacytidine, or a salt, solvate, hydrate, or polymorph thereof, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w relative to the total batch.

In one embodiment, the impurity is detectable by HPLC (high performance liquid chromatography). In one embodiment, the impurity includes, but is not limited to, 6-amino-5-azacytosine, 2,4,6-triaminotriazine, 2,4-diaminotriazine, 6-methyl-5-azacytosine, 6-amino-5-azacytidine, 6-methyl-5-azacytidine, and 1-β-D-ribofuranosyl-3-guanylurea, among others. In one embodiment, the impurity is a metal based impurity, such as for example, impurities comprising tin or iron. In one embodiment, the impurity is a volatile organic compound, such as for example, methanol, dichloromethane, toluene, or triethylamine. In one embodiment, the impurity is an organic solvent, such as for example, methanol, dichloromethane, toluene or dimethylsulfoxide. In one embodiment, the weight loss on drying (LOD) of the 5-azacytidine, or a salt, solvate, hydrate, or polymorph thereof, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w relative to the total batch.

In one embodiment, provided herein are processes for preparing 5-azacytidine, or a salt, solvate, hydrate, or polymorph thereof, comprising the steps of reacting a silylated 5-azacytosine with a protected β-D-ribofuranose in the presence of a metallic Lewis acid to yield a protected 5-azacytidine, deprotecting the protected 5-azacytidine to yield 5-azacytidine, and purifying the 5-azacytidine to yield 5-azacytidine, or a salt, solvate, hydrate, or polymorph thereof, that is substantially free of one or more impurities, including but not limited to, a metal-based impurity.

In one embodiment, the contemplated metal-based impurity comprises of the same metal element as that in the metallic Lewis acid, including but not limited to, tin, iron, zinc, titanium, aluminum, or boron, derived from metallic Lewis acid such as, stannic chloride, ferric chloride, zinc chloride, titanium tetrachloride, aluminum chloride, aluminum alkyl chloride, aluminum dialkyl chloride, aluminum trifluoride, or boron trifluoride, used in the preceding coupling reaction. In one embodiment, the total metal-based impurities in the 5-azacytidine, or a salt, solvate, hydrate, or polymorph thereof, is less than about 500 ppm (parts per million) w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch. In one embodiment, an individual metal based impurity, such as for example, tin or iron content, in the 5-azacytidine, or a salt, solvate, hydrate, or polymorph thereof, is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, less than about 0.1 ppm w/w, less than about 0.05 ppm w/w, less than about 0.02 ppm w/w, or less than about 0.01 ppm w/w relative to the total batch.

In specific embodiments, provided herein are processes for preparing 5-azacytidine, or a salt, solvate, hydrate, or polymorph thereof, comprising any one, two, three, four, five, or six of the steps of:

(a) reacting 5-azacytosine with a silylating reagent to yield a silylated 5-azacytosine;
(b) reacting the silylated 5-azacytosine with an acyl protected β-D-ribofuranose in the presence of a metallic Lewis acid; and quenching the reaction with water and at least one neutralizing reagent to yield a protected 5-azacytidine;
(c) reacting the protected 5-azacytidine with a base, selected from the group consisting of alkoxide, ammonia, and tetra-substituted ammonium hydroxide, in an alcohol to yield 5-azacytidine;
(d) contacting the 5-azacytidine from step (c) with an acid in an organic solvent to yield a salt of 5-azacytidine;
(e) contacting the salt of 5-azacytidine from step (d) with a base in an organic solvent to yield 5-azacytidine as a free base; and
(f) re-crystallizing the 5-azacytidine from step (e).

In one embodiment, the silylated 5-azacytosine is a compound of formula (A):

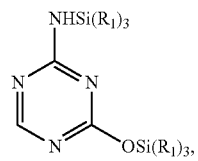

(A)

wherein each $R_1$ is independently optionally substituted $C_1$-$C_{10}$ alkyl, optionally substituted $C_3$-$C_{10}$ cycloalkyl, or optionally substituted $C_6$-$C_{10}$ aryl. In some embodiments, $R_1$ is straight chain alkyl, branched alkyl, cycloalkyl, or aryl, including but not limited to, methyl, ethyl, i-propyl, t-butyl, phenyl, xylyl, and benzyl. In some embodiments, $R_1$ is methyl. In some embodiments, $R_1$ is ethyl. In some embodiments, $R_1$ is isopropyl. In some embodiments, the silylated 5-azacytosine is:

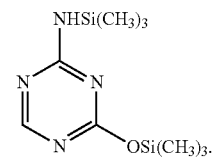

A variety of suitable protecting groups may be used to protect the hydroxyl groups in a β-D-ribofuranose to form a protected β-D-ribofuranose, which may be coupled with a silylated 5-azacytosine (e.g., a compound of formula (A)). The protecting groups may be removed under suitable conditions at a later stage of the reaction sequence (e.g., after the protected 5-azacytidine is formed). One skilled in the art will recognize and select suitable protecting groups for the hydroxyl moieties of β-D-ribofuranose, and will select appropriate conditions for installing such protecting groups. See, e.g., T. W. Greene, & P. G. M. Wuts, "Protective Groups in Organic Synthesis", Third Ed., John Wiley & Sons, Inc., 1999. In one embodiment, the protected β-D-ribofuranose is purchased from a commercial source or prepared following a literature procedure. In one embodiment, the protected β-D-ribofuranose has one or more acyl, alkyl, silyl, acetal, or ketal protecting groups, or a combination thereof. In one embodiment, the protected β-D-ribofuranose has one, two, three, or four of the hydroxyl groups protected by suitable protecting group(s). In one embodiment, all four hydroxyl groups are protected in the protected β-D-ribofuranose. In one embodiment, the protected β-D-ribofuranose is acyl protected β-D-ribofuranose. In one embodiment, the protected β-D-ribofuranose is tetra-acyl protected β-D-ribofuranose.

In one embodiment, the protected β-D-ribofuranose is a compound of formula (B):

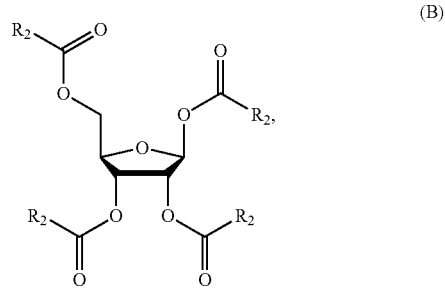

(B)

wherein each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl. In some embodiments, $R_2$ is optionally substituted methyl or optionally substituted phenyl. In some embodiments, $R_2$ is methyl. In some embodiments, $R_2$ is phenyl. In some embodiments, the protected β-D-ribofuranose is:

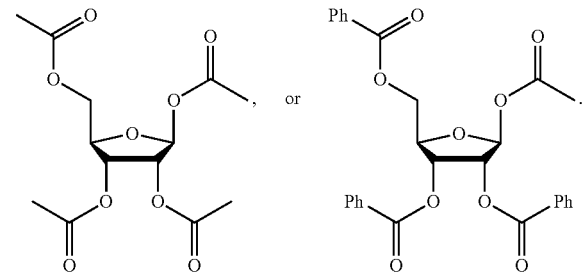

In one embodiment, the metallic Lewis acid is a Lewis acid that contains a metal atom, including, but not limited to, tin, iron, zinc, titanium, aluminum, and boron. In one embodiment, the metallic Lewis acid is selected from the group consisting of stannic chloride, ferric chloride, zinc chloride, titanium tetrachloride, aluminum chloride, aluminum alkyl chloride (e.g., $EtAlCl_2$), aluminum dialkyl chloride (e.g., $Et_2AlCl$), aluminum fluoride, boron trifluoride, and the like. In one embodiment, the metallic Lewis acid is stannic chloride or ferric chloride. In one embodiment, the metallic Lewis acid is stannic chloride. In one embodiment, the metallic Lewis acid is ferric chloride.

In one embodiment, the protected 5-azacytidine is a compound of formula (C) or (D):

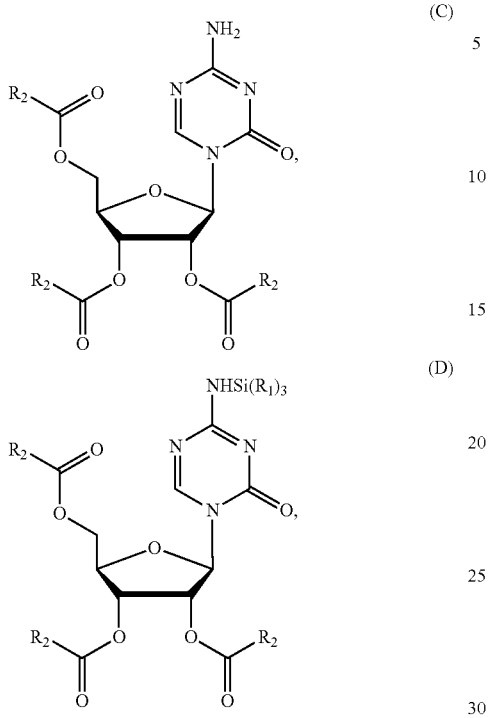

wherein each $R_1$ is independently optionally substituted $C_1$-$C_{10}$ alkyl, optionally substituted $C_3$-$C_{10}$ cycloalkyl, or optionally substituted $C_6$-$C_{10}$ aryl; and each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl. In some embodiments, $R_1$ is straight chain alkyl, branched alkyl, cycloalkyl, or aryl, including but not limited to, methyl, ethyl, i-propyl, t-butyl, phenyl, xylyl, and benzyl. In some embodiments, $R_1$ is methyl. In some embodiments, $R_2$ is optionally substituted methyl or optionally substituted phenyl. In some embodiments, $R_2$ is methyl. In some embodiments, $R_2$ is phenyl.

In one embodiment, the protected 5-azacytidine is a compound of formula (C).

In one embodiment, a compound of formula (D) is formed from the coupling reaction between a silylated 5-azacytosine and a protected β-D-ribofuranose, and then converted to a compound of formula (C) during the aqueous work-up of the reaction. In one embodiment, a compound of formula (C) is isolated after the aqueous work-up of the reaction.

In specific embodiments, the protected 5-azacytidine is:

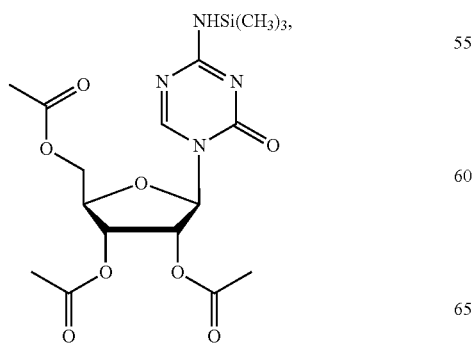

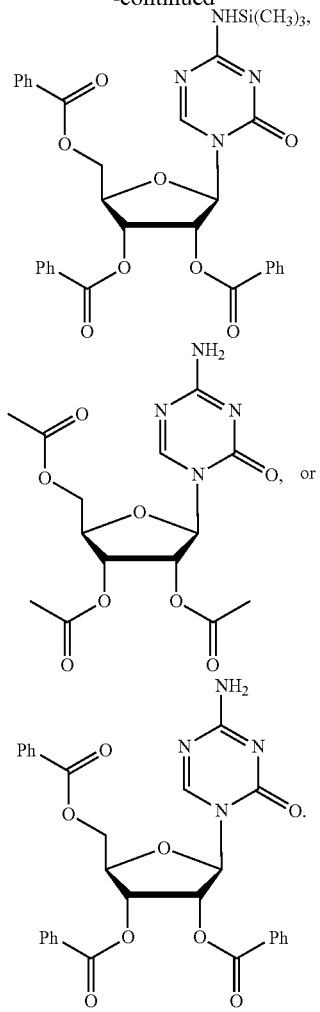

In specific embodiments, the protected 5-azacytidine is:

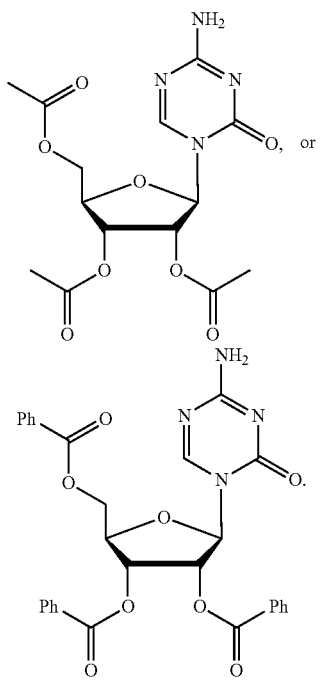

27

In one embodiment, the protected 5-azacytidine is:

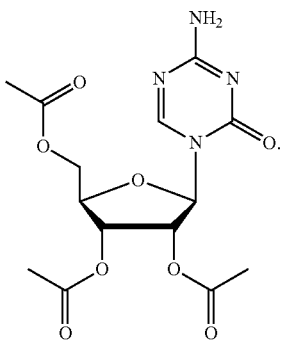

In one embodiment, provided herein are processes for preparing 5-azacytidine, or a salt, solvate, hydrate, or polymorph thereof, as described in Scheme 1 below:

SCHEME 1

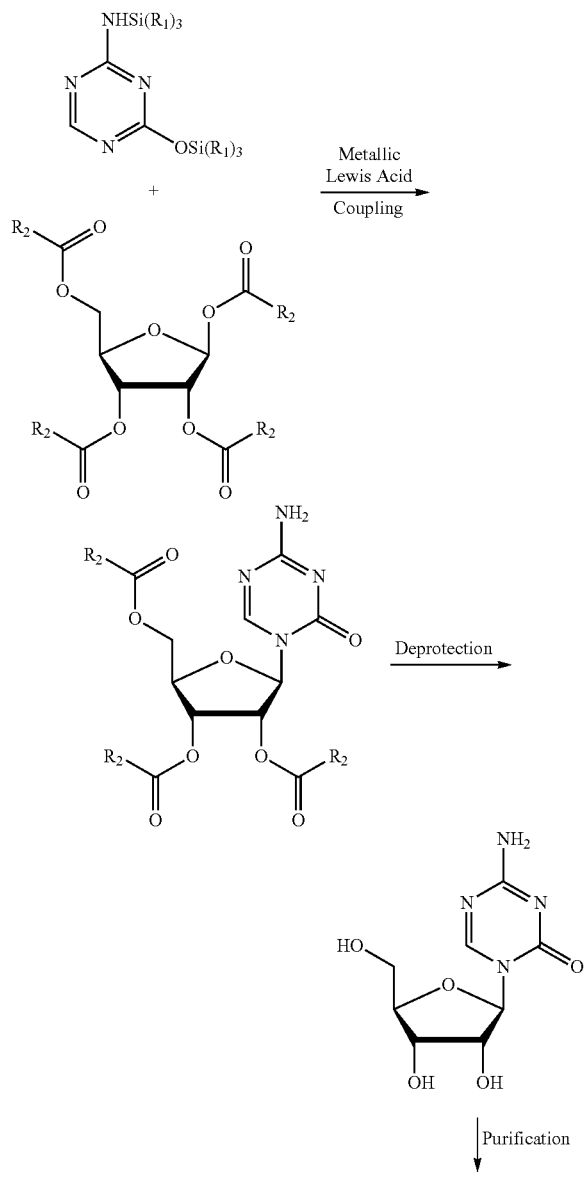

28

-continued

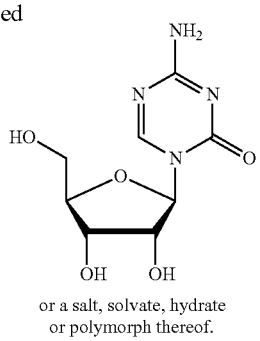

or a salt, solvate, hydrate or polymorph thereof.

wherein $R_1$ and $R_2$ are defined herein elsewhere.

In one embodiment, purification of 5-azacytidine encompasses the formation of a salt of 5-azacytidine to substantially reduce the impurity content, such as, e.g., a metal-based impurity, in a given batch of 5-azacytidine. In one embodiment, an acid addition salt of 5-azacytidine is formed to substantially reduce the impurity content, such as, e.g., a metal-based impurity, in a given batch of 5-azacytidine. For example, in specific embodiments, 5-azacytidine is stirred with an acid, such as hydrochloric acid, in a solvent, such as an alcohol, for example, methanol. The acid addition salt of 5-azacytidine is produced. The salt of 5-azacytidine is then isolated, such as for example, collected by filtration, and washed with a solvent, such as an alcohol, for example, methanol. Optionally, the salt of 5-azacytidine is dried under vacuum at ambient temperature or at elevated temperature, such as 50-60° C. The salt of 5-azacytidine may be isolated as a crystalline solid, which has a substantially reduced impurity content, such as metal content, for example, tin or iron content. In one embodiment, the salt of 5-azacytidine is substantially physically pure. In one embodiment, the salt of 5-azacytidine is substantially chemically pure.

In one embodiment, the salt of 5-azacytidine is treated with a base to break the acid addition salt of 5-azacytidine and to form the free base of 5-azacytidine. In some embodiments, about 1.0, about 1.1, about 1.2, about 1.3, about 1.4, about 1.5, about 1.6, about 1.7, about 1.8, about 1.9, about 2.0, about 2.5, or about 3.0 equivalent of the base is used to generate the free base of 5-azacytidine from the acid addition salt. In other embodiments, greater than about 3.0 equivalent of the base is used to generate the free base of 5-azacytidine from the acid addition salt. In specific embodiments, for example, the salt of 5-azacytidine is stirred with a base, such as, an organic base, for example, triethylamine, in a solvent, such as an alcohol, for example, methanol. The free base of 5-azacytidine is formed. The free base of 5-azacytidine is then isolated, such as for example, collected by filtration, and washed with a solvent, such as an alcohol, for example, methanol. Washing may be continued until the filtrate is substantially free of the acidic salt counter ion, such as chloride. Optionally, the isolated free base of 5-azacytidine is dried under vacuum at ambient temperature or at elevated temperature, such as 50-60° C. The free base of 5-azacytidine may be isolated as a crystalline solid, which has a substantially reduced impurity content, such as metal content, for example, tin or iron content. In one embodiment, the free base of 5-azacytidine is substantially physically pure. In one embodiment, the free base of 5-azacytidine is substantially chemically pure.

In one embodiment, 5-azacytidine is purified by re-crystallization. For example, in specific embodiments, 5-azacytidine or a salt thereof is dissolved in a solvent, such as dimethylsulfoxide (DMSO), at a temperature sufficient to allow the 5-azacytidine to dissolve, such as a temperature of greater than about 85° C. Optionally, the solution of 5-azacytidine is filtered, for example, through filter paper. The filtration may be performed at an elevated temperature, such as a temperature of greater than about 85° C. Optionally, hot DMSO may be used to wash the particles retained by filtration. To the solution of 5-azacytidine is added an anti-solvent, such as, e.g., an alcohol, for example, methanol. The mixture is cooled, and 5-azacytidine re-crystallizes. In other embodiments, the anti-solvent may be added during the cooling step of the DMSO solution of 5-azacytidine. For example, the hot DMSO solution of 5-azacytidine may be first cooled to a certain temperature, the anti-solvent is then added, followed by further cooling of the resulting mixture. The crystalline 5-azacytidine may be collected by filtration. The crystalline 5-azacytidine may be washed with a solvent, such as, e.g., an alcohol, for example, methanol. In some embodiments, the re-crystallized 5-azacytidine is dried under vacuum at ambient temperature or at elevated temperature, such as about 40° C., about 50° C., about 60° C., about 70° C., about 80° C., or about 90° C. The re-crystallized 5-azacytidine may be isolated as a crystalline solid, which is substantially free of impurity content, such as metal content, for example, tin or iron content. In one embodiment, the re-crystallized 5-azacytidine is substantially physically pure. In one embodiment, the re-crystallized 5-azacytidine is substantially chemically pure.

In one embodiment, purification of 5-azacytidine comprises a combination of the salt formation step, the free base formation step, and/or the re-crystallization step. In one embodiment, purification of 5-azacytidine comprises the steps of (1) salt formation, (2) free base formation, and (3) re-crystallization. In another embodiment, purification of 5-azacytidine comprises the steps of (1) salt formation, (2) re-crystallization, and (3) free base formation. In another embodiment, purification of 5-azacytidine comprises the steps of (1) re-crystallization, (2) salt formation, and (3) free base formation. In another embodiment, purification of 5-azacytidine comprises the steps of (1) salt formation, and (2) free base formation. In another embodiment, purification of 5-azacytidine comprises the steps of (1) salt formation, and (2) re-crystallization. In another embodiment, purification of 5-azacytidine comprises the steps of (1) re-crystallization, and (2) salt formation.

In one embodiment, provided herein are processes for preparing 5-azacytidine, or a salt, solvate, hydrate, or polymorph thereof, as described in Scheme 2 below:

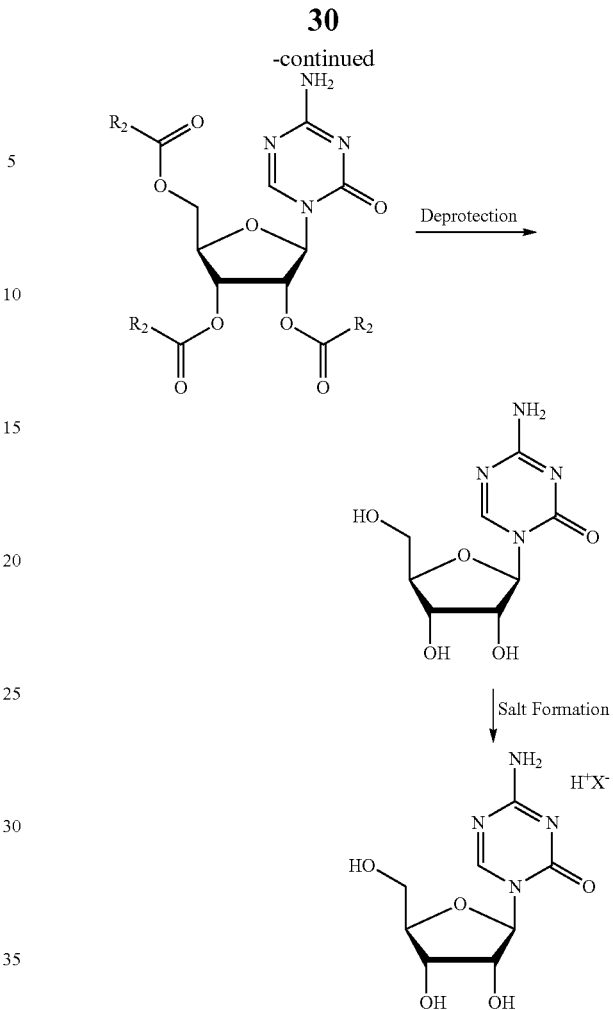

wherein $R_1$ and $R_2$ are defined herein elsewhere, $X^-$ is one or more salt counter ion(s), as defined herein elsewhere.

In one embodiment, provided herein are processes for preparing 5-azacytidine, or a salt, solvate, hydrate, or polymorph thereof, as described in Scheme 3 below:

SCHEME 2

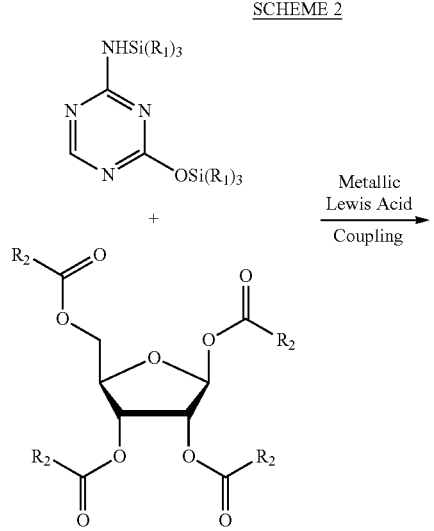

SCHEME 3

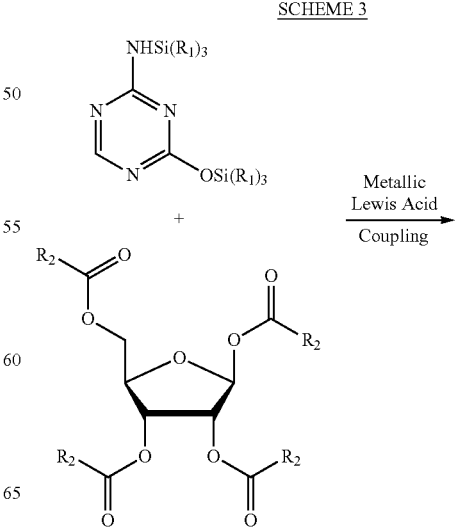

31
-continued
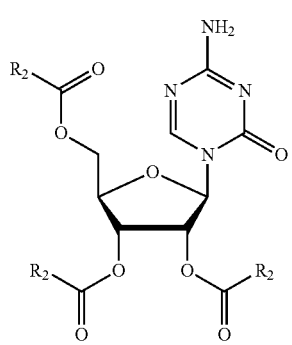
Deprotection →
32
-continued
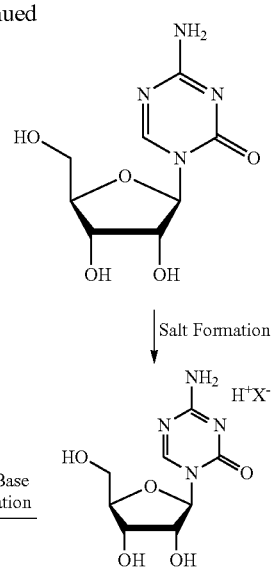
wherein $R_1$ and $R_2$ are defined herein elsewhere, $X^-$ is one or more salt counter ion(s), as defined herein elsewhere.
In one embodiment, provided herein are processes for preparing 5-azacytidine, or a salt, solvate, hydrate, or polymorph thereof, as described in Scheme 4 below:
SCHEME 4
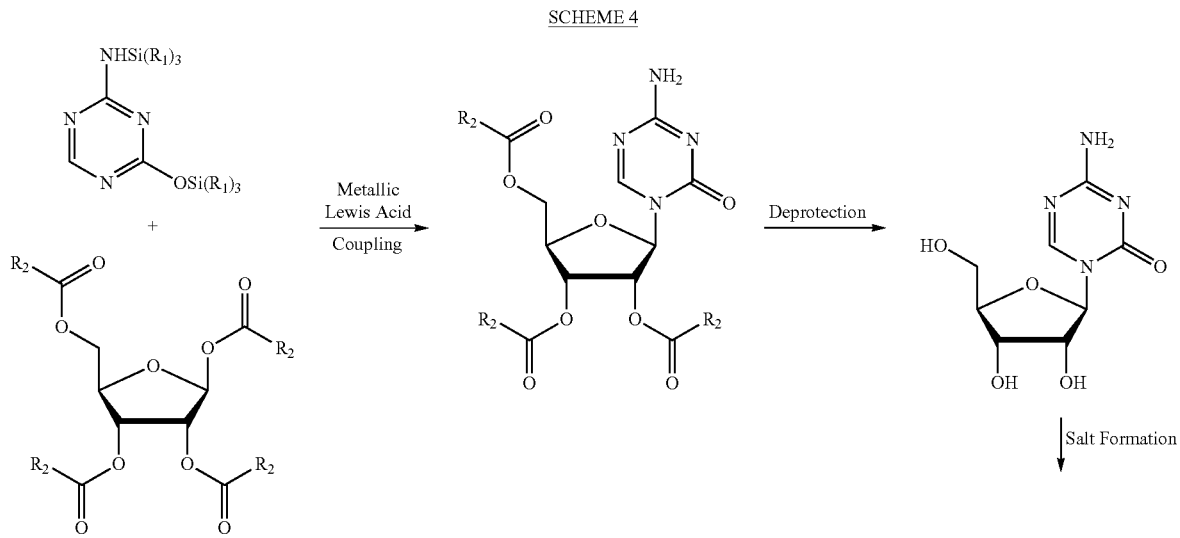
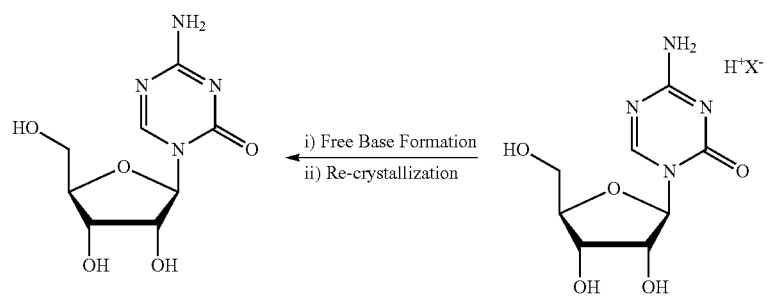

wherein $R_1$ and $R_2$ are defined herein elsewhere, $X^-$ is one or more salt counter ion(s), as defined herein elsewhere.

In one embodiment, provided herein are processes for preparing 5-azacytidine, or a salt, solvate, hydrate, or polymorph thereof, comprising any one, two, three, four, five, or six of the steps of:

(a) reacting 5-azacytosine with a silylating reagent to yield a silylated 5-azacytosine;
(b) reacting the silylated 5-azacytosine with an acyl protected β-D-ribofuranose in the presence of a metallic Lewis acid; and quenching the reaction with water and at least one neutralizing reagent to yield a protected 5-azacytidine;
(c) reacting the protected 5-azacytidine with a base, selected from the group consisting of alkoxide, ammonia, and tetra-substituted ammonium hydroxide, in an alcohol to yield 5-azacytidine;
(d) contacting the 5-azacytidine from step (c) with an acid in an organic solvent to yield a salt of 5-azacytidine;
(e) contacting the salt of 5-azacytidine from step (d) with a base in an organic solvent to yield 5-azacytidine as a free base; and
(f) re-crystallizing the 5-azacytidine from step (e).

1. Step (a)—Silylation of 5-Azacytosine

In one embodiment, the silylating reagent used in step (a) is a trimethylsilyl (TMS) reagent (i.e. $R_1$ is methyl). In one embodiment, the silylating reagent used in step (a) is a mixture of two or more TMS reagents. In one embodiment, the silylation reagent used in step (a) is selected from the group consisting of hexamethyldisilazane (HMDS) and chlorotrimethylsilane (TMSCl). In some embodiments, the silylating reagent comprises of a mixture of HMDS and TMSCl. In some embodiments, the silylating reagent comprises HMDS. In some embodiments, the silylating reagent is HMDS.

In one embodiment, the silylating reagent used in step (a) is in molar excess relative to 5-azacytosine. In one embodiment, the silylation reaction of step (a) uses excess HMDS. In one embodiment, the silylation reaction of step (a) uses an excess of about 7-volume of HMDS (e.g., 700 mL of HMDS relative to 100 g of 5-azacytosine). In one embodiment, the silylation reaction of step (a) uses an excess of about 4-volume, about 5-volume, about 7-volume, about 10-volume, about 12-volume, or about 14-volume, of HMDS, relative to 5-azacytosine.

In one embodiment, the silylation reaction of step (a) is carried out in the presence of a catalyst. In one embodiment, the catalyst is ammonium sulfate.

In one embodiment, the silylation reaction is carried out at room temperature. In one embodiment, the silylation reaction is carried out at elevated temperature. In one embodiment, the silylation reaction is carried out at a temperature of greater than about 50° C., greater than about 60° C., greater than about 70° C., greater than about 80° C., greater than about 90° C., greater than about 100° C., greater than about 110° C., greater than about 120° C., greater than about 130° C., greater than about 140° C., greater than about 150° C., greater than about 160° C., greater than about 170° C. In one embodiment, the silylation reaction is carried out at a temperature of between about 50° C. and about 170° C., between about 60° C. and about 165° C., between about 70° C. and about 160° C., between about 80° C. and about 155° C., between about 90° C. and about 150° C., between about 100° C. and about 145° C., between about 110° C. and about 140° C., between about 120° C. and about 140° C. In one embodiment, the reaction is carried out at a temperature of about 125° C. In one embodiment, the reaction is carried out at a temperature of about 130° C.

In one embodiment, the silylation reaction is carried out under an inert atmosphere. In one embodiment, the silylation reaction is carried out under nitrogen. In one embodiment, the silylation reaction is carried out under argon.

The reaction time of the silylation reaction can vary from about 0.5 hr to about 24 hr, depending on the reaction temperature, the silylating reagent used, and the concentration of reagents in the reaction mixture. In general, the higher the reaction temperature, the shorter the reaction time. In one embodiment, the reaction time is about 0.5 hr, about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, or about 24 hr. In one embodiment, the reaction time is about 2 hr, about 3 hr, about 4 hr, about 5 hr, or about 6 hr, at a reaction temperature of about 125° C., in the presence of a catalyst, such as ammonium sulfate, when the silylating reagent comprises HMDS. In some embodiments, the reaction mixture becomes a clear solution when the reaction is substantially complete.

In one embodiment, the silylation reaction is carried out in the absence of a solvent using a molar excess of silylating reagent, and optionally in the presence of a catalyst. In one embodiment, the silylation reaction is carried out in the presence of a solvent. In one embodiment, the silylation reaction is carried out in the presence of a polar organic solvent, such as for example, acetonitrile. In one embodiment, the solvent is removed under vacuum (e.g., 10-15 mmHg) after the completion of the reaction.

In one embodiment, the silylated 5-azacytosine is a compound of formula (A):

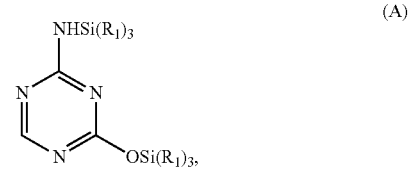

wherein $R_1$ is defined herein elsewhere. In one embodiment, the silylated 5-azacytosine is:

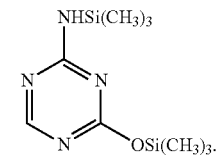

In one embodiment, the silylated 5-azacytosine is isolated as a solid. In other embodiments, the silylated 5-azacytosine is used directly in step (b) without isolation. In some embodiments, the silylated 5-azacytosine is isolated under an inert atmosphere, such as nitrogen and/or argon. In one embodiment, the silylated 5-azacytosine is isolated by removing the silylating reagents using vacuum distillation. In one embodiment, the silylated 5-azacytosine is isolated by filtration.

In one embodiment, the silylated 5-azacytidine is prepared by heating a suspension of 5-azacytosine, one or more TMS reagents (present in an excess molar ratio over the 5-azacytosine) and a catalyst, such as for example, ammonium sulfate, at reflux without a solvent until a clear solution results, wherein trimethylsilylated 5-azacytidine (i.e. a compound of formula (A) wherein $R_1$ is methyl) is formed. In some embodiments, the TMS reagent is HMDS.

In one embodiment, the silylated 5-azacytosine is isolated by techniques known in the art. In one embodiment, the isolated silylated 5-azacytosine is used with or without drying in the subsequent coupling reaction with the protected β-D-ribofuranose. In one embodiment, the silylation reaction mixture is cooled to ambient temperature, where the silylated 5-azacytosine crystallizes from the reaction mixture. In one embodiment, the crystallization of silylated 5-azacytosine is facilitated by a suitable anti-solvent, such as for example, heptane. In one embodiment, the silylated 5-azacytosine is isolated by filtration under inert atmosphere. In one embodiment, the silylated 5-azacytosine is washed with a suitable washing solvent, such as for example, heptane. In another embodiment, the silylated 5-azacytosine is isolated as a solid residue by removing excess TMS reagent and any solvent (if present) by vacuum distillation. In one embodiment, a suitable solvent, such as for example, toluene, is added to the solid residue of silylated 5-azacytosine, and the solvent is removed by vacuum distillation, wherein any residual TMS reagent, such as HMDS, is removed together with the solvent. In one embodiment, the excess HMDS is recovered by vacuum distillation and may be reused as a silylating reagent. In one embodiment, the isolated silylated 5-azacytosine is dissolved in a suitable solvent, such as for example, dichloromethane, acetonitrile, or 1,2-dichloroethane, for use in the subsequent coupling step.

In one embodiment, the silylated 5-azacytosine is prepared "in situ" from 5-azacytosine and an equivalent molar amount of silylating reagent(s) (such as a mixture of HMDS and TMSCl) in a suitable solvent in the presence or absence of a catalyst at reflux. In one embodiment, the solvent is a dry organic solvent. In one embodiment, the solvent is a dry non-polar organic solvent, including but not limited to, a halogenated solvent. In one embodiment, the solvent is a dry polar organic solvent, including but not limited to, acetonitrile. The resulting silylated 5-azacytosine can be used directly in the subsequent coupling step without isolation.

2. Step (b)—Coupling

In one embodiment, the acyl protected β-D-ribofuranose used in step (b) is a compound of formula (B):

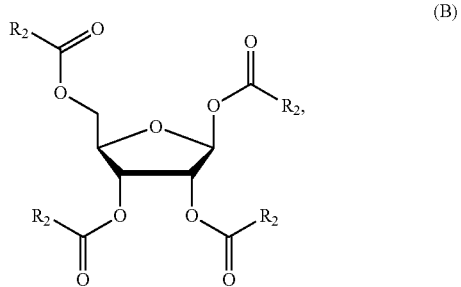
(B)

wherein $R_2$ is defined herein elsewhere. In one embodiment, the acyl protected β-D-ribofuranose is:

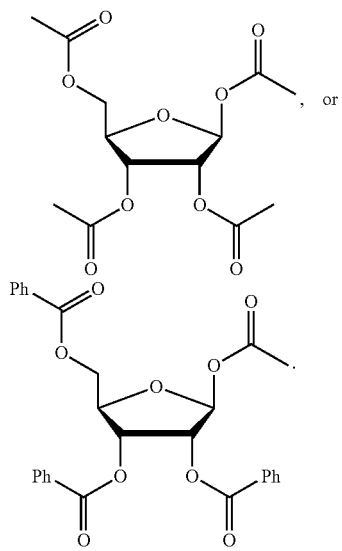
, or

In one embodiment, the acyl protected β-D-ribofuranose used in step (b) may be purchased from a commercial supplier (e.g., Suven Life Sciences Limited). In one embodiment, the acyl protected β-D-ribofuranose used in step (b) may be prepared from β-D-ribofuranose following literature procedures.

In one embodiment, the metallic Lewis acid used in step (b) is a Lewis acid that contains a metal atom, such as, e.g., tin, iron, zinc, titanium, aluminum, and boron. In one embodiment, the metallic Lewis acid is selected from the group consisting of stannic chloride, ferric chloride, zinc chloride, titanium tetrachloride, aluminum chloride, aluminum alkyl chloride (e.g., $EtAlCl_2$), aluminum dialkyl chloride (e.g., $Et_2AlCl$), aluminum fluoride, boron trifluoride, and the like. In one embodiment, the metallic Lewis acid is stannic chloride or ferric chloride. In one embodiment, the metallic Lewis acid is stannic chloride. In one embodiment, the metallic Lewis acid is ferric chloride.

In one embodiment, the reaction of step (b) is carried out in a dry organic solvent. In one embodiment, the reaction of step (b) is carried out in a solvent with low water solubility. In one embodiment, the reaction of step (b) is carried out in a dry organic non-polar solvent with low water solubility. In one embodiment, the reaction of step (b) is carried out in a halogenated solvent, including but not limited to, dichloromethane, carbon tetrachloride, chloroform, and dichloroethane. In one embodiment, the reaction of step (b) is carried out in dichloromethane. In one embodiment, the reaction of step (b) is carried out in a dry polar organic solvent. In one embodiment, the reaction of step (b) is carried out in acetonitrile.

In one embodiment, the reaction of step (b) is carried out at a temperature of less than about 30° C. In one embodiment, the reaction of step (b) is carried out at a temperature of less than about 25° C. In one embodiment, the reaction of step (b) is carried out at a temperature of less than about 20° C. In one embodiment, the reaction of step (b) is carried out at a temperature of less than about 15° C. In one embodiment, the reaction of step (b) is carried out at a temperature of less than about 10° C. In one embodiment, the reaction of step (b) is carried out at a temperature of less than about 5° C. In one embodiment, the reaction of step (b) is carried out at a temperature of less than about 0° C. In one embodiment, the reaction of step (b) is carried out at a temperature of greater than about −20° C. In one embodiment, the reaction of step (b) is carried out at a temperature of greater than about −10° C. In one embodiment, the reaction of step (b) is carried out at a temperature of greater than about 0° C. In one embodiment, the reaction of step (b) is carried out at a temperature of between about 0° C. and about 5° C. In one embodiment, the reaction of step (b) is carried out at a temperature of between about −5° C. and about −10° C. In one embodiment, the reaction of step (b) is carried out at a temperature of between about −15° C. and about −20° C.

In one embodiment, the coupling reaction of step (b) is carried out under an inert atmosphere. In one embodiment, the coupling reaction is carried out under nitrogen. In one embodiment, the coupling reaction is carried out under argon.

The reaction time of the coupling reaction of step (b) can vary from about 1 hr to about 24 hr, depending on the reaction temperature, the reagents used, and the concentration of reagents in the reaction mixture. In general, the higher the reaction temperature, the shorter the reaction time, however, higher reaction temperature may give rise to side reactions or decomposition of the product. In specific embodiments, the reaction time of step (b) is about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, or about 24 hr. In certain embodiments, the reaction time is about 2 hr, about 3 hr, about 4 hr, about 5 hr, about 6 hr, about 7 hr, about 8 hr, about 9 hr, or about 10 hr, at a reaction temperature of between about 0° C. and about 5° C., when the Lewis acid is stannic chloride. In certain embodiments, the reaction time is about 2 hr, about 4 hr, about 6 hr, about 8 hr, about 10 hr, about 12 hr, about 14 hr, about 16 hr, about 18 hr, about 20 hr, about 22 hr, or about 24 hr, at a reaction temperature of between about 0° C. and about 5° C., when the Lewis acid is ferric chloride. In some embodiments, the progress of the reaction is monitored, such as by taking an aliquot of the reaction mixture, quenching it with an aqueous solution, and passing it through HPLC. In one embodiment, the reaction is quenched when the reaction is determined to be substantially complete, e.g., via reaction progress monitoring.

In one embodiment, the reaction of step (b) is performed by stirring the silylated 5-azacytosine with the acyl protected β-D-ribofuranose in a solvent maintained at a temperature of between about 0° C. and about 5° C.; adding the metallic Lewis acid, such as stannic chloride or ferric chloride, while maintaining the temperature of the reaction mixture; and stirring the reaction mixture at a temperature of between about 0° C. and about 5° C. until the reaction is substantially complete. In one embodiment, the reaction of step (b) is performed by stirring the acyl protected β-D-ribofuranose and the metallic Lewis acid, such as stannic chloride or ferric chloride, in a solvent maintained at a temperature of between about 0° C. and about 5° C.; adding the silylated 5-azacytosine while maintaining the temperature of the reactions mixture; and stirring the reaction mixture at a temperature of between about 0° C. and about 5° C. until the reaction is substantially complete.

In one embodiment, the molar ratio of the acyl protected β-D-ribofuranose used in the reaction of step (b) relative to 5-azacytosine used in step (a) is about 0.5 (i.e., [acyl protected β-D-ribofuranose]/[5-azacytosine]=0.5), about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0. In one embodiment, the molar ratio of the acyl protected β-D-ribofuranose used in the reaction of step (b) relative to 5-azacytosine used in step (a) is about 0.9. In one embodiment, the molar ratio of the acyl protected β-D-ribofuranose used in the reaction of step (b) relative to 5-azacytosine used in step (a) is about 1.0. In one embodiment, the molar ratio of the acyl protected β-D-ribofuranose used in the reaction of step (b) relative to 5-azacytosine used in step (a) is about 1.1.

In one embodiment, the molar ratio of the metallic Lewis acid used in the reaction of step (b) relative to 5-azacytosine used in step (a) is about 0.5 (i.e., [Lewis acid]/[5-azacytosine]=0.5), about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.5, about 3.0, or greater than about 3.0. In one embodiment, the molar ratio of the metallic Lewis acid used in the reaction of step (b) relative to 5-azacytosine used in step (a) is about 0.9. In one embodiment, the molar ratio of the metallic Lewis acid used in the reaction of step (b) relative to 5-azacytosine used in step (a) is about 1.0. In one embodiment, the molar ratio of the metallic Lewis acid used in the reaction of step (b) relative to 5-azacytosine used in step (a) is about 1.1. In one embodiment, the molar ratio of the metallic Lewis acid used in the reaction of step (b) relative to 5-azacytosine used in step (a) is about 1.5.

In one embodiment, the reaction of step (b) is quenched with water and one or more neutralizing reagents(s) to yield a quenched composition. In one embodiment, the reaction of step (b) is quenched at a temperature of about 15° C., about 10° C., about 5° C., or about 0° C. In one embodiment, the reaction of step (b) is quenched at a temperature of less than about 10° C. The quenching step may be exothermic. In one embodiment, the reaction mixture is cooled in a cooling bath. In one embodiment, water and one or more neutralizing reagent(s) are added slowly to the reaction mixture of step (b) to maintain the temperature of the reaction mixture. In one embodiment, water and the neutralizing reagent(s) are added together as a solution to the reaction mixture of step (b). In one embodiment, water and the neutralizing reagent(s) are added separately and sequentially. In one embodiment, water is chilled before addition to the reaction mixture of step (b). In one embodiment, an organic solvent is added to the reaction mixture of step (b) when the reaction is quenched, such organic solvent may be the same solvent used in the reaction, such as, for example, dichloromethane.

In one embodiment, the neutralizing reagent in step (b) is an inorganic reagent. In one embodiment, the neutralizing reagent in step (b) is an inorganic base, such as, for example, lithium hydroxide, sodium hydroxide, and potassium hydroxide. In one embodiment, the neutralizing reagent in step (b) is an inorganic salt, such as, for example, sodium carbonate, sodium bicarbonate, potassium carbonate, potassium bicarbonate, lithium carbonate, lithium bicarbonate, sodium phosphate, sodium hydrogenphosphate, sodium dihydrogenphosphate, potassium phosphate, potassium hydrogenphosphate, potassium dihydrogenphosphate, lithium phosphate, lithium hydrogenphosphate, lithium dihydrogenphosphate, sodium citrate, potassium citrate, and lithium citrate. In one embodiment, the neutralizing reagent in step (b) is a carbonate or bicarbonate salt, or a mixture thereof. In one embodiment, the neutralizing reagent in step (b) is sodium carbonate or sodium bicarbonate, or a mixture thereof. In one embodiment, the neutralizing reagent in step (b) is a mixture of sodium carbonate and sodium bicarbonate in 1:1 molar ratio. In one embodiment, the neutralizing reagent in step (b) is a mixture of sodium carbonate and sodium bicarbonate in 1:1 weight ratio. In one embodiment, the neutralizing reagent in step (b) is sodium carbonate. In one embodiment, the neutralizing reagent in step (b) is sodium bicarbonate. In one embodiment, the neutralizing reagent is first dissolved in water and the solution is added to the reaction mixture of step (b). In one embodiment, the neutralizing reagent is added to the reaction mixture of step (b) as a solid. In one embodiment, the neutralizing reagent is added first to the reaction mixture of step (b), and then water is added to the reaction mixture. In one embodiment, water is added first to the reaction mixture of step (b), and then the neutralizing reagent is added as a solid or a solution to the reaction mixture.

In one embodiment, the quenched composition is stirred for about 15 minutes, about 30 minutes, about 45 minutes, about 1 hour, about 1.5 hour, about 2 hour, or more than about 2 hour. In one embodiment the quenched composition is stirred at the temperature of about 15° C., about 10° C., about 5° C., or about 0° C. In one embodiment, the quenched composition is stirred at the temperature of less than about 10° C. In one embodiment, metallic oxide, such as, for example, stannic oxide or ferric oxide, settles to the bottom of the reaction vessel.

In one embodiment, the quenched composition of the reaction of step (b) is filtered. In one embodiment, the quenched composition of the reaction of step (b) is filtered through Hyflo Super Gel®. In one embodiment, the quenched composition of the reaction of step (b) is filtered through Celite®. In one embodiment, the filter cake is washed with an organic solvent, such as an organic non-polar solvent with low water solubility. In one embodiment, the quenching composition of the reaction of step (b) is filtered at a temperature of about 15° C., about 10° C., about 5° C., or about 0° C. In one embodiment, the quenching composition of the reaction of step (b) is filtered at a temperature of less than about 10° C.

In one embodiment, the filtrate of the quenched composition of the reaction of step (b) contains an organic phase and an aqueous phase. In one embodiment, the organic phase of the filtrate is separated from its aqueous phase, and the desired product generally presents in the organic phase. In one embodiment, the organic phase is further washed with water. In one embodiment, the filtrate (e.g., the organic phase of the filtrate) is washed with an aqueous EDTA (ethylenediaminetetraacetic acid) salt solution. In one embodiment, the filtrate is washed with an aqueous EDTA disodium salt solution, such as a 10% EDTA disodium salt solution. In one embodiment, the washing, extracting, and/or phase separation of the filtrate is carried out at a temperature of about 15° C., about 10° C., about 5° C., or about 0° C. In one embodiment, the washing, extracting, and/or phase separation of the filtrate is carried out at a temperature of less than about 10° C. In one embodiment, the filtrate (e.g., the organic phase of the filtrate) is dried over an anhydrous salt, such as, for example, anhydrous sodium sulfate or anhydrous magnesium sulfate. In one embodiment, the solvent of the filtrate is distilled off to afford the protected 5-azacytidine as a solid residue. In one embodiment, methanol is added to the solid residue of the protected 5-azacytidine to re-suspend the product, and the solvent of this mixture is then distilled off to form a solid residue of the protected 5-azacytidine. In certain embodiments, the solid residue of the protected 5-azacytidine is a crystalline solid. In one embodiment, the solvent of the filtrate used in extraction (e.g., dichloromethane) is partially distilled off to afford a concentrated solution of protected 5-azacytidine, followed by the addition of an alcohol, such as methanol, to the mixture, and followed by vacuum distillation to substantially remove the solvent (e.g., dichloromethane) and form a slurry of the protected 5-azacytidine in alcohol, such as methanol.

As described herein, the exposure of protected 5-azacytidine to water can be minimized by using a non-polar dry organic solvent for the coupling step. Alternatively, if a dry organic polar solvent is used in the coupling step, the solvent can be removed and replaced with a dry non-polar organic solvent prior to quenching. The quenching composition may be kept at a low temperature, such as less than about 10° C., to reduce the possibility of emulsion during aqueous extraction and the decomposition of the product during the work-up steps (e.g., quenching, filtration, and extraction).

In one embodiment, the protected 5-azacytidine of step (b) is a compound of formula (C):

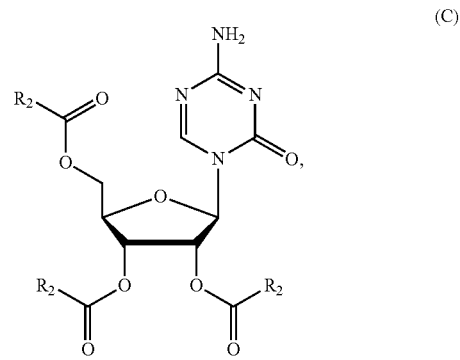

wherein $R_1$ and $R_2$ are defined herein elsewhere. In one embodiment, the protected 5-azacytidine is:

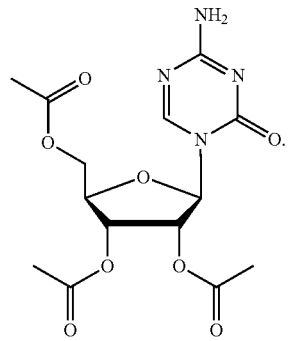

In one embodiment, the protected 5-azacytidine is obtained following steps (a) and (b), in about 25%, about 30%, about 35%, about 40%, about 45%, about 50%, about 55%, about 60%, about 65%, about 70%, about 75%, about 80%, about 85%, about 90%, about 95%, or about 99% yield. In one embodiment, the yield is calculated based on 5-azacytosine used in step (a).

3. Step (c)—Deprotection

In one embodiment, the base used in step (c) is alkoxide, ammonia, or tetra-substituted ammonium hydroxide. In one embodiment, the base used in step (c) is alkoxide. In one embodiment, the base used in step (c) is ammonia. In one embodiment, the base used in step (c) is tetra-substituted ammonium hydroxide, such as for example, benzyl trimethyl ammonium hydroxide. In one embodiment, the base used in step (c) is sodium alkoxide. In one embodiment, the base used in step (c) is sodium methoxide.

In one embodiment, the alcohol used in step (c) is methanol. In one embodiment, the alcohol used in step (c) is ethanol. In one embodiment, the alcohol used in step (c) is isopropanol.

In one embodiment, the reaction of step (c) is carried out at room temperature. In one embodiment, the reaction of step (c) is carried out at a temperature of about 20° C. In one embodiment, the reaction of step (c) is carried out at a temperature of about 25° C. In one embodiment, the reaction of step (c) is carried out at a temperature of about 30° C.

The reaction time of the deprotection reaction of step (c) can vary from about 1 hr to about 24 hr, depending on the reaction temperature, the base used, and the concentration of the reagents in the reaction mixture. In general, the higher the reaction temperature, the shorter the reaction time, however, higher reaction temperature may give rise to side reactions or decomposition of the product. In specific embodiments, the reaction time of step (c) is about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, or about 24 hr. In certain embodiments, the reaction time is about 6 hr, about 8 hr, about 10 hr, about 12 hr, about 14 hr, about 16 hr, about 18 hr, about 20 hr, about 22 hr, or about 24 hr at a reaction temperature of between about 25° C. and about 30° C. In some embodiments, the progress of the reaction is monitored, such as by taking an aliquot of the reaction mixture and passing it through HPLC. In one embodiment, the reaction is quenched when the reaction is determined to be substantially complete, e.g., via reaction progress monitoring.

In one embodiment, the reaction of step (c) is carried out under an inert atmosphere. In one embodiment, the reaction of step (c) is carried out under nitrogen. In one embodiment, the reaction of step (c) is carried out under argon.

In one embodiment, the reaction of step (c) is performed by stirring the protected 5-azacytidine in an alcohol, adding the base, and stirring the mixture at ambient temperature until the reaction is substantially complete. In one embodiment, the pH value of the reaction mixture is above about pH 10 after the base is added. In one embodiment, additional base is added until the pH value of the reaction mixture is above about pH 10.

In one embodiment, the 5-azacytidine of step (c) is collected by filtration. In one embodiment, the 5-azacytidine of step (c) is washed with a non-aqueous solvent, including but not limited to, an alcohol, such as methanol. In one embodiment, the 5-azacytidine of step (c) is dried under vacuum (e.g., 10-15 mmHg). In one embodiment, the 5-azacytidine of step (c) is dried at elevated temperature (e.g., about 60° C.) under vacuum (e.g., 10-15 mmHg).

In one embodiment, the 5-azacytidine is obtained following steps (a)-(c), in about 20%, about 25%, about 30%, about 35%, about 40%, about 45%, about 50%, about 55%, about 60%, about 65%, about 70%, about 75%, about 80%, about 85%, about 90%, about 95%, or about 99% yield. In one embodiment, the yield is calculated based on 5-azacytosine used in step (a).

4. Step (d)—Salt Formation

In one embodiment, the acid used for salt formation in step (d) is an organic acid or an inorganic acid, including, but not limited to, acid capable of forming a pharmaceutically acceptable salt. In specific embodiments, the acid includes, but is not limited to, hydrochloric acid, hydrobromic acid, sulfuric acid, and methanesulfonic acid. In some embodiments, the acid used in step (d) is hydrochloric acid.

In one embodiment, the organic solvent used in step (d) is methanol, ethanol, isopropanol, ethyl acetate, tetrahydrofuran, acetone, methyl ethyl ketone, diethyl ether, methyl t-butyl ether, acetonitrile, N-methyl pyrrolidinone, dimethylformamide, dimethyl sulfoxide, dichloromethane, or chloroform, or the like, or mixtures thereof. In one embodiment, the organic solvent in step (d) is an alcohol or a mixture thereof. In some embodiments, the organic solvent in step (d) is methanol. In some embodiments, the organic solvent in step (d) is ethanol. In some embodiments, the organic solvent in step (d) is isopropanol.

In one embodiment, the salt formation reaction of step (d) is performed by stirring 5-azacytidine in an organic solvent, adding an acid, and stirring the mixture at ambient temperature.

In one embodiment, a molar excess of acid (relative to 5-azacytidine) is used. In one embodiment, the molar ratio between the acid and 5-azacytidine is about 1:1.

In one embodiment, the reaction of step (d) is carried out at room temperature. In one embodiment, the reaction of step (d) is carried out at a temperature of about 20° C. In one embodiment, the reaction of step (d) is carried out at a temperature of about 25° C. In one embodiment, the reaction of step (d) is carried out at a temperature of about 30° C. In one embodiment, the reaction of step (d) is carried out at a temperature of less than about 25° C. In one embodiment, the reaction of step (d) is carried out at a temperature of between about 25° C. and about 30° C.

In one embodiment, the reaction of step (d) is carried out under an inert atmosphere. In one embodiment, the reaction of step (d) is carried out under nitrogen. In one embodiment, the reaction of step (d) is carried out under argon.

In one embodiment, the reaction time of the reaction of step (d) can vary from about 0.5 hr to about 24 hr. In one embodiment, the reaction time is about 0.5 hr, about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, or about 24 hr. In one embodiment, the reaction time is about 1 hr. In one embodiment, the reaction time is about 2 hr. In one embodiment, the reaction time is about 3 hr. In one embodiment, the reaction time is about 4 hr. In some embodiments, the reaction mass first becomes a clear solution and then becomes a suspension, wherein the salt is crystallized from the reaction mass. In one embodiment, the reaction mixture of step (d) is cooled to a temperature of less than about 20° C., less than about 15° C., less than about 10° C., or less than about 5° C., to facilitate the crystallization of the salt.

In one embodiment, the salt of 5-azacytidine of step (d) is collected by filtration. In one embodiment, the salt of 5-azacytidine of step (d) is washed with an organic solvent, including but not limited to, an alcohol, such as methanol.

In one embodiment, the salt of 5-azacytidine of step (d) is isolated by concentrating the reaction mixture of step (d), followed by filtration. In one embodiment, the salt of 5-azacytidine of step (d) is isolated by concentrating the reaction mixture of step (d) under vacuum (e.g., 10-15 mmHg) to remove volatile solvent.

In one embodiment, the salt of 5-azacytidine of step (d) is dried under vacuum (e.g., 10-15 mmHg). In one embodiment, the salt of 5-azacytidine of step (d) is dried under vacuum (e.g., 10-15 mmHg) at an elevated temperature (e.g., about 50° C., or about 60° C.).

In one embodiment, a salt of 5-azacytidine is obtained following step (d), in about 20%, about 25%, about 30%, about 35%, about 40%, about 45%, about 50%, about 55%, about 60%, about 65%, about 70%, about 75%, about 80%, about 85%, about 90%, about 95%, about 99%, or about 99.9% yield. In one embodiment, the yield is calculated based on 5-azacytidine used in the salt formation reaction.

In one embodiment, the salt of 5-azacytidine obtained from step (d) is substantially pure. In one embodiment, the salt of 5-azacytidine obtained from step (d) is substantially physically pure. In one embodiment, the salt of 5-azacytidine obtained from step (d) is substantially chemically pure. In one embodiment, the salt of 5-azacytidine obtained from step (d) is substantially free of impurities, such as, e.g., a metal-based impurity. In one embodiment, the salt of 5-azacytidine from step (d) is obtained as a crystalline material that is substantially chemically and/or physically pure.

In one embodiment, the chemical purity of the salt of 5-azacytidine obtained from step (d) is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the physical purity of the salt of 5-azacytidine obtained from step (d) is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the total metal-based impurities in the salt of 5-azacytidine obtained from step (d) is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch. In one embodiment, an individual metal based impurity, such as for example, tin or iron content, in the salt of 5-azacytidine obtained from step (d) is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, less than about 0.1 ppm w/w, less than about 0.05 ppm w/w, less than about 0.02 ppm w/w, or less than about 0.01 ppm w/w relative to the total batch.

5. Step (e)—Free Base Formation

In one embodiment, the base used to form the 5-azacytidine free base in step (e) is an organic base or an inorganic base. In one embodiment, the base used in step (e) is an organic base, including but not limited to, triethylamine, diisopropylethyl amine, pyridine, diisopropylamine, 2,6-lutidine, N-methylmorpholine, N,N-dicyclohexylmethyl amine, and the like. In some embodiments, the base in step (e) is triethylamine.

In one embodiment, the organic solvent used in step (e) is methanol, ethanol, isopropanol, ethyl acetate, tetrahydrofuran, acetone, methyl ethyl ketone, diethyl ether, methyl t-butyl ether, acetonitrile, N-methyl pyrrolidinone, dimethylformamide, dimethyl sulfoxide, dichloromethane, or chloroform, or the like, or mixtures thereof. In one embodiment, the organic solvent in step (e) is alcohol or a mixture thereof. In some embodiments, the organic solvent in step (e) is methanol. In some embodiments, the organic solvent in step (e) is ethanol. In some embodiments, the organic solvent in step (e) is isopropanol.

In one embodiment, the free base formation reaction of step (e) is performed by stirring a salt of 5-azacytidine in an organic solvent, adding a base, and stirring the mixture at ambient temperature.

In one embodiment, a molar excess of base (relative to 5-azacytidine) is used. In one embodiment, the molar ratio between the base and 5-azacytidine is about 1:1.

In one embodiment, the reaction of step (e) is carried out at room temperature. In one embodiment, the reaction of step (e) is carried out at a temperature of about 20° C. In one embodiment, the reaction of step (e) is carried out at a temperature of about 25° C. In one embodiment, the reaction of step (e) is carried out at a temperature of about 30° C. In one embodiment, the reaction of step (e) is carried out at a temperature of less than about 30° C. In one embodiment, the reaction of step (e) is carried out at a temperature of between about 25° C. and about 30° C.

In one embodiment, the reaction of step (e) is carried out under an inert atmosphere. In one embodiment, the reaction of step (e) is carried out under nitrogen. In one embodiment, the reaction of step (e) is carried out under argon.

In one embodiment, the reaction time of the reaction of step (e) can vary from about 0.5 hr to about 24 hr. In one embodiment, the reaction time is about 0.5 hr, about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, or about 24 hr. In one embodiment, the reaction time is about 1 hr. In one embodiment, the reaction time is about 2 hr. In one embodiment, the reaction time is about 3 hr. In one embodiment, the reaction time is about 4 hr. In some embodiments, the reaction mass is stirred as a slurry upon formation of the free base of 5-azacytidine. In one embodiment, the reaction mixture of step (e) is cooled to a temperature of less than about 20° C., less than about 15° C., less than about 10° C., or less than about 5° C., before it is filtered.

In one embodiment, the free base of 5-azacytidine of step (e) is collected by filtration. In one embodiment, the free base of 5-azacytidine of step (e) is washed with an organic solvent, such as for example, an alcohol, such as methanol. In one embodiment, the washing is continued until the free base of 5-azacytidine of step (e) is substantially free of impurities, such as for example, the acid addition salt counter ion (such as, e.g., chloride). In one embodiment, the free base of 5-azacytidine of step (e) is substantially free of impurities, including but not limited to, metal-based impurity and acid addition salt counter ion.

In one embodiment, the free base of 5-azacytidine of step (e) is dried under vacuum (e.g. 10-15 mmHg). In one embodiment, the free base of 5-azacytidine of step (e) is dried under vacuum (e.g. 10-15 mmHg) at an elevated temperature (e.g. about 50° C., or about 60° C.).

In one embodiment, a free base of 5-azacytidine is obtained following step (e), in about 20%, about 25%, about 30%, about 35%, about 40%, about 45%, about 50%, about 55%, about 60%, about 65%, about 70%, about 75%, about 80%, about 85%, about 90%, about 95%, about 99%, or about 99.9% yield. In one embodiment, the yield is calculated based on the salt of 5-azacytidine used.

In one embodiment, the free base of 5-azacytidine obtained from step (e) is substantially pure. In one embodiment, the free base of 5-azacytidine obtained from step (e) is substantially physically pure. In one embodiment, the free base of 5-azacytidine obtained from step (e) is substantially chemically pure. In one embodiment, the free base of 5-azacytidine obtained from step (e) is substantially free of impurities, such as, e.g., a metal-based impurity and/or acid addition salt counter ion. In one embodiment, the free base of 5-azacytidine from step (e) is obtained as a crystalline material that is substantially chemically and/or physically pure.

In one embodiment, the chemical purity of the free base of 5-azacytidine obtained from step (e) is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the physical purity of the free base of 5-azacytidine obtained from step (e) is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the total metal-based impurities in the free base of 5-azacytidine obtained from step (e) is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch. In one embodiment, an individual metal based impurity, such as for example, tin or iron content, in the free base of 5-azacytidine obtained from step (e) is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, less than about 0.1 ppm w/w, less than about 0.05 ppm w/w, less than about 0.02 ppm w/w, or less than about 0.01 ppm w/w relative to the total batch.

6. Step (f)—Re-Crystallization

In one embodiment, step (f) comprises the steps of:
(1) dissolving 5-azacytidine free base from step (e) in dimethylsulfoxide at a temperature sufficient to allow the 5-azacytidine to dissolve; and optionally filtering the solution to remove insoluble particles;
(2) adding an anti-solvent to the solution of step (1); and
(3) cooling the mixture of step (2) wherein 5-azacytidine re-crystallizes.

In one embodiment, 5-azacytidine is dissolved in dimethylsulfoxide (DMSO) in step (f)(1) at an elevated temperature, such as for example, at a temperature of about 40° C., about 45° C., about 50° C., about 55° C., about 60° C., about 65° C., about 70° C., about 75° C., about 80° C., about 85° C., about 90° C., about 95° C., or about 100° C. In one embodiment, the optional filtration in step (f)(1) is carried out at an elevated temperature, such as for example, at a temperature of about 40° C., about 45° C., about 50° C., about 55° C., about 60° C., about 65° C., about 70° C., about 75° C., about 80° C., about 85° C., about 90° C., about 95° C., or about 100° C. In one embodiment, optionally, the insoluble particles are washed with hot DMSO.

In one embodiment, the anti-solvent of step (f)(2) is an alcohol. In one embodiment, the anti-solvent of step (f)(2) is methanol. In one embodiment, the anti-solvent is added slowly to the 5-azacytidine DMSO solution, at a temperature of about 40° C., about 45° C., about 50° C., about 55° C., about 60° C., about 65° C., about 70° C., about 75° C., about 80° C., or about 85° C. In one embodiment, the anti-solvent is methanol, which is added slowed to the 5-azacytidine DMSO solution at a temperature of between about 70° C. and about 80° C., between about 60° C. and about 70° C., between about 50° C. and about 60° C., between about 40° C. and about 50° C., or between about 30° C. and about 40° C.

In one embodiment, the mixture of step (f)(3) is cooled to a temperature of about 35° C., about 30° C., about 25° C., about 20° C., about 15° C., about 10° C., about 5° C. or about 0° C. In one embodiment, the mixture of step (f)(3) is cooled to a temperature of between about 25° C. and about 30° C. In one embodiment, the mixture of step (f)(3) is cooled slowly over a period of about 1 hr, about 2 hr, about 3 hr, about 4 hr, about 5 hr, about 6 hr, about 7 hr, about 8 hr, about 9 hr, about 10 hr, about 11 hr, or about 12 hr. In one embodiment, after cooling, the mixture of step (f)(3) is stirred for a period of about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In one embodiment, after cooling the mixture to a temperature of between about 25° C. and about 30° C., the mixture is stirred for about 15 hr at a temperature of between about 25° C. and about 30° C.

In specific embodiments, precipitation of the 5-azacytidine is induced upon anti-solvent addition. In specific embodiments, precipitation is induced upon cooling. In specific embodiments, precipitation is induced by both anti-solvent addition and cooling.

In one embodiment, step (f)(1) is carried out under an inert atmosphere. In one embodiment, step (f)(2) is carried out under an inert atmosphere. In one embodiment, step (f)(3) is carried out under an inert atmosphere.

In one embodiment, step (f) further comprises the steps of:
(4) collecting the re-crystallized 5-azacytidine from step (3) by filtration; and
(5) drying the 5-azacytidine from step (4) under vacuum.

In one embodiment, the filtration of step (f)(4) is carried under an inert atmosphere. In one embodiment, the solid product is washed with a solvent, such as, methanol. In one embodiment, the solid product is washed with a solvent, which is the same solvent used at the anti-solvent in step (f)(2).

In one embodiment, the solid product is dried under vacuum (e.g. 10-15 mmHg). In one embodiment, the drying is carried out at room temperature. In one embodiment, the drying the carried out at an elevated temperature, for example, about 40° C., about 45° C., about 50° C., about 55° C., about 60° C., about 65° C., about 70° C., about 75° C., about 80° C., about 85° C., about 90° C., about 95° C., or about 100° C. In one embodiment, the drying the carried out at a temperature of between about 85° C. and about 90° C. In one embodiment, the drying is continued until the weight loss on drying falls below about 0.4% w/w. In one embodiment, the drying is carried out over a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, about 24 hr, about 36 hr, about 48 hr, about 60 hr, or about 72 hr.

In one embodiment, the re-crystallized 5-azacytidine is obtained following step (f), in about 25%, about 30%, about 35%, about 40%, about 45%, about 50%, about 55%, about 60%, about 65%, about 70%, about 75%, about 80%, about 85%, about 90%, about 95%, about 99%, or about 99.9% yield. In one embodiment, the yield is calculated based on the 5-azacytidine used for re-crystallization.

7. Additional Embodiments

In one embodiment, 5-azacytosine is first reacted with HMDS in the presence of ammonium sulfate to afford a silylated 5-azacytosine, which is coupled with 1,2,3,5-tetra-O-acetyl-β-D-ribofuranose in the presence of stannic chloride ($SnCl_4$) to afford the tri-acetyl protected 5-azacytidine. In some embodiments, the chemical and/or physical purity of the tri-acetyl protected coupling product is greater than about 50% w/w, greater than about 60% w/w, greater than about 70% w/w, greater than about 80% w/w, greater than about 90% w/w, or greater than about 95% w/w. In one embodiment, the chemical and/or physical purity of the tri-acetyl protected coupling product is greater than about 75% w/w. In some embodiments, the yield of the coupling reaction is between about 50% and about 99%, between about 60% and about 90%, between about 60% and about 80%, or between about 65% and about 75% (yield is based on chemical purity of the crude product). In one embodiment, the yield of the coupling reaction is about 70% (yield is based on chemical purity of the crude product).

In another embodiment, 5-azacytosine is first reacted with HMDS in the presence of ammonium sulfate to afford a silylated 5-azacytosine, which is coupled with 1,2,3,5-tetra-O-acetyl-β-D-ribofuranose in the presence of ferric chloride ($FeCl_3$) to afford the tri-acetyl protected 5-azacytidine. In some embodiments, the chemical and/or physical purity of the tri-acetyl protected coupling product is greater than about 40% w/w, greater than about 50% w/w, greater than about 60% w/w, greater than about 70% w/w, greater than about 80% w/w, or greater than about 90% w/w. In one embodiment, the chemical and/or physical purity of the tri-acetyl protected coupling product is greater than about 60% w/w. In some embodiments, the yield of the coupling reaction is between about 30% and about 99%, between about 40% and about 90%, between about 40% and about 80%, between about 40% and about 70%, between about 40% and about 60%, or between about 45% and about 55% (yield is based on chemical purity of the crude product). In one embodiment, the yield of the coupling reaction is about 50% (yield is based on chemical purity of the crude product).

In one embodiment, the acetyl protected 5-azacytidine is deacetylated with sodium methoxide solution in methanol to afford a crude product of 5-azacytidine. In some embodiments, the chemical and/or physical purity of the crude 5-azacytidine is greater than about 80% w/w, greater than about 90% w/w, greater than about 95% w/w, or greater than about 99% w/w, when $SnCl_4$ is used as the Lewis acid in the preceding coupling step. In one embodiment, the chemical and/or physical purity of the crude 5-azacytidine is greater than about 95% w/w, when $SnCl_4$ is used as the Lewis acid in the preceding coupling step. In other embodiments, the chemical and/or physical purity of the crude 5-azacytidine is greater than about 80% w/w, greater than about 90% w/w, greater than about 95% w/w, or greater than about 99% w/w, when $FeCl_3$ is used as the Lewis acid in the preceding coupling step. In one embodiment, the chemical and/or physical purity of the crude 5-azacytidine is greater than about 90% w/w, when $FeCl_3$ is used as the Lewis acid in the preceding coupling step. In some embodiments, the combined yield of the coupling step and the deprotection step is between about 40% and about 90%, between about 50% and about 75%, or between about 55% and about 65%, when $SnCl_4$ is used as the Lewis acid (yield is based on 5-azacytosine). In one embodiment, the combined yield of the coupling step and the deprotection step is about 60%, when $SnCl_4$ is used as the Lewis acid (yield is based on 5-azacytosine). In other embodiments, the combined yield of the coupling step and the deprotection step is between about 20% and about 80%, between about 30% and about 65%, or between about 35% and about 45%, when $FeCl_3$ is used as the Lewis acid (yield is based on 5-azacytosine). In one embodiment, the combined yield of the coupling step and the deprotection step is about 40%, when $FeCl_3$ is used as the Lewis acid (yield is based on 5-azacytosine).

In one embodiment, the crude 5-azacytidine is treated with isopropanol-HCl (IPA-HCl) in methanol to form 5-azacytidine HCl salt. In some embodiments, the chemical and/or physical purity of the 5-azacytidine HCl salt is greater than about 90% w/w, greater than about 92% w/w, greater than about 94% w/w, greater than about 96% w/w, greater than about 98% w/w, greater than about 99% w/w, or greater than about 99.5% w/w. In one embodiment, the chemical and/or physical purity of the 5-azacytidine HCl salt is greater than about 98% w/w. In some embodiments, the yield of the salt formation step is about 60%, about 70%, about 80%, about 90%, about 95%, or about 99%, when $SnCl_4$ is used as the Lewis acid in the preceding coupling step. In one embodiment, the yield of the salt formation step is about 80%, when $SnCl_4$ is used as the Lewis acid in the preceding coupling step. In other embodiments, the yield of the salt formation step is about 50%, about 60%, about 70%, about 80%, about 90%, or about 95%, when $FeCl_3$ is used as the Lewis acid in the preceding coupling step. In one embodiment, the yield of the salt formation step is about 72%, when $FeCl_3$ is used as the Lewis acid in the preceding coupling step.

In one embodiment, the 5-azacytidine HCl salt is treated with triethylamine in the presence of methanol to afford the free base of 5-azacytidine. In some embodiments, the chemical and/or physical purity of the 5-azacytidine free base is greater than about 90% w/w, greater than about 95% w/w, greater than about 98% w/w, greater than about 99% w/w, greater than about 99.5% w/w, or greater than about 99.9% w/w. In one embodiment, the chemical and/or physical purity of the 5-azacytidine free base is greater than about 99% w/w. In some embodiments, the yield of the free base formation step is about 70%, about 80%, about 90%, about 95%, about 98%, or about 99%, when $SnCl_4$ is used as the Lewis acid in the preceding coupling step. In one embodiment, the yield of the free base formation step is about 95%, when $SnCl_4$ is used as the Lewis acid in the preceding coupling step. In other embodiments, the yield of the salt formation step is about 70%, about 80%, about 90%, about 95%, about 98%, or about 99%, when $FeCl_3$ is used as the Lewis acid in the preceding coupling step. In one embodiment, the yield of the salt formation step is about 99%, when FeCl$_3$ is used as the Lewis acid in the preceding coupling step.

In one embodiment, the 5-azacytidine free base is re-crystallized in DMSO and methanol to afford 5-azacytidine as the final product. In some embodiments, the chemical and/or physical purity of the 5-azacytidine final product is greater than about 90% w/w, greater than about 95% w/w, greater than about 98% w/w, greater than about 99% w/w, greater than about 99.5% w/w, greater than about 99.8% w/w, or greater than about 99.9% w/w. In one embodiment, the chemical and/or physical purity of the 5-azacytidine final product is greater than about 99% w/w. In some embodiments, the yield of the re-crystallization step is about 70%, about 80%, about 85%, about 90%, about 95%, or about 99%, when SnCl$_4$ is used as the Lewis acid in the preceding coupling step. In one embodiment, the yield of the re-crystallization step is about 94%, when SnCl$_4$ is used as the Lewis acid in the preceding coupling step. In other embodiments, the yield of the re-crystallization step is about 70%, about 80%, about 85%, about 90%, about 95%, or about 99%, when FeCl$_3$ is used as the Lewis acid in the preceding coupling step. In one embodiment, the yield of the re-crystallization step is about 85%, when FeCl$_3$ is used as the Lewis acid in the preceding coupling step.

In one embodiment, provided herein is a process of preparing isotopically labeled 5-azacytidine, wherein the process uses one or more isotopically labeled starting material. In certain embodiments, a deuterium labeled starting material is used. In certain embodiments, a tritium labeled starting material is used. In certain embodiments, a $^{13}$C labeled starting material is used. In certain embodiments, a $^{15}$N labeled starting material is used. In certain embodiments, a $^{17}$O labeled starting material is used. In certain embodiments, the isotopically labeled starting material has two or more isotopic labels, including, but not limited to, deuterium, tritium, $^{13}$C, $^{15}$N and/or $^{17}$O labels. In certain embodiments, provided herein is a process to prepare 5-azacytidine with one or more isotopic label(s), including, but not limited to, deuterium, tritium, $^{13}$C, $^{15}$N, and/or $^{17}$O labels. In one embodiment, the isotopically labeled 5-azacytidine is substantially chemically and/or physically pure. In certain embodiments, at least one isotopically labeled starting material is used in step (a). In certain embodiments, at least one isotopically labeled starting material is used in step (b).

C. Salts of 5-Azacytidine

In one embodiment, provided herein are acid addition salts of 5-azacytidine, wherein the acid used in the preparation of the 5-azacytidine salt is an organic acid or an inorganic acid, including, but not limited to, hydrochloric acid, hydrobromic acid, sulfuric acid, and methanesulfonic acid. In one embodiment, provided herein is a salt of 5-azacytidine, including, but not limited to hydrochloride salt, hydrobromide salt, sulfate salt (including, e.g., bisulfate salt and hemisulfate salt), and methanesulfonate salt (i.e., mesylate salt). In one embodiment, provided herein is 5-azacytidine hemisulfate salt. In one embodiment, provided herein is 5-azacytidine mono-hydrochloride salt. In one embodiment, provided herein is 5-azacytidine mono-hydrobromide salt. In one embodiment, provided herein is 5-azacytidine hemisulfate salt, which is solvated with methanol. In one embodiment, the 5-azacytidine hemisulfate salt is solvated with methanol and the molar ratio of 5-azacytidine and methanol is about 1:1. In one embodiment, provided herein is 5-azacytidine mesylate salt, which is solvated with methanol. In one embodiment, the 5-azacytidine mesylate salt is solvated with methanol and the molar ratio of 5-azacytidine and methanol is about 1:1. In one embodiment, provided herein is a salt or solvate of 5-azacytidine that is substantially chemically and/or physically pure. In one embodiment, provided herein is a salt or solvate of 5-azacytidine that is substantially free of one or more impurities, such as for example, a metal-based impurity.

In one embodiment, provided herein is a pharmaceutically acceptable salt of 5-azacytidine, including, but not limited to hydrochloric acid salt, hydrobromic acid salt, sulfuric acid salt, and methanesulfonic acid salt. In one embodiment, provided herein is a pharmaceutically acceptable salt of 5-azacytidine that is substantially chemically and/or physically pure. In one embodiment, provided herein is a pharmaceutically acceptable salt of 5-azacytidine that is substantially free of one or more impurities.

In one embodiment, provided herein is a mono-hydrochloride salt of 5-azacytidine that is substantially chemically and/or physically pure. In one embodiment, provided herein is a 5-azacytidine mono-hydrochloride salt that is substantially free of one or more impurities. In specific embodiments, the 5-azacytidine mono-hydrochloride salt is substantially pure. In one embodiment, the 5-azacytidine mono-hydrochloride salt is substantially physically pure. In one embodiment, the 5-azacytidine mono-hydrochloride salt is substantially chemically pure.

In one embodiment, the chemical and/or physical purity of the 5-azacytidine mono-hydrochloride salt is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w. In one embodiment, the total impurities in the 5-azacytidine mono-hydrochloride salt is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w. In one embodiment, an individual impurity component in the 5-azacytidine mono-hydrochloride salt is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w. In one embodiment, the total metal-based impurities in the 5-azacytidine mono-hydrochloride salt is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w. In one embodiment, an individual metal based impurity, such as for example, tin or iron content, in the 5-azacytidine mono-hydrochloride salt is less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, less than about 0.1 ppm w/w, less than about 0.05 ppm w/w, less than about 0.02 ppm w/w, or less than about 0.01 ppm w/w.

In one embodiment, provided herein is a free base of 5-azacytidine having any three, four, five, six, seven, eight, nine, ten, eleven, twelve, thirteen, fourteen, or fifteen of the peaks as listed in Table 18 or Table 20 below.

In one embodiment, provided herein is a mono-hydrochloride salt of 5-azacytidine having any three, four, five, six, seven, eight, nine, ten, eleven, twelve, thirteen, fourteen, or fifteen of the peaks as listed in Table 24 or Table 26 below.

In one embodiment, provided herein is a sulfate salt of 5-azacytidine (e.g., hemisulfate salt) having any three, four, five, six, seven, eight, nine, ten, eleven, twelve, thirteen, fourteen, or fifteen of the peaks as listed in Table 28 below.

In one embodiment, provided herein is a mesylate salt of 5-azacytidine having any three, four, five, six, seven, eight, nine, ten, eleven, twelve, thirteen, fourteen, or fifteen of the peaks as listed in Table 30 below.

In one embodiment, provided herein is a hydrobromide salt of 5-azacytidine having any three, four, five, six, seven, eight, nine, ten, eleven, twelve, thirteen, fourteen, or fifteen of the peaks as listed in Table 32 below.

Also provided herein is a method for preparing an acid addition salt of 5-azacytidine, comprising mixing 5-azacytidine with an acid in an organic solvent, and isolating the salt of 5-azacytidine.

In one embodiment, the 5-azacytidine free base used for salt formation is prepared using the processes described herein. In other embodiments, the 5-azacytidine used for salt formation is obtained from a commercial source. In other embodiments, the 5-azacytidine used for salt formation is prepared following a literature procedure.

In one embodiment, 5-azacytidine is mixed with an acid in a molar ratio of about 1:1. In other embodiments, excess acid is used to form the 5-azacytidine salt.

In one embodiment, the acid used for salt formation is an organic acid or an inorganic acid, wherein examples of organic acids and inorganic acids are provided herein elsewhere. Non-limiting examples of suitable acids include methanesulfonic acid, trifluoroacetic acid, p-toluenesulfonic acid, hydrochoric acid, hydrobromic acid, nitric acid, sulfuric acid, and phosphoric acid.

In one embodiment, the organic solvent used in making a salt of 5-azacytidine is methanol, ethanol, isopropanol, ethyl acetate, tetrahydrofuran, acetone, methyl ethyl ketone, diethyl ether, methyl t-butyl ether, acetonitrile, N-methyl pyrrolidinone, dimethyl sulfoxide, dimethylformamide, dichloromethane, or chloroform, or a combination of one or more thereof. In one embodiment, the organic solvent used for salt formation is an alcohol, such as for example, methanol, ethanol, and isopropanol, or a mixture of one or more thereof. In one embodiment, the organic solvent used for salt formation is methanol.

In one embodiment, the salt of 5-azacytidine is formed by stirring 5-azacytidine in an organic solvent system, adding an acid, and stirring the mixture at ambient temperature. In one embodiment, the salt formation reaction is carried out under an inert atmosphere. In one embodiment, the salt of 5-azacytidine is collected by filtration. In one embodiment, the salt of 5-azacytidine is washed with an organic solvent, such as methanol. In one embodiment, the salt of 5-azacytidine is isolated by concentrating the mixture containing the 5-azacytidine salt (obtained as described above) under vacuum (e.g. 10-15 mmHg) to remove volatile solvent, and isolating the salt by filtration.

In one embodiment, the salt of 5-azacytidine is dried under vacuum (e.g. 10-15 mmHg). In one embodiment, the salt of 5-azacytidine of step (d) is dried under vacuum (e.g. 10-15 mmHg) at an elevated temperature (e.g. about 50° C., or about 60° C.).

VI. EXAMPLES

Certain embodiments are illustrated by the following non-limiting examples.

In the examples below, unless otherwise indicated, all temperatures are set forth in degrees Celsius and all parts and percentages are by weight. Reagents may be purchased from commercial suppliers, such as, e.g., Sigma-Aldrich® Chemical Co., and may be used without further purification unless otherwise indicated. Reagents may also be prepared following standard literature procedures known to those skilled in the art. Solvents may be purchased, for example, from Sigma-Aldrich®, and may be used as received or may be purified using standard methods known to those skilled in the art, unless otherwise indicated.

Unless otherwise specified, the reactions set forth below were done generally at ambient temperature. Reactions were assayed by HPLC, and terminated as judged by the consumption of starting material.

The compound structures and purities in the examples below were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, and/or HPLC. $^1$H NMR spectra were determined using a NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents as follows: $CDCl_3$=7.25 ppm; $DMSO$-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

A. The Stannic Chloride Route

1. Preparation of Silylated 5-Azacytosine

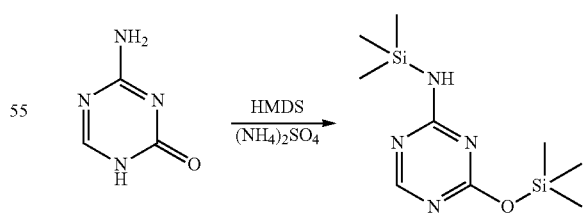

5-Azacytosine (100.0 g, 0.8921 mol, purity ≥98%) and hexamethyldisilazane (HMDS) (700.0 mL, 541.8 g, 3.3568 mol, purity ≥98%) were charged into a 3-L 4-neck round bottom flask at 25-30° C. under nitrogen atmosphere. Ammonium sulfate (5.0 g, 0.0378 mol) was added. The mixture was gradually heated to reflux at 125-130° C. The reflux was maintained for 6 hours. Typically, the reaction mass became a clear solution after 2-4 hours (e.g., about 3 hours), and the reaction was complete as soon as a clear solution was formed.

The reaction mass was gradually cooled to 40-50° C. HMDS was distilled off at 40-50° C. under vacuum (10-15 mmHg) to give a white solid. Nitrogen was used to break the vacuum over the solid. Toluene (200.0 mL) was added to the residue at 25-30° C., and the solvent was distilled off at 40-50° C. under vacuum (10-15 mmHg) to yield a solid. Nitrogen was used to break the vacuum over the solid. The solid was gradually cooled to 25-30° C., and carried through to the next step. HMDS was recovered in 75-80% yield with a purity of 90-95%.

The silylation reaction was also performed using 4, 5, 7, 10, and 14 volumes of HMDS (e.g., 400, 500, 700, 1000, or 1400 mL HMDS to 100 g 5-azacytosine).

2. Preparation of Acetyl-Protected 5-Azacytidine (Coupling)

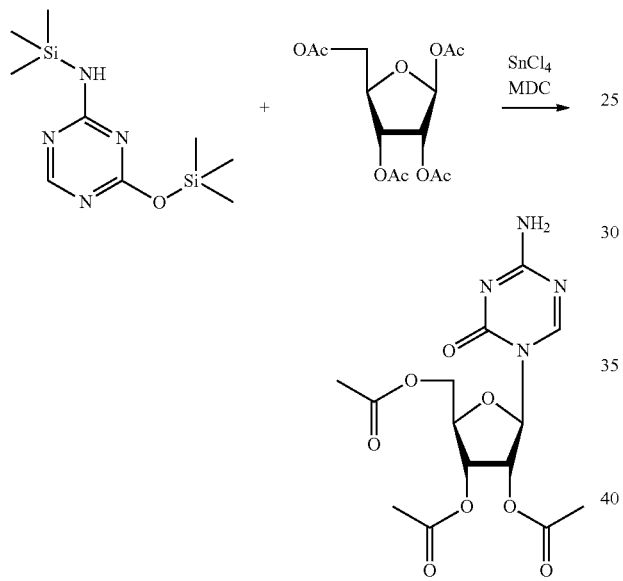

To silylated 5-azacytosine (Example A-1) was added dichloromethane (1.5 L). The mixture was stirred for 10 minutes under nitrogen atmosphere at 25-30° C. to obtain a clear solution. The solution was gradually cooled to 0-5° C. 1,2,3,5-Tetra-O-acetyl-β-D-ribofuranose (255.5 g, 0.8029 mol) was added in one lot at 0-5° C. under nitrogen atmosphere. The mixture was stirred for 10 minutes at 0-5° C. to obtain a clear solution. Stannic chloride (255.6 g, 0.9813 mol) was added drop-wise (addition was slightly exothermic) at ≤10° C. over a period of 1 hour. The reaction mass was stirred for 5 hours at 0-5° C. under nitrogen atmosphere.

The progress of the reaction was checked by HPLC. 5 g of reaction mass was withdrawn and neutralized with saturated aqueous NaHCO₃ solution at 10° C. The dichloromethane layer was separated and submitted for IPC-HPLC (In-Process-Control-HPLC). Once IPC had been met (5-azacytosine no more than 0.5% by HPLC), the reaction mass was transferred to a 5-L round bottom flask for work up.

To the reaction mass was added dichloromethane (1.0 L) and sodium bicarbonate (800.0 g) at ≤10° C. Chilled water (1.0 L) was added drop-wise (exothermic) at ≤10° C. over 30 minutes. The mixture was stirred for 30 minutes at ≤10° C.

After 15-30 minutes, a white solid (tin oxide) settled at the bottom of the flask. The mixture was filtered through Hyflo®, and washed with dichloromethane (0.5 L). The organic layer was separated at ≤10° C., and washed with water (0.75 L) at ≤10° C. The organic layer was washed with 10% EDTA disodium salt solution twice (150.0 g salt, 2×750 mL) and water once (1.0 L) at ≤10° C. The organic layer was dried over anhydrous sodium sulfate, and the solvent was distilled off at 40-45° C. under atmospheric conditions, and further dried at 40-45° C. under vacuum (10-15 mmHg) to give a sticky foaming solid. To the residue was added methanol (200.0 mL) at 30-35° C. The solvent was then distilled off at 40-45° C. under vacuum (10-15 mmHg), and degassed under vacuum for 30 minutes to afford 2',3',5'-triacetyl-5-azacytidine as a solid (315.0 g, white to off-white crystalline solid). The average output of 2',3',5'-triacetyl-5-azacytidine over multiple runs was about 305.2 g, with an average purity of about 83.7%, and an average yield of about 77.2% (% yield takes into account the HPLC purity of the product). Over five runs, the maximum yield of 2',3',5'-triacetyl-5-azacytidine was about 81.5% (% yield takes into account the HPLC purity of the product). Over five runs, the maximum HPLC purity of the product was about 87.8%.

3. Preparation of 5-Azacytidine (Deprotection)

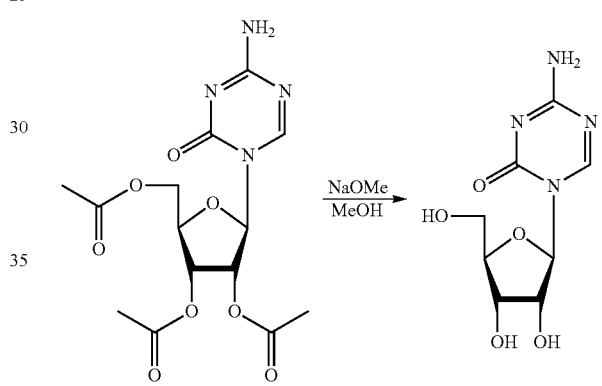

To 2',3',5'-triacetyl-5-azacytidine (315.0 g, Example A-2) was added methanol (2.0 L) at 25-30° C. The slurry was stirred for 10 minutes at 25-30° C., and 25% sodium methoxide in methanol (40.0 mL) was added slowly at 25-30° C. under nitrogen atmosphere. After addition, the reaction mass became a clear solution and the product immediately formed. The pH value of the reaction mass was above 10. The reaction mass was stirred for 18 hours at 25-30° C.

The progress of the reaction was checked by HPLC. A sample of the reaction mass was withdrawn and submitted for IPC-HPLC. Once IPC had been met (IPC-HPLC: 2',3',5'-triacetylazacitidine ≤0.5%), the product was filtered under nitrogen, and washed with methanol (300.0 mL) at 25-30° C. The product was dried at 60-65° C. under vacuum (10-15 mmHg) to give a white to off-white crystalline solid (144.8 g). The average output of 5-azacytidine over multiple runs was about 141.3 g, with an average purity of about 96.8%, and an average yield of about 64.8% (yield based on 5-azacytosine). Over five runs, the maximum yield of 5-azacytidine was about 73.2% (yield based on 5-azacytosine). Over five runs, the maximum HPLC purity of the product was about 98.83%.

4. Reaction Development (Coupling and Deprotection Steps)

The reaction conditions for the coupling and the deprotection steps were optimized by varying a number of parameters. The results are summarized in Table 1 below. Inexpensive and commercially readily available metallic Lewis acids, such as stannic chloride and ferric chloride, gave desirable yields for the coupling step.

TABLE 1

Reaction Development for Coupling and Deprotection

Lewis Acids for Coupling

| Example | Lewis Acid | Yield (%) | SOR (°) | HPLC (%) | Remarks |
|---|---|---|---|---|---|
| 1 | TMS-triflate | 22.0 | +19.3 | 89.25 | |
| 2 | Stannic chloride + Zinc chloride (0.6 + 0.6 eq) | 22.9 | +34.6 | 90.93 | |
| 3 | Boron trifluoride diethyl etherate (1.1 eq) | 7.80 | +28.9 | 90.29 | |
| 4 | Titanium tetrachloride (1.1 eq) | 9.17 | — | 92.10 | |
| 5 | Stannic chloride + Titanium tetrachloride (0.55 + 0.55 eq) | 18.35 | +20.1 | 89.19 | |
| 6 | Ferric chloride + TMSCl (1 + 1 eq) | 33.5 | +35.2 | 97.32 | |
| 7 | Stannic chloride + Zinc chloride (25 + 75) | — | +30.6 | 85.6 | |
| 8 | Stannic chloride | 66.4 | +26.0 | 97.30 | |
| 9 | Ferric chloride | 44.8 | +19.7 | 93.28 | |

Stannic Chloride Mole Ratio (Coupling)

| Example | Ratio (Relative to 5-Azacytosine) | Yield (%) | SOR (°) | HPLC (%) | Remarks |
|---|---|---|---|---|---|
| 10 | 1.5 eq | 23.4 | +38.4 | — | |
| 11 | 0.7 eq | — | — | — | Reaction not completed |
| 12 | 1.1 eq | 66.4 | +26.0 | 97.30 | |

1,2,3,5-Tetra-O-acetyl-β-D-ribofuranose Mole Ratio (Coupling)

| Example | Ratio (Relative to 5-Azacytosine) | Yield (%) | SOR (°) | HPLC (%) | Remarks |
|---|---|---|---|---|---|
| 13 | 0.53 eq | 25.7 | +34.8 | 97.31 | |
| 14 | 0.9 eq | 66.4 | +26.0 | 97.30 | |

Solvents (Coupling)

| Example | Solvent | Yield (%) | SOR (°) | HPLC (%) | Remarks |
|---|---|---|---|---|---|
| 15 | Toluene | — | — | — | Reaction not completed |
| 16 | Acetonitrile | 41.4 | +36.0 | 97.74 | |
| 17 | Dichloromethane | 66.4 | +26.0 | 97.30 | |

Temperature (Coupling)

| Example | Temp (° C.) | Yield (%) | SOR (°) | HPLC (%) | Remarks |
|---|---|---|---|---|---|
| 18 | −5 to −10 | 41.4 | +34.2 | 97.85 | Reaction not completed |
| 19 | −15 to −20 | 32.2 | +32.5 | 93.00 | |
| 20 | 0-5 | 66.4 | +26.0 | 97.30 | |

Base (Hydrolysis)

| Example | Base | Yield (%) | SOR (°) | HPLC (%) | Remarks |
|---|---|---|---|---|---|
| 21 | Benzyl trimethyl ammonium hydroxide (0.6 eq) | 40.39 | +27.8 | 98.99 | |

5. Preparation of 5-Azacytidine HCl Salt (Salt Formation)

To remove impurities, such as metal-based impurities, in 5-azacytidine obtained from the deacetylation reaction, a hydrochloride salt of 5-azacytidine was formed. The resulting salt was broken in the next step to give the free base, and the free base was re-crystallized from DMSO by using methanol as anti-solvent to yield the purified 5-azacytidine as the final product.

To a 3-L 4-neck round bottom flask was added 5-azacytidine (140.0 g, 0.5732 mol, Example A-3) and methanol (1.4 L) at 25-30° C. under nitrogen atmosphere. The suspension was stirred for 10 minutes at 25-30° C. and then cooled to 20-25° C. Isopropanol-HCl (280.0 mL, ~14% solution) was added slowly at ≤25° C. over 5 minutes. After addition, the reaction mass became a clear solution, and after 15-60 minutes, the product was formed. The reaction mass was stirred for a total of 4 hours at 25-30° C. The product was filtered under nitrogen and washed with methanol (280.0 mL) at 25-30° C. The product was dried at 50-60° C. under vacuum (10-15 mmHg) to give the 5-azacytidine mono-hydrochloride salt as white crystalline solid (138.0 g). The average output of 5-azacytidine mono-hydrochloride salt over multiple runs was about 135.5 g, with an average purity of about 99.3%, and an average yield of about 86.4%. Over five runs, the maximum yield of 5-azacytidine mono-hydrochloride salt was about 93.29%. Over five runs, the maximum HPLC purity of the product was about 99.64%.

In one embodiment, the HCl contents were determined for mono-hydrochloride salts obtained using the above procedure to be the following:
Theoretical: 13.0%
Batch 1A: 12.99%
Batch 1B: 13.95%
Batch 1C: 12.82%
Batch 1D: 12.66%
Batch 1E: 12.79%.

6. Reaction Development (Salt Formation Step)

(a) Preparation of 5-azacytidine hemisulfate

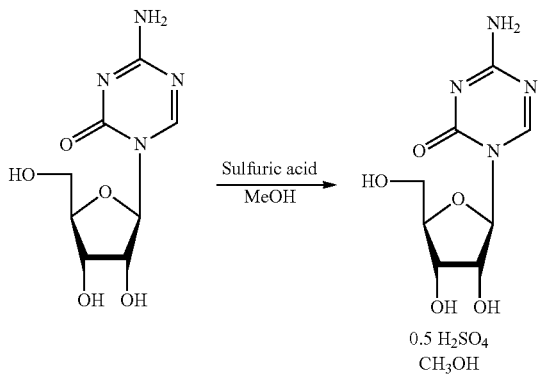

A mixture of 5-azacytidine (140.0 g, 0.5732 mol) in methanol (1.4 L) was stirred at 25-30° C. under nitrogen atmosphere for 10 minutes and cooled to 20-25° C. to give a white slurry. To this mixture was added slowly sulfuric acid (56.16 g, 0.5732 mol) at below 25° C. over a period of 30 minutes. The resulting mixture was stirred for 2 hours at 25-30° C. Then the mixture was filtered at 25-30° C. under nitrogen and washed with methanol (280 mL). The solid was dried at 50-60° C. under vacuum to give a methanol solvate of 5-azacytidine hemisulfate salt as a white solid (163.5 g, MW 325.2; 87.7% yield; melting range: 141.2-144.2° C.; SOR: −4.0° (C=1 in Water at 25° C.).

In one embodiment, the sulfuric acid contents were determined for hemisulfate salt methanol solvates obtained using the above procedure to be the following:
Theoretical: 15.0%
Batch 2A: 15.69%
Batch 2B: 15.67%
Batch 2C: 14.93%.

(b) Preparation of 5-azacytidine mesylate

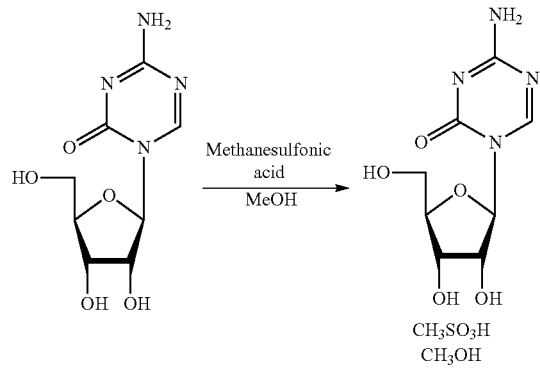

A mixture of 5-azacytidine (3.0 g, 12.28 mmol) in methanol (30 mL) was stirred at 25-30° C. under nitrogen atmosphere for 5 minutes to give a white slurry. To this mixture was added slowly methanesulfonic acid (1.18 g, 12.28 mmol) at below 30° C. over a period of 5 minutes to give a clear solution. The resulting mixture was stirred for 2 hours at 25-30° C. (after about 15 to 30 minutes, a white solid precipitated). Then the mixture was filtered at 25-30° C. under nitrogen and washed with methanol (9 mL). The solid was dried at 50-60° C. under vacuum to give a methanol solvate of 5-azacytidine mesylate salt as a white crystalline solid (2.4 g, MW 372.35; 52.7% yield; melting range: 133.5-136.8° C.; SOR: −2.3° (C=1 in Water at 25° C.).

(c) Preparation of 5-azacytidine hydrobromide

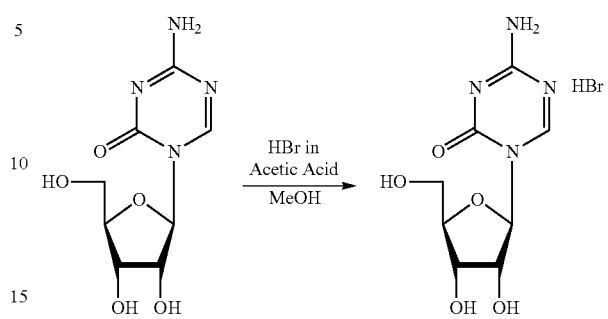

A mixture of 5-azacytidine (3.0 g, 12.28 mmol) in methanol (30 mL) was stirred at 25-30° C. under nitrogen atmosphere for 5 minutes and cooled to 20-25° C. to give a white slurry. To this mixture was added slowly HBr in acetic acid (33% w/w, 3.01 g, 12.28 mmol) at below 25° C. over a period of 30 minutes to give a clear solution. The resulting mixture was stirred for 12 hours at 25-30° C. (after about 4 to 5 hours, a white solid precipitated). Then the mixture was filtered at 25-30° C. under nitrogen and washed with methanol (9 mL). The solid was dried at 50-60° C. under vacuum to give 5-azacytidine hydrobromide salt as a white crystalline solid (2.68 g, MW 325.12; 67.0% yield; melting range: 162.4-164.9° C.; SOR: −3.9° (C=1 in Water at 25° C.).

In one embodiment, the HBr contents were determined for hydrobromide salt obtained using the above procedure to be the following:
Theoretical: 24.88%
Batch 3A: 25.15%
Batch 3B: 25.27%.

(d) 5-Azacytidine salts and metal contents

A number of inorganic and organic acids were evaluated for 5-azacytidine salt formation and the residual metal contents in the 5-azacytidine salts were determined. The results are summarized in Table 2 below.

Hydrochloric acid (HCl) formed a stable salt with 5-azacytidine, which had a low content of tin (8 ppm). The formation of 5-azacytidine hydrochloride salt afforded products that were substantially free from residual metal impurities.

TABLE 2

Reaction Development for Salt Formation

| Example # | Acid | Yield (%) | SOR (°) | MR (° C.) | HPLC (%) | Sn (ppm) | Remarks |
|---|---|---|---|---|---|---|---|
| 1 | Hydrochloric acid | 85.0 | −4.0 | 162.1-164.1 | 82.68 | 8.0 | Isolated the 5-azacytidine HCl salt |
| 2 | Hydrobromic acid in acetic acid | 67.0 | — | 162.4-164.9 | 89.71 | 240.0 | Isolated the 5-azacytidine HBr salt |
| 3 | Sulfuric acid | 88.1 | −3.0 | 145.2-148.8 | 92.98 | — | Isolated the 5-azacytidine hemisulfate salt |
| 4 | Methanesulfonic acid | 52.7 | −2.3 | 133.5-136.8 | 98.06 | — | Isolated the 5-azacytidine mesylate salt |

7. Preparation of Free Base of 5-Azacytidine (Free Base Formation)

To a 3-L 4-neck round bottom flask was added 5-azacytidine HCl salt (120.0 g, 0.4274 mol, Example A-5) and methanol (1.2 L) at 25-30° C. under nitrogen atmosphere. The suspension was stirred for 10 minutes at 25-30° C. Triethylamine (64.8 g, 0.64 mol) was added slowly at ≤30° C. The slurry was stirred for 2 hours at 25-30° C. The product was filtered under nitrogen and washed with methanol (300 mL) at 25-30° C. The presence of chloride in the filtrate was monitored by adding 10% silver nitrate solution to a fraction of the filtrate. The test showed the presence of chloride at this stage (white turbidity observed). The wet product was suspended in methanol (1.0 L) and stirred for 10 minutes at 25-30° C. The product was filtered under nitrogen and washed with methanol (200.0 mL) at 25-30° C. No chloride was detected in the filtrate after the methanol wash. The product was then dried at 50-60° C. under vacuum (10-15 mmHg) to give the 5-azacytidine free base as a white crystalline solid (103.5 g). The average output of 5-azacytidine free base over multiple runs was about 103.4 g, with an average purity of about 99.5%, and an average yield of about 97.5%. Over five runs, the maximum yield of 5-azacytidine free base was about 99.13%. Over five runs, the maximum HPLC purity of the product was about 99.77%.

8. Reaction Development (Free Base Formation Step)

A number of bases were evaluated for the salt breaking and 5-azacytidine free base formation step. The results are summarized in Table 3 below.

TABLE 3

Reaction Development for Salt Breaking/Free Base Formation

| Example # | Base | Yield (%) | SOR (°) | MR (° C.) | HPLC (%) |
|---|---|---|---|---|---|
| 1 | Diisopropylethyl amine | 97.7 | +37.1 | 219.7-221.6 | 99.30 |
| 2 | Pyridine | 91.9 | +23.0 | 165.3-168.6 | 99.54 |
| 3 | Diisopropyl amine | 94.2 | +35.5 | 217.2-219.4 | 99.46 |
| 4 | 2,6-Lutidine | 96.5 | +23.3 | 167.4-170.9 | 99.47 |
| 5 | N-Methyl morpholine | 100 | +36.0 | 217.2-219.4 | 99.23 |
| 6 | N,N-Dicyclohexyl methyl amine | 96.5 | +36.6 | 219.5-221.9 | 99.22 |

9. Re-Crystallization of 5-Azacytidine

To a 500-mL 4-neck round bottom flask was added 5-azacytidine free base (80.0 g, 0.3275 mol, Example A-7) and DMSO (200.0 mL) at 25-30° C. under nitrogen atmosphere. The suspension was stirred for 10 minutes at 25-30° C., and gradually heated to 85-90° C. The mass was stirred for 10 minutes at 85-90° C. to get a clear solution. The clear solution was filtered through a filter paper to remove insoluble particles at 85-90° C., and washed with hot DMSO (80.0 mL). Methanol (1.2 L) was slowly charged to the filtered DMSO solution containing the product at 70-80° C. over a period of 3-4 hours. The mixture was stirred for 15 minutes at 70-80° C., and gradually cooled to 25-30° C. over 2-3 hours. The mass was stirred for 15 hours at 25-30° C., and filtered under nitrogen. The solid product was washed with methanol (240.0 mL) at 25-30° C. The solid product was dried at 85-90° C. under vacuum (10-15 mmHg) until the loss on drying (LOD) fell below 0.4% to provide 5-azacytidine as a white crystalline solid (75.6 g). The average output of 5-azacytidine after the re-crystallization step over multiple runs was about 75.8 g, with an average purity of about 99.6%, and an average yield of about 95.1%. Over three runs, the maximum yield of 5-azacytidine was about 95.80%. Over three runs, the maximum HPLC purity of the product was about 99.71%.

B. Ferric Chloride Route

1. Preparation of Silylated 5-Azacytosine

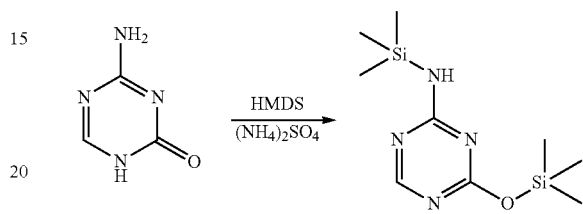

5-Azacytosine (200.0 g, 1.7842 mol, purity ≥98%) and hexamethyldisilazane (HMDS) (1.4 L, 6.72 mol, purity ≥98%) were charged into a 3-L 4-neck round bottom flask at 25-30° C. under nitrogen atmosphere. Ammonium sulfate (10.0 g, 0.0756 mol) was added. The mixture was gradually heated to reflux at 125-130° C. The reflux was maintained for 6 hours. Typically, the reaction mass became a clear solution after 2-4 hours, and the reaction was substantially complete as soon as the clear solution was formed.

The reaction mass was gradually cooled to 40-50° C. HMDS was distilled off at 40-50° C. under vacuum (10-15 mmHg) to give a white solid. Nitrogen was used to break the vacuum over the solid. Toluene (400.0 mL) was added to the solid residue at 25-30° C., and the solvent was distilled off at 40-50° C. under vacuum (10-15 mmHg) to yield a solid. Nitrogen was used to break the vacuum over the solid. The solid was gradually cooled to 25-30° C., and carried through to the next step. HMDS was recovered in 75-80% yield with a purity of about 90-95%.

2. Preparation of Acetyl-Protected 5-Azacytidine (Coupling)

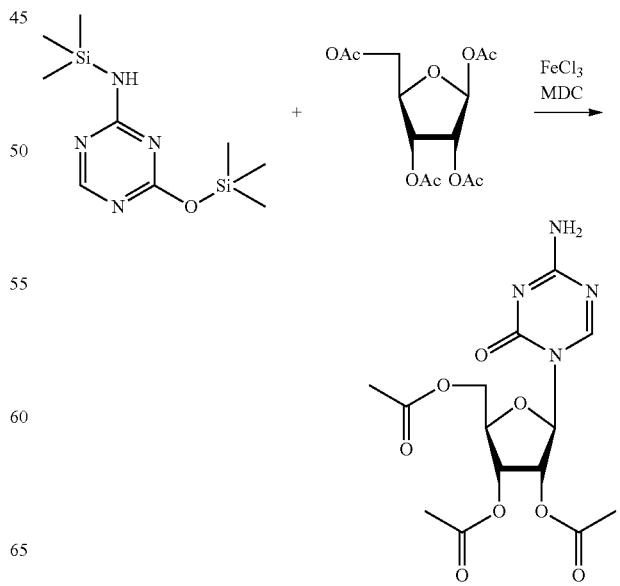

To silylated 5-azacytosine (Example B-1) was added dichloromethane (2.0 L) at 25-30° C. under nitrogen atmosphere. The mixture was stirred for 10 minutes at 25-30° C. to obtain a clear solution.

In a separate 5-L 4-neck round bottom flask under nitrogen was added 1,2,3,5-tetra-O-acetyl-β-D-ribofuranose (511.1 g, 1.6058 mol) and dichloromethane (1.0 L) at 25-30° C. The mixture was stirred for 10 minutes at 25-30° C. to obtain a clear solution. Anhydrous ferric chloride (361.7 g, 1.9627 mol) was added in one lot at 25-30° C. The mixture was stirred for 10 minutes at 25-30° C. to obtain a dark red mass. The reaction mass was gradually cooled to 0-5° C. Silylated 5-azacytosine (Example B-1) in dichloromethane was added drop-wise at ≤10° C. over 90 minutes (addition slightly exothermic), and a clear dark brown mass was formed. The reaction mass was stirred for 15 hours at 0-5° C. under nitrogen atmosphere.

The progress of the reaction was checked by HPLC. 5 g of reaction mass was withdrawn and neutralized with saturated aqueous $NaHCO_3$ solution at 10° C. The dichloromethane layer was separated and submitted for IPC-HPLC. Once IPC had been met (5-azacytosine no more than 0.5%), the reaction mass was transferred to a 10-L round bottom flask for work up.

To the reaction mass was added dichloromethane (3.0 L) and sodium bicarbonate (2.0 kg) at ≤10° C. Chilled water (1.6 L) was added drop-wise at ≤10° C. over 60 minutes (addition exothermic). The reaction mass was dark brown and had a final pH of ~6. The mixture was stirred for 30 minutes at ≤10° C. After 15-30 minutes, brown solid of ferric oxide settled to the bottom of the flask. Hyflo® (200 g) was added to the mixture, and the mass was stirred for 10 minutes at ≤10° C. The mixture was filtered through Hyflo®, and washed with dichloromethane (1.0 L). The organic layer was separated at ≤10° C., and washed with water (1.0 L) at ≤10° C. The organic layer was then washed with 10% EDTA disodium salt solution twice (300 g salt, 2×1.5 L) and water once (1.0 L) at ≤10° C. The organic layer was dried over anhydrous sodium sulfate, and the solvent was distilled off at 40-45° C. under atmospheric conditions, and further dried at 40-45° C. under vacuum (10-15 mmHg) to give a sticky foaming solid. To the residue was added methanol (200 mL) at 30-35° C. The solvent was then distilled off at 40-45° C. under vacuum (10-15 mmHg), and degassed under vacuum for 30 minutes to afford 2',3',5'-triacetyl-5-azacytidine as a sticky foaming white solid. The average output of 2',3',5'-triacetyl-5-azacytidine over multiple runs was about 524 g, with an average purity of about 63.3%, and an average yield of about 50.2% (% yield takes into account the HPLC purity of the product). Over three runs, the maximum yield of 2',3',5'-triacetyl-5-azacytidine was about 64.9% (% yield takes into account the HPLC purity of the product). Over three runs, the maximum HPLC purity of the product was about 82.45%.

3. Preparation of 5-Azacytidine (Deprotection)

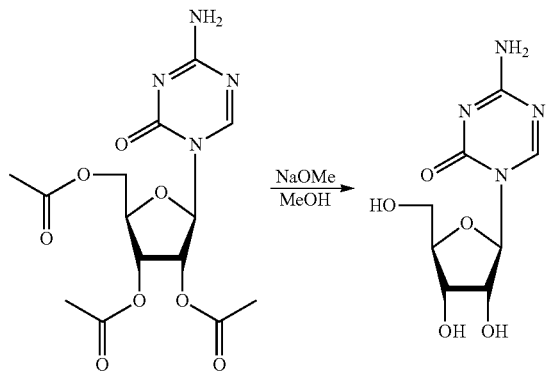

To 2',3',5'-triacetyl-5-azacytidine (Example B-2) was added methanol (2.0 L) at 25-30° C. The slurry was stirred for 10 minutes at 25-30° C., and 25% sodium methoxide in methanol (80.0 mL) was added slowly at 25-30° C. under nitrogen atmosphere. After addition, the reaction mass became a clear solution and the product immediately formed. The pH value of the reaction mass was above 10. The reaction mass was stirred for 18 hours at 25-30° C.

The progress of the reaction was checked by HPLC. A sample of the reaction mass was withdrawn and submitted for IPC-HPLC. Once IPC had been met (IPC-HPLC: 2',3', 5'-triacetylazacitidine ≤0.5%), the product was filtered under nitrogen, and washed with methanol (600.0 mL) at 25-30° C. The product was dried at 60-65° C. under vacuum (10-15 mmHg) to give an off-white solid (195.5 g). The average output of 5-azacytidine over multiple runs was about 193.7 g, with an average purity of about 91.8%, and an average yield of about 44.4% (based on 5-azacytosine). Over three runs, the maximum yield of 5-azacytidine was about 44.86% (based on 5-azacytosine). Over three runs, the maximum HPLC purity of the product was about 93.28%.

4. Reaction Development (Coupling and Deprotection Steps)

The reaction conditions for the coupling step were optimized by varying parameters such as the molar ratio of the reagents. The results are summarized in the Table 4 below.

TABLE 4

Reaction Development for the Ferric Chloride Coupling Step
Ferric Chloride Mole Ratio (Coupling)

| Example # | Ratio (Relative to Azacytosine) | Yield (%) | SOR (°) | HPLC (%) | Remarks |
|---|---|---|---|---|---|
| 1 | 1.5 eq | 33.0 | +31.4 | 95.46 | |
| 2 | 1.1 eq | 44.8 | +19.7 | 93.28 | |

5. Preparation of 5-Azacytidine HCl Salt (Salt Formation)

To a 3-L 4-neck round bottom flask was added 5-azacytidine (175.0 g, 0.7166 mol, Example B-3) and methanol (1.75 L) at 25-30° C. under nitrogen atmosphere. The suspension was stirred for 10 minutes at 25-30° C. and then cooled to 20-25° C. Isopropanol-HCl (350.0 mL, ~14% solution) was added slowly at ≤25° C. over 5 minutes. After addition, the reaction mass became a clear solution, and after 15-60 minutes, the product was formed. The reaction mass was stirred for a total of 4 hours at 25-30° C. The product was filtered under nitrogen and washed with methanol (350.0 mL) at 25-30° C. The product was dried at 50-60° C. under vacuum (10-15 mmHg) to give the 5-azacytidine mono-hydrochloride salt as off-white crystalline solid (151.0 g). The average output of 5-azacytidine mono-hydrochloride salt over multiple runs was about 148.8 g, with an average purity of about 99.0%, and an average yield of about 74.0%. Over three runs, the maximum yield of 5-azacytidine monohydrochloride salt was about 75.09%. Over three runs, the maximum HPLC purity of the product was about 99.12%.

6. Preparation of Free Base of 5-Azacytidine (Free Base Formation)

To a 3-L 4-neck round bottom flask was added 5-azacytidine hydrochloride salt (130.0 g, 0.4631 mol, Example B-5) and methanol (1.3 L) at 25-30° C. under nitrogen atmosphere. The suspension was stirred for 10 minutes at 25-30° C. Triethylamine (70.3 g, 0.6946 mol) was added slowly at ≤30° C. The slurry was stirred for 2 hours at 25-30° C. The product was filtered under nitrogen and washed with methanol (300.0 mL) at 25-30° C. The presence of chloride in the filtrate was checked by adding 10% silver nitrate solution to a fraction of the filtrate. The test showed the presence of chloride at this stage (white turbidity observed). The wet product was suspended in methanol (1.0 L) and stirred for 10 minutes at 25-30° C. The product was filtered under nitrogen and washed with methanol (200.0 mL) at 25-30° C. No chloride was detected in the filtrate after the methanol wash. The product was then dried at 50-60° C. under vacuum (10-15 mmHg) to give the 5-azacytidine free base as an off-white solid (113.0 g). The average output of 5-azacytidine free base over multiple runs was about 112.5 g, with an average purity of about 99.2%, and an average yield of about 99.5%. Over three runs, the maximum yield of 5-azacytidine free base was about 99.99%. Over three runs, the maximum HPLC purity of the product was about 99.38%.

7. Re-Crystallization of 5-Azacytidine

To a 500-mL 4-neck round bottom flask was added 5-azacytidine free base (100.0 g, 0.4095 mol, Example B-6) and DMSO (250.0 mL) at 25-30° C. under nitrogen atmosphere. The suspension was stirred for 10 minutes at 25-30° C., and gradually heated to 85-90° C. The mass was stirred for 10 minutes at 85-90° C. to obtain a clear solution. The clear solution was filtered through a filter paper to remove insoluble particles at 85-90° C., and washed with hot DMSO (100.0 mL). Methanol (1.5 L) was slowly charged to the filtered DMSO solution containing the product at 70-80° C. over a period of 3-4 hours. The mixture was stirred for 15 minutes at 70-80° C., and gradually cooled to 25-30° C. over 2-3 hours. The mass was stirred for 15 hours at 25-30° C., and filtered under nitrogen. The solid product was washed with methanol (240.0 mL) at 25-30° C. The solid product was dried at 85-90° C. under vacuum (10-15 mmHg) until the LOD fell below 0.4% to provide 5-azacytidine as a white solid (86.0 g). The average output of 5-azacytidine after the re-crystallization step over multiple runs was about 86.0 g, with an average purity of about 99.4%, and an average yield of about 86.0%. Over three runs, the maximum yield of 5-azacytidine was about 87.5%. Over three runs, the maximum HPLC purity of the product was about 99.54%.

C. Comparative Data

Reaction yields, purity profiles (by HPLC), water contents (by KF, % w/w), specific optional rotation (SOR, $[\alpha]_D$), and metal impurity contents (e.g., Sn or Fe, when applicable) were gathered from repeat batches of various steps along three different routes used for preparing 5-azacytidine. The triflate route utilized TMS-triflate as the Lewis acid in the coupling step. The stannic chloride route utilized stannic chloride as the Lewis acid in the coupling step (See Example A herein). The ferric chloride route utilized ferric chloride as the Lewis acid in the coupling step (See Example B herein). The following tables summarize the data for specific batches. Both stannic chloride and ferric chloride gave good overall yield for the synthesis of 5-azacytidine from 5-azacytosine and acetyl protected sugar. Hydrochloride salt formation and the subsequent steps of breaking the salt to form the free base and re-crystallization of the free base consistently provided 5-azacytidine batches that were substantially free of metal impurities.

1. Preparation of Triacetyl 5-Azacytidine

TABLE 5

Triflate Route

| Example # | Input (g)* | Output (g)† | Yield (%)‡ | HPLC Purity (RRT, A %) | | | | | | | |
|---|---|---|---|---|---|---|---|---|---|---|---|
| | | | | 1.00 | 1.06 | 0.52 | 0.71 | 0.84 | 0.91 | 0.94 | 0.95 | 1.14 |
| 1 | 10.0 | 25.8 | 29.1 | 37.34 | 22.32 | 1.95 | 0.18 | 3.58 | 0.84 | 1.15 | 9.20 | 8.60 |
| 2 | 10.0 | 24.5 | 22.7 | 30.72 | 17.49 | 2.59 | 0.77 | 3.45 | 0.64 | 0.94 | 9.40 | 7.35 |

TABLE 6

Stannic Chloride Route

| Example # | Input (g)* | Output (g)† | Yield (%)‡ | HPLC Purity (RRT, A %) | | | | | | | |
|---|---|---|---|---|---|---|---|---|---|---|---|
| | | | | 1.00 | 1.06 | 0.52 | 0.71 | 0.84 | 0.91 | 0.94 | 0.95 | 1.14 |
| 3 | 100 | 278.0 | 72.3 | 85.94 | 8.52 | — | — | — | — | 0.33 | 1.21 | 0.40 | — |
| 4 | 100 | 308.0 | 81.8 | 87.8 | — | — | — | — | — | 0.54 | — | 0.69 | 0.12 |
| 5 | 100 | 310.0 | 78.1 | 83.30 | 15.37 | — | — | — | — | 0.42 | — | — | 0.26 |
| 6 | 100 | 315.0 | 75.0 | 78.70 | 7.01 | 1.59 | 6.33 | 3.17 | — | — | — | — |
| 7 | 100 | 315.0 | 78.9 | 82.75 | 5.49 | 0.69 | 3.58 | 3.01 | — | — | — | — |

TABLE 7

Ferric Chloride Route

| Example # | Input (g)* | Output (g)† | Yield (%)‡ | HPLC Purity (RRT, A %) | | | | | |
|---|---|---|---|---|---|---|---|---|---|
| | | | | 1.00 | 1.06 | 0.82 | 0.83 | 0.95 | 0.96 | 1.41 |
| 8 | 200.0 | 520.0 | 64.9 | 82.45 | 8.84 | 0.64 | 1.45 | — | 0.14 | 2.20 |
| 9 | 200.0 | 535.0 | 50.6 | 62.54 | 0.15 | 3.73 | 6.38 | 1.61 | 0.64 | 5.84 |
| 10 | 200.0 | 517.0 | 35.1 | 44.85 | 2.03 | 11.99 | 8.34 | 4.02 | 3.29 | 3.87 |

*5-azacytosine
†Residue weight
‡The % yield by theory is based on HPLC purity.

2. Preparation of 5-Azacytidine by Deacetylation

TABLE 8

Triflate Route

| Example # | Input (g)* | Output (g) | Yield (%)‡ | HPLC (%) | KF (%) | SOR (°) |
|---|---|---|---|---|---|---|
| 1 | 10.0 | 5.5 | 25.2 | 93.05 | 1.11 | +28.6 |
| 2 | 10.0 | 4.8 | 22.0 | 89.25 | 1.65 | +19.29 |

TABLE 9

Stanic Chloride Route

| Example # | Input (g)* | Output (g) | Yield (%)‡ | HPLC (%) | KF (%) | SOR (°) | Sn (ppm) |
|---|---|---|---|---|---|---|---|
| 3 | 100.0 | 132.0 | 60.58 | 98.14 | 0.49 | +28.9 | 2.22 |
| 4 | 100.0 | 137.5 | 63.11 | 95.17 | 1.54 | +25.6 | <1.0 |
| 5 | 100.0 | 132.7 | 60.90 | 98.83 | 1.08 | +27.5 | 46.9 |
| 6 | 100.0 | 144.8 | 66.46 | 97.30 | 1.40 | +26.0 | 118.22 |
| 7 | 100.0 | 159.5 | 73.20 | 94.42 | 1.11 | +28.6 | 144.38 |

TABLE 10

Ferric Chloride Route

| Example # | Input (g)* | Output (g) | Yield (%)‡ | HPLC (%) | KF (%) | SOR (°) | Fe (ppm) |
|---|---|---|---|---|---|---|---|
| 8 | 200.0 | 195.5 | 44.86 | 93.28 | 2.09 | +19.7 | 77.1 |
| 9 | 200.0 | 190.0 | 43.60 | 90.48 | 2.14 | +19.6 | 36.9 |
| 10 | 200.0 | 195.5 | 44.86 | 91.73 | 2.03 | +24.1 | 49.1 |

*5-azacytosine
‡The % yield is based on 5-azacytosine

3. Preparation of 5-Azacytidine Hydrochloride Salt

TABLE 11

Stannic Chloride Route

| Example # | Input (g) | Output (g) | Yield (%) | HPLC (%) | KF (%) | SOR (°) | Sn (ppm) |
|---|---|---|---|---|---|---|---|
| 1 | 140.0 | 138.0 | 85.79 | 99.57 | 0.24 | −5.4 | 1.62 |
| 2 | 140.0 | 133.0 | 82.68 | 99.48 | 0.32 | −4.5 | 2.75 |
| 3 | 95.0 | 87.8 | 80.43 | 98.47 | 0.49 | −4.5 | <1.0 |
| 4 | 125.0 | 134.0 | 93.29 | 99.64 | 0.49 | −5.2 | <1.0 |
| 5 | 130.0 | 134.0 | 89.71 | 99.52 | 1.54 | −4.5 | <1.0 |

TABLE 12

Ferric Chloride Route

| Example # | Input (g) | Output (g) | Yield (%) | HPLC (%) | KF (%) | SOR (°) | Fe (ppm) |
|---|---|---|---|---|---|---|---|
| 6 | 175.0 | 151.0 | 75.09 | 99.12 | 0.21 | −3.6 | <1.0 |
| 7 | 175.0 | 146.0 | 72.61 | 98.99 | 0.21 | −3.8 | <1.0 |
| 8 | 175.0 | 149.5 | 74.35 | 98.89 | 0.52 | −3.9 | <1.0 |

4. Preparation of 5-Azacytidine Free Base from HCl Salt

TABLE 13

Stannic Chloride Route

| Example # | Input (g) | Output (g) | Yield (%) | HPLC (%) | KF (%) | SOR (°) | Sn (ppm) |
|---|---|---|---|---|---|---|---|
| 1 | 120.0 | 103.5 | 99.13 | 99.48 | 0.54 | +34.7 | 1.8 |
| 2 | 120.0 | 103.3 | 98.84 | 99.67 | 0.32 | +33.3 | 2.5 |
| 3 | 80.0 | 66.6 | 95.68 | 99.00 | 0.53 | +35.7 | <1.0 |
| 4 | 85.0 | 71.3 | 96.41 | 99.77 | 0.25 | +36.5 | <1.0 |
| 5 | 125.0 | 105.8 | 97.28 | 99.72 | 0.11 | +35.8 | <1.0 |

TABLE 14

Ferric Chloride Route

| Example # | Input (g) | Output (g) | Yield (%) | HPLC (%) | KF (%) | SOR (°) | Fe (ppm) |
|---|---|---|---|---|---|---|---|
| 6 | 130.0 | 113.0 | 99.99 | 99.04 | 0.61 | +36.6 | 3.11 |
| 7 | 130.0 | 112.5 | 99.47 | 99.38 | 0.63 | +36.5 | 3.02 |
| 8 | 130.0 | 112.0 | 99.02 | 99.21 | 0.59 | +36.6 | <1.0 |

5. Re-Crystallization of 5-Azacytidine

TABLE 15

Stannic Chloride Route

| Exmp. # | Yield (%) | SOR (°) | HPLC Purity @ 210 nm (RRT, A %) 1.00 | 0.68 | 3.5 | 4.6 | 5.2 | Total | HPLC Assay % w/w | Chemical Assay % w/w | Sn (ppm) | KF (%) | LOD (%) |
|---|---|---|---|---|---|---|---|---|---|---|---|---|---|
| 1 | 94.50 | +37.7 | 99.71 | 0.11 | 0.18 | — | — | 0.29 | 100.33 | 98.51 | <1.0 | 0.59 | 0.09 |
| 2 | 95.00 | +38.2 | 99.61 | 0.02 | 0.25 | 0.10 | 0.02 | 0.39 | 99.34 | 99.85 | <1.0 | 0.48 | 0.29 |
| 3 | 95.80 | +37.3 | 99.48 | 0.09 | 0.23 | 0.10 | 0.10 | 0.52 | 100.35 | 99.71 | <1.0 | 0.26 | 0.10 |

TABLE 16

Ferric Chloride Route

| Exmp. # | Yield (%) | SOR (°) | HPLC Purity @ 210 nm (RRT, A %) | | | | | | HPLC Assay % w/w | Chemical Assay % w/w | Fe (ppm) | KF (%) | LOD (%) |
|---|---|---|---|---|---|---|---|---|---|---|---|---|---|
| | | | 1.00 | 0.68 | 3.5 | 4.6 | 5.2 | Total | | | | | |
| 4 | 86.0 | +39.7 | 99.54 | 0.03 | 0.29 | 0.11 | 0.03 | 0.46 | 98.25 | 99.13 | <1.0 | 0.14 | 0.20 |
| 5 | 87.5 | +38.2 | 99.37 | 0.11 | 0.34 | 0.15 | 0.03 | 0.63 | 99.42 | 98.33 | <1.0 | 0.28 | 0 |
| 6 | 84.6 | +38.2 | 99.47 | 0.03 | 0.28 | 0.20 | 0.02 | 0.53 | 98.71 | 98.84 | <1.0 | 0.48 | 0.20 |

D. Analytical Data

The analytical data were obtained and provided below for repeat batches of 5-azacytidine final products, salts of 5-azacytidine, and the triacetyl 5-azacytidine intermediate.

1. 5-Azacytidine Final Product $^1$H NMR (DMSO-d$_6$) δ 8.57 (s, 1H), 7.52 (d, 2H, J=10.6 Hz), 5.65 (d, 1H, J=3.7 Hz), 5.42 (d, 1H, J=5.1 Hz), 5.10 (t, 1H, J=5.0 Hz), 5.02 (d, 1H, J=5.7 Hz), 4.07 (m, 1H), 4.00 (m, 1H), 3.84 (m, 1H), 3.67 (m, 1H), 3.55 (m, 1H).

$^{13}$C NMR (DMSO-d$_6$) δ 166.1, 156.7, 153.7, 89.6, 84.6, 74.2, 69.3, 60.5.

LC-MS ESI: m/z 245.2 (M+H$^+$), 267.1 (M+Na$^+$).

Figure 2:
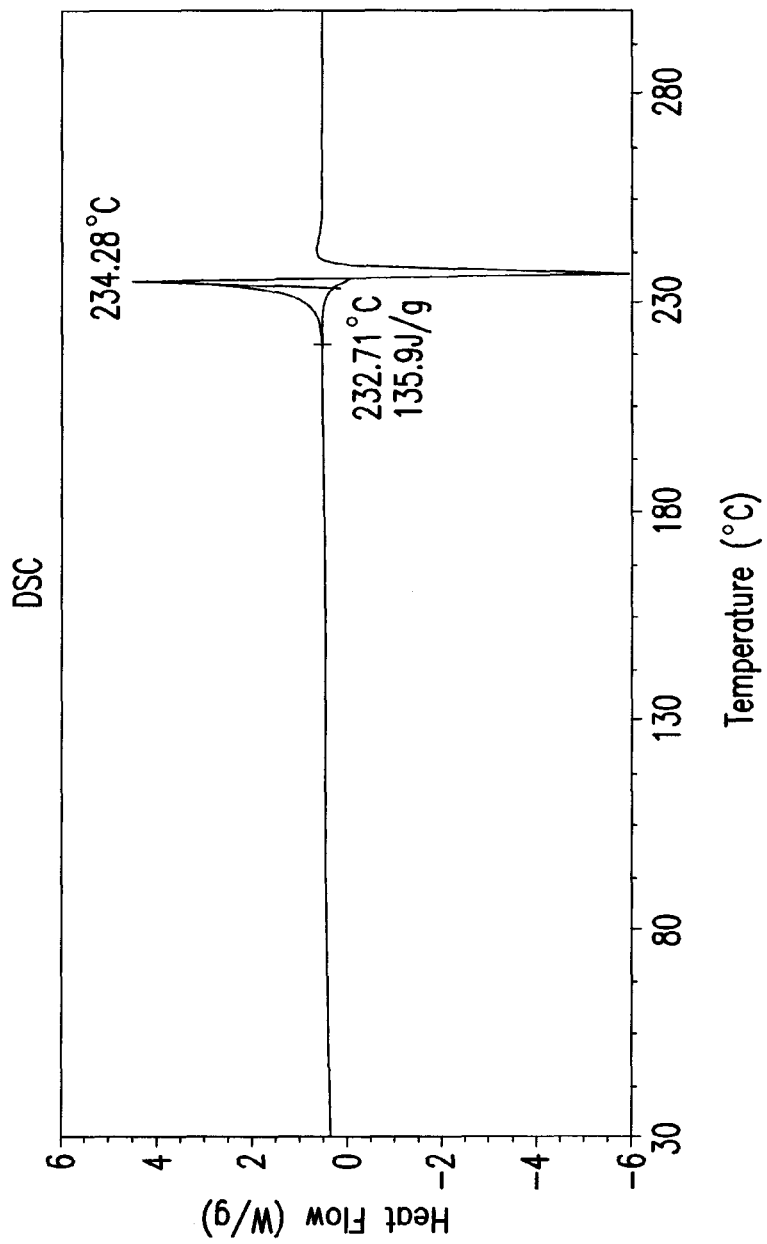
FIG. 2 represents a Differential Scanning calorimetry (DSC) plot of 5-azacytidine.
Figure 2:
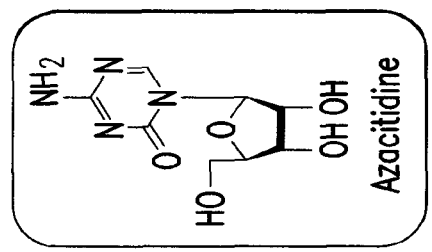
Figure 3:
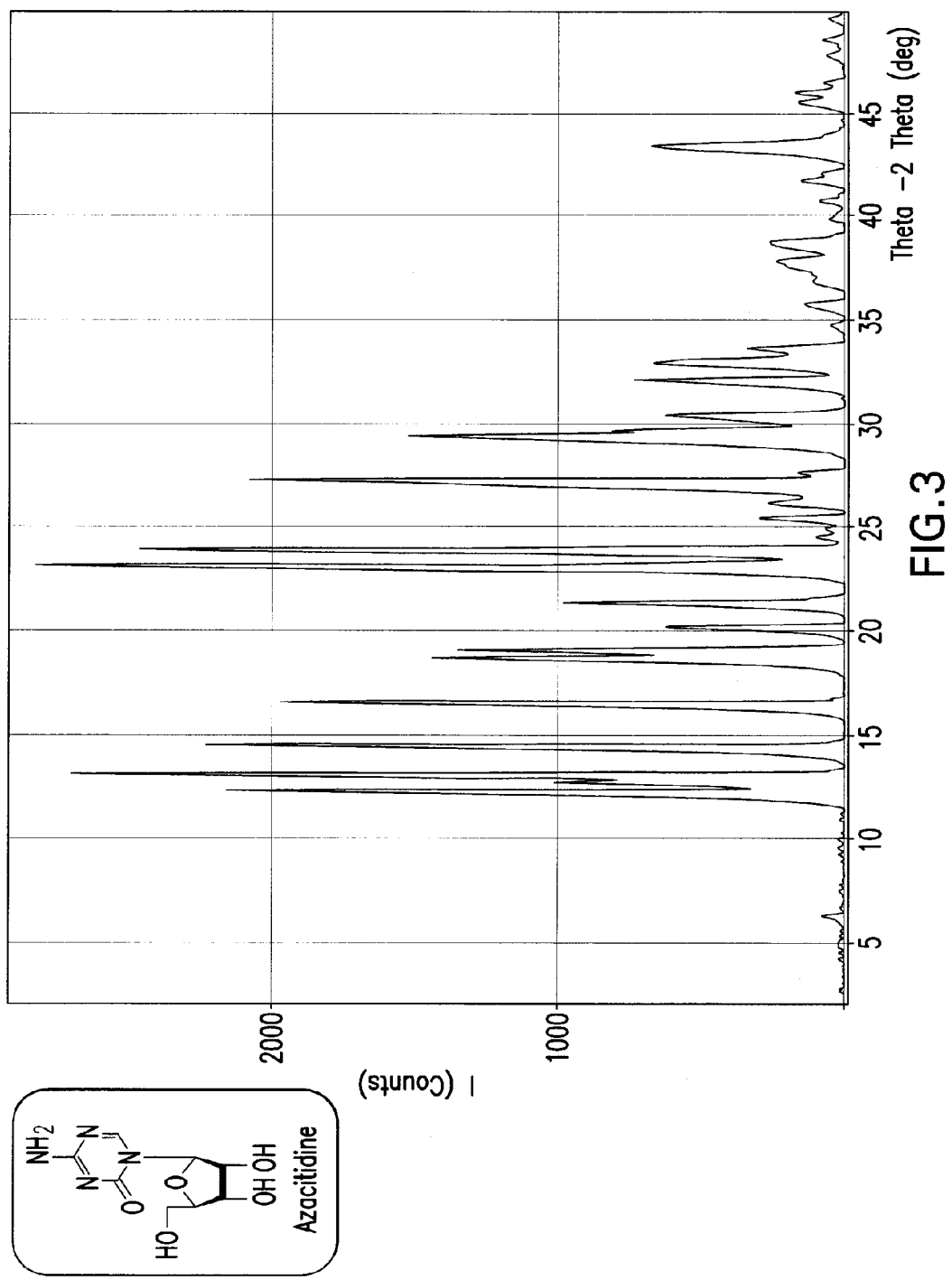
FIG. 3 represents an X-Ray Powder Diffraction (XRPD) pattern of 5-azacytidine.

For 5-azacytidine obtained from the stannic chloride route, the IR spectrum is shown in FIG. 1; the DSC plot is shown in FIG. 2; the XRPD pattern is shown in FIG. 3. The XRPD data is further provided in the tables below:

TABLE 17

XRPD - Strongest 3 peaks

| no. | Peak no. | 2Theta (deg) | d (A) | I/I1 | FWHM (deg) | Intensity (Counts) | Integrated Int (Counts) |
|---|---|---|---|---|---|---|---|
| 1 | 12 | 22.9979 | 3.86406 | 100 | 0.26900 | 1955 | 32423 |
| 2 | 4 | 12.9834 | 6.81324 | 94 | 0.23960 | 1843 | 22060 |
| 3 | 13 | 23.8179 | 3.73285 | 87 | 0.28000 | 1708 | 26470 |

TABLE 18

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 11.8200 | 7.48110 | 11 | 0.17140 | 210 | 2859 |
| 2 | 12.1412 | 7.28390 | 75 | 0.25280 | 1471 | 18956 |
| 3 | 12.6200 | 7.00860 | 35 | 0.29760 | 681 | 11254 |
| 4 | 12.9834 | 6.81324 | 94 | 0.23960 | 1843 | 22060 |
| 5 | 13.9400 | 6.34777 | 5 | 0.17340 | 102 | 2226 |
| 6 | 14.3503 | 6.16719 | 77 | 0.25620 | 1509 | 20932 |
| 7 | 16.4330 | 5.38996 | 69 | 0.23430 | 1340 | 18847 |
| 8 | 18.6020 | 4.76609 | 50 | 0.30420 | 982 | 15985 |
| 9 | 18.9777 | 4.67257 | 47 | 0.31320 | 927 | 14624 |
| 10 | 20.1354 | 4.40646 | 22 | 0.26230 | 432 | 6317 |
| 11 | 21.2857 | 4.17085 | 35 | 0.24720 | 679 | 10220 |
| 12 | 22.9979 | 3.86406 | 100 | 0.26900 | 1955 | 32423 |
| 13 | 23.8179 | 3.73285 | 87 | 0.28000 | 1708 | 26470 |
| 14 | 24.4956 | 3.63109 | 4 | 0.29530 | 74 | 1696 |
| 15 | 25.3727 | 3.50752 | 11 | 0.27200 | 208 | 3112 |
| 16 | 26.1000 | 3.41141 | 10 | 0.32880 | 187 | 4032 |
| 17 | 26.8000 | 3.32387 | 32 | 0.24100 | 633 | 7938 |
| 18 | 27.0310 | 3.29599 | 74 | 0.38780 | 1448 | 21079 |
| 19 | 27.6000 | 3.22932 | 6 | 0.22320 | 122 | 1731 |
| 20 | 29.2077 | 3.05512 | 54 | 0.40890 | 1059 | 21215 |
| 21 | 29.5800 | 3.01751 | 29 | 0.28080 | 572 | 8109 |
| 22 | 30.0600 | 2.97041 | 12 | 0.40400 | 233 | 4726 |
| 23 | 30.3400 | 2.94363 | 22 | 0.27600 | 439 | 5627 |
| 24 | 31.9890 | 2.79555 | 26 | 0.33460 | 518 | 9593 |
| 25 | 32.8941 | 2.72067 | 24 | 0.48740 | 466 | 12216 |
| 26 | 33.5800 | 2.66665 | 13 | 0.29640 | 245 | 4483 |
| 27 | 35.6631 | 2.51552 | 5 | 0.40630 | 100 | 2420 |
| 28 | 36.7600 | 2.44293 | 4 | 0.42220 | 76 | 2237 |
| 29 | 37.1600 | 2.41755 | 4 | 0.00000 | 79 | 0 |
| 30 | 37.4800 | 2.39764 | 7 | 0.00000 | 142 | 0 |
| 31 | 37.7800 | 2.37929 | 9 | 0.36000 | 167 | 3804 |
| 32 | 38.5538 | 2.33330 | 9 | 0.57560 | 178 | 5997 |
| 33 | 40.6547 | 2.21744 | 4 | 0.21940 | 71 | 1081 |
| 34 | 41.6215 | 2.16813 | 6 | 0.27300 | 114 | 2437 |
| 35 | 43.2476 | 2.09031 | 23 | 0.50800 | 459 | 13218 |
| 36 | 43.9000 | 2.06074 | 3 | 0.20000 | 61 | 953 |
| 37 | 45.4727 | 1.99306 | 6 | 0.38550 | 113 | 2474 |
| 38 | 45.9450 | 1.97366 | 7 | 0.26140 | 130 | 1753 |
| 39 | 46.4544 | 1.95320 | 3 | 0.23880 | 59 | 823 |
| 40 | 48.5714 | 1.87290 | 3 | 0.21710 | 59 | 899 |

Figure 4:
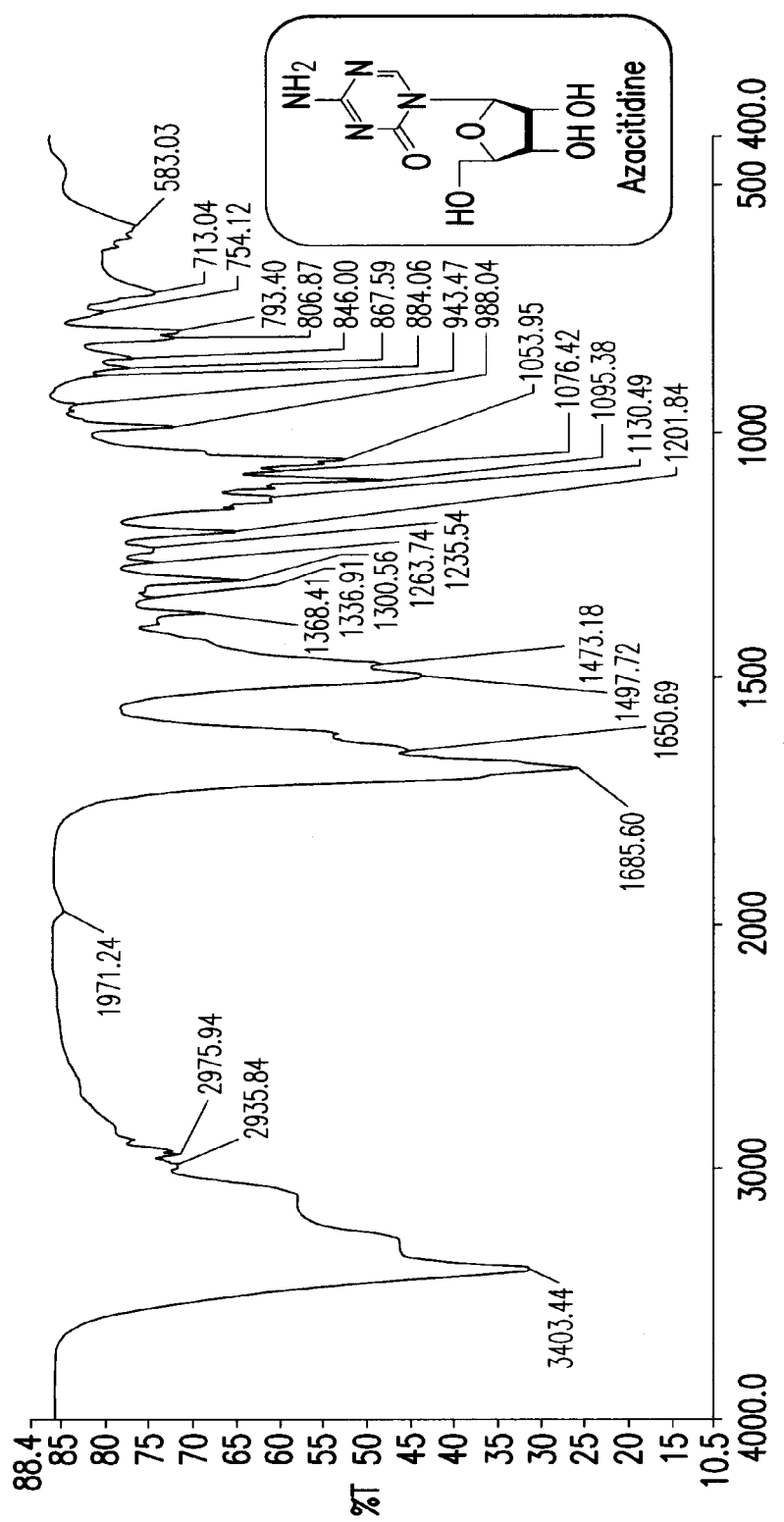
FIG. 4 represents an IR spectrum of 5-azacytidine.
Figure 5:
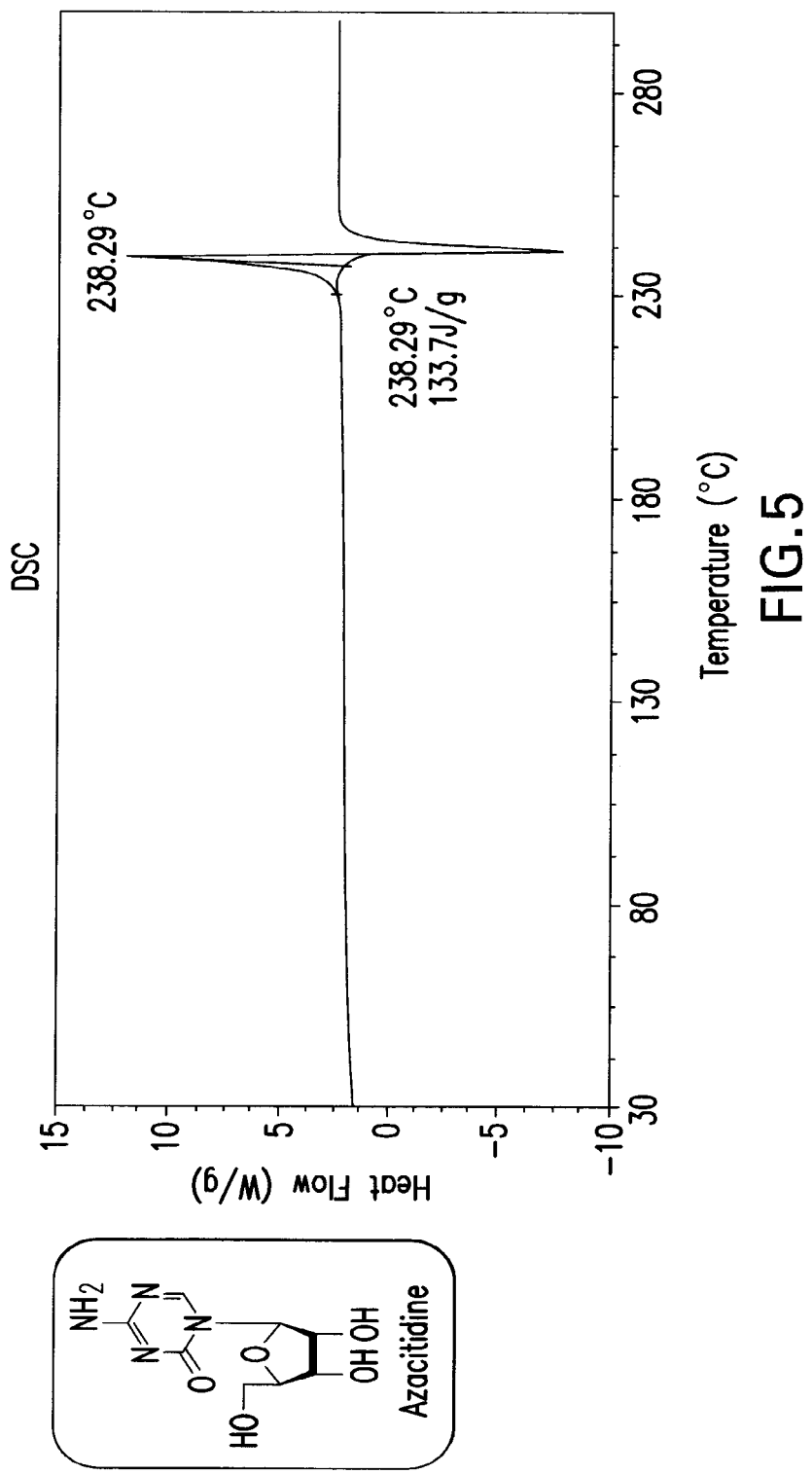
FIG. 5 represents a DSC plot of 5-azacytidine.
Figure 6:
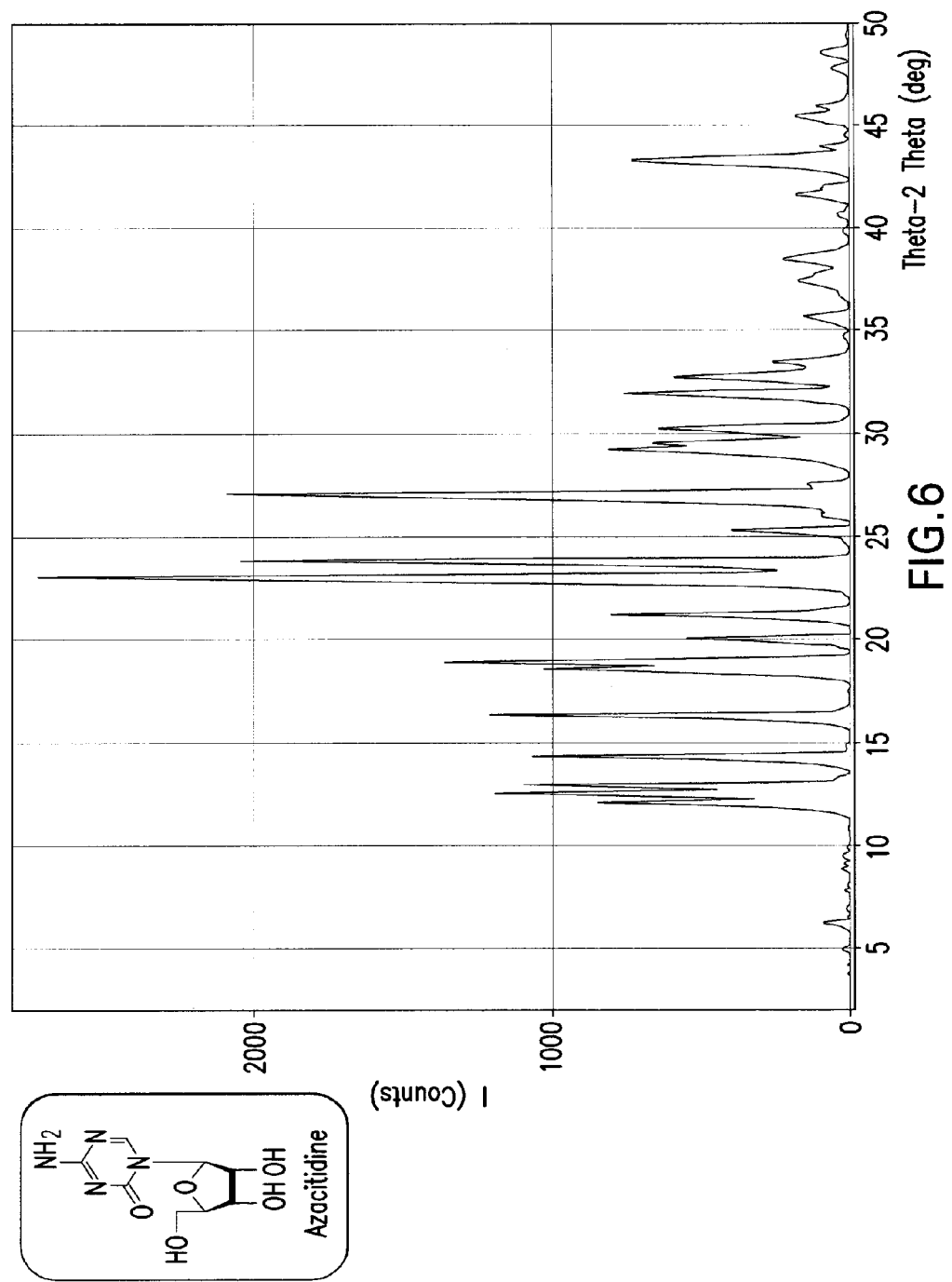
FIG. 6 represents an XRPD pattern of 5-azacytidine.

For 5-azacytidine obtained from the ferric chloride route, the IR spectrum is shown in FIG. 4; the DSC plot is shown in FIG. 5; the XRPD pattern is shown in FIG. 6. The XRPD data is further provided in the tables below.

TABLE 19

XRPD - Strongest 3 peaks

| no. | Peak no. | 2Theta (deg) | d (A) | I/I1 | FWHM (deg) | Intensity (Counts) | Integrated Int (Counts) |
|---|---|---|---|---|---|---|---|
| 1 | 12 | 22.9372 | 3.87415 | 100 | 0.28580 | 1875 | 33155 |
| 2 | 16 | 26.9754 | 3.30265 | 77 | 0.39750 | 1453 | 29755 |
| 3 | 13 | 23.7666 | 3.74079 | 75 | 0.28730 | 1411 | 22685 |

TABLE 20

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 6.2567 | 14.11507 | 3 | 0.21750 | 64 | 900 |
| 2 | 12.1042 | 7.30608 | 30 | 0.29350 | 568 | 9641 |
| 3 | 12.5625 | 7.04055 | 43 | 0.26670 | 803 | 10544 |
| 4 | 12.9293 | 6.84163 | 40 | 0.25960 | 748 | 10118 |
| 5 | 14.2979 | 6.18967 | 39 | 0.27110 | 729 | 11550 |
| 6 | 16.0000 | 5.53483 | 4 | 0.13000 | 78 | 1032 |
| 7 | 16.3803 | 5.40718 | 44 | 0.24810 | 822 | 11165 |

TABLE 20-continued

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 8 | 18.5800 | 4.77168 | 37 | 0.37060 | 697 | 12661 |
| 9 | 18.9199 | 4.68672 | 49 | 0.31740 | 923 | 13819 |
| 10 | 20.0734 | 4.41993 | 20 | 0.28210 | 374 | 5876 |
| 11 | 21.2364 | 4.18042 | 29 | 0.26330 | 552 | 8712 |
| 12 | 22.9372 | 3.87415 | 100 | 0.28580 | 1875 | 33155 |
| 13 | 23.7666 | 3.74079 | 75 | 0.28730 | 1411 | 22685 |
| 14 | 25.3226 | 3.51435 | 15 | 0.27870 | 276 | 4329 |
| 15 | 26.0600 | 3.41655 | 4 | 0.28880 | 69 | 1818 |
| 16 | 26.9754 | 3.30265 | 77 | 0.39750 | 1453 | 29755 |
| 17 | 27.5400 | 3.23622 | 6 | 0.26660 | 105 | 1838 |
| 18 | 29.2000 | 3.05590 | 30 | 0.46500 | 567 | 12422 |
| 19 | 29.5200 | 3.02350 | 24 | 0.32000 | 454 | 8137 |
| 20 | 30.0000 | 2.97621 | 11 | 0.00000 | 208 | 0 |
| 21 | 30.2800 | 2.94932 | 24 | 0.29420 | 441 | 8207 |
| 22 | 31.9369 | 2.79999 | 28 | 0.33290 | 529 | 10079 |
| 23 | 32.7835 | 2.72959 | 22 | 0.40900 | 411 | 9358 |
| 24 | 33.5200 | 2.67128 | 10 | 0.30660 | 184 | 3603 |
| 25 | 35.6416 | 2.51698 | 6 | 0.34330 | 106 | 2269 |
| 26 | 37.1600 | 2.41755 | 3 | 0.29000 | 59 | 1190 |
| 27 | 37.4200 | 2.40135 | 7 | 0.37000 | 123 | 1475 |
| 28 | 37.7200 | 2.38293 | 4 | 0.42400 | 80 | 1526 |
| 29 | 38.4710 | 2.33813 | 8 | 0.56870 | 151 | 4430 |
| 30 | 41.5706 | 2.17067 | 7 | 0.28990 | 134 | 2135 |
| 31 | 41.9600 | 2.15142 | 3 | 0.30000 | 62 | 1080 |
| 32 | 43.2083 | 2.09212 | 27 | 0.49400 | 497 | 13585 |
| 33 | 43.9525 | 2.05840 | 4 | 0.19640 | 79 | 920 |
| 34 | 45.3612 | 1.99770 | 7 | 0.43750 | 126 | 2877 |
| 35 | 45.8820 | 1.97623 | 4 | 0.30800 | 78 | 1268 |
| 36 | 48.5080 | 1.87520 | 4 | 0.31200 | 71 | 1792 |

Additional analytical data for repeat batches of the 5-azacytidine final product are provided in the tables below.

TABLE 21

Stannic Chloride Route

| Exmp. # | LOD at 105 ± 5° C. (% w/w) | Residue on ignition (% w/w) | $[\alpha]_D$ (1.0% water) (in°) | Heavy metal (ppm) | Tin content (ppm) | DSC | HPLC single impurity % area | HPLC total impurity % area | Assay by HPLC % w/w | Assay by chemical % w/w |
|---|---|---|---|---|---|---|---|---|---|---|
| 1 | 0.09 | 0.13 | +37.7 | <20 | <1.0 | 234.3° | 0.25 | 0.39 | 100.33 | 98.51 |
| 2 | 0.29 | 0.13 | +38.2 | <20 | <1.0 | 234.2° | 0.30 | 0.37 | 99.34 | 99.85 |
| 3 | 0.10 | 0.08 | +37.3 | <20 | <1.0 | 238.9° | 0.27 | 0.42 | 100.35 | 99.71 |

TABLE 22

Ferric Chloride Route

| Exmp. # | LOD at 105 ± 5° C. (% w/w) | Residue on ignition (% w/w) | $[\alpha]_D$ (1.0% water) (in°) | Heavy metal (ppm) | Iron content (ppm) | DSC | HPLC single impurity % area | HPLC total impurity % area | Assay by HPLC % w/w | Assay by chemical % w/w |
|---|---|---|---|---|---|---|---|---|---|---|
| 4 | 0.20 | 0.02 | +39.7 | <20 | <1.0 | 238.3° | 0.37 | 0.47 | 98.25 | 99.13 |
| 5 | Nil | 0.09 | +38.2 | <20 | <1.0 | 235.2° | 0.39 | 0.59 | 99.42 | 98.33 |
| 6 | 0.20 | 0.09 | +37.9 | <20 | <1.0 | 238.5° | 0.30 | 0.40 | 98.71 | 98.84 |

The metal content of repeat batches of 5-azacytidine was determined. For 5-azacytidine obtained from the stannic chloride route, the tin contents in three repeat batches of 5-azacytidine final product were <0.1 ppm, <0.1 ppm, and 0.14 ppm, respectively. For 5-azacytidine obtained from the ferric chloride route, the iron contents in three repeat batches of 5-azacytidine final product were <0.1 ppm, <0.1 ppm, and <0.1 ppm, respectively.

2. 5-Azacytidine Mono-Hydrochloride Salt $^1$H NMR (DMSO-d$_6$) δ 9.86 (s, 1H), 8.94 (s, 2H), 8.91 (s, 1H), 5.58 (d, 1H, J=1.4 Hz), 4.12 (m, 1H), 4.05 (m, 1H), 3.90 (m, 1H), 3.76 (m, 1H), 3.59 (m, 1H).

$^{13}$C NMR (DMSO-d$_6$) δ 160.3, 158.3, 146.6, 90.7, 84.5, 74.2, 68.0, 59.2.

LC-MS ESI: m/z 245.2 (M+H$^+$).

Figure 7:
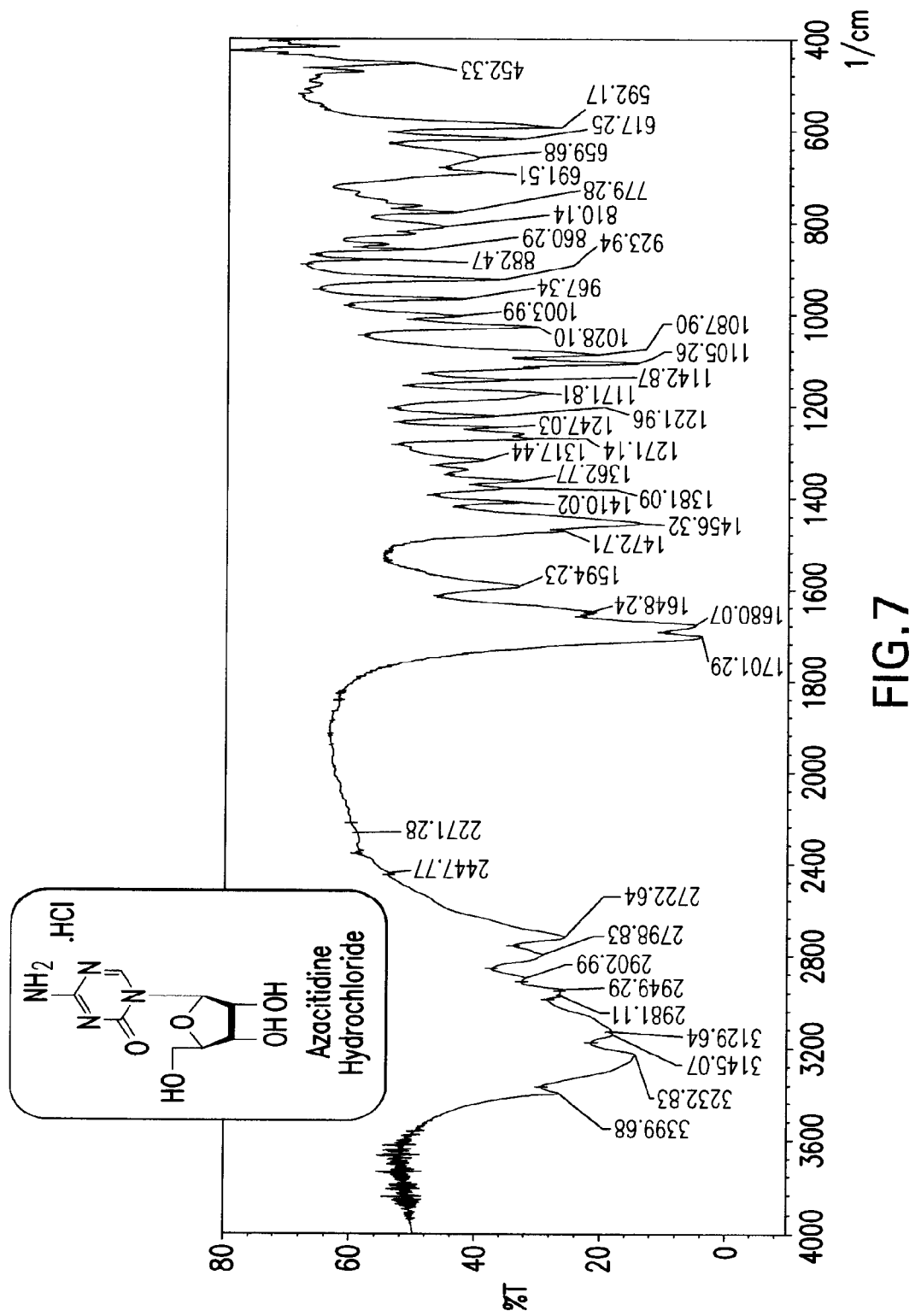
FIG. 7 represents an IR spectrum of a 5-azacytidine mono-hydrochloride salt.
Figure 8:
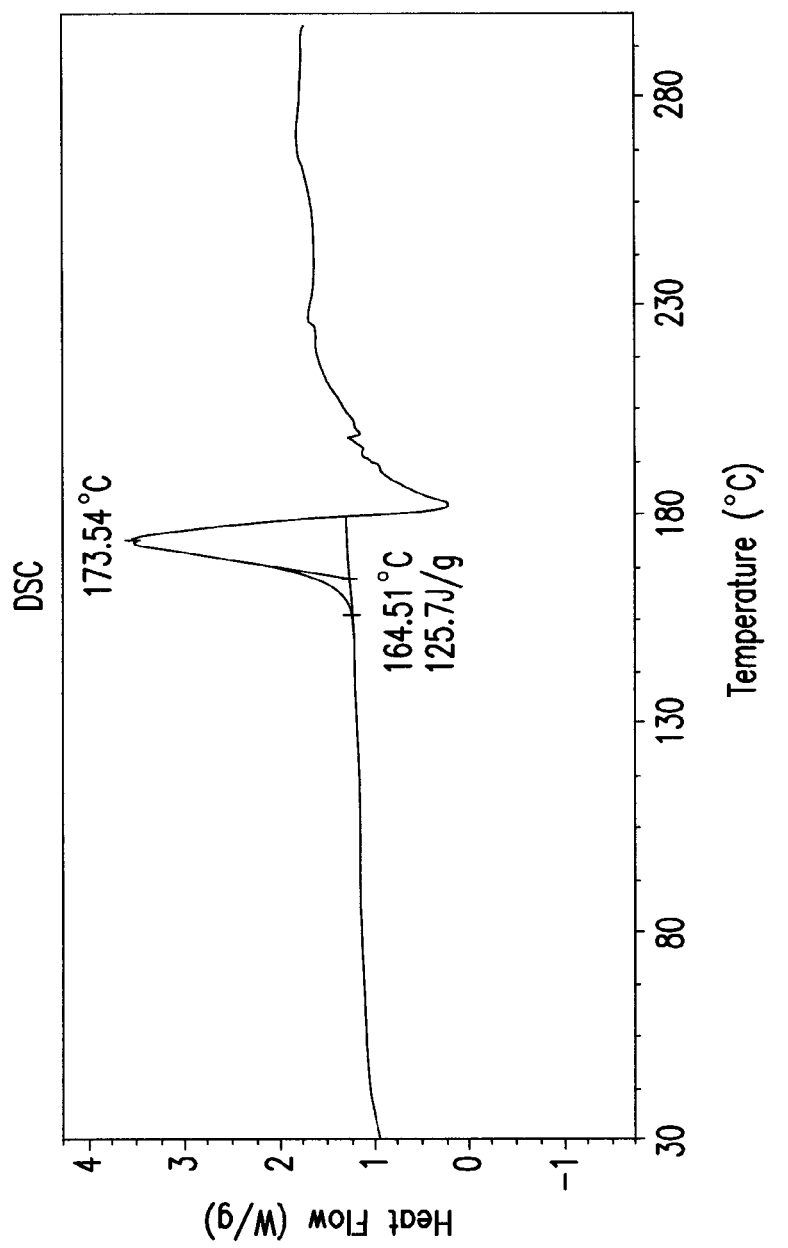
FIG. 8 represents a DSC plot of the a 5-azacytidine mono-hydrochloride salt.
Figure 9:
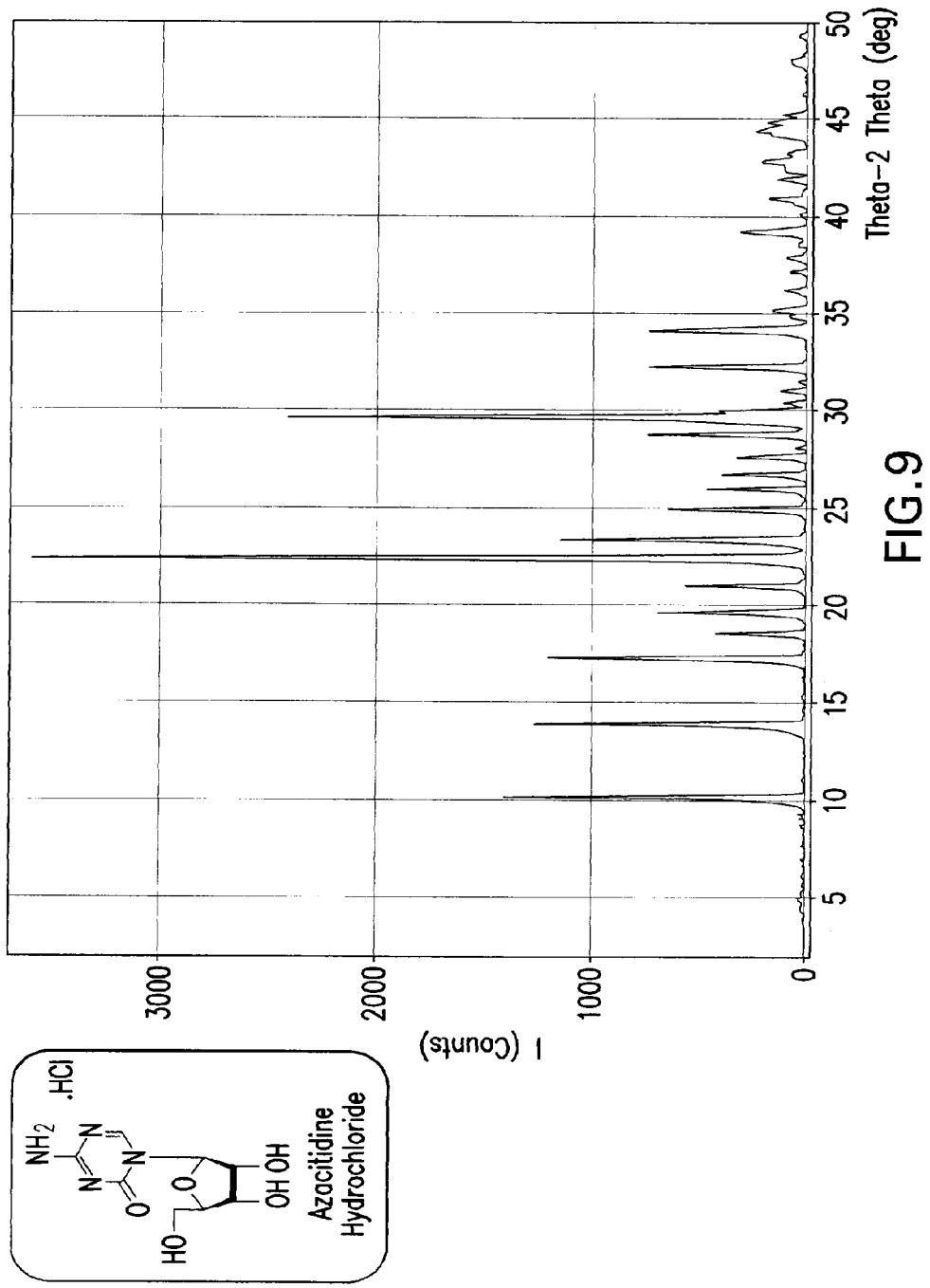
FIG. 9 represents an XRPD pattern of a 5-azacytidine mono-hydrochloride salt.
Figure 10:
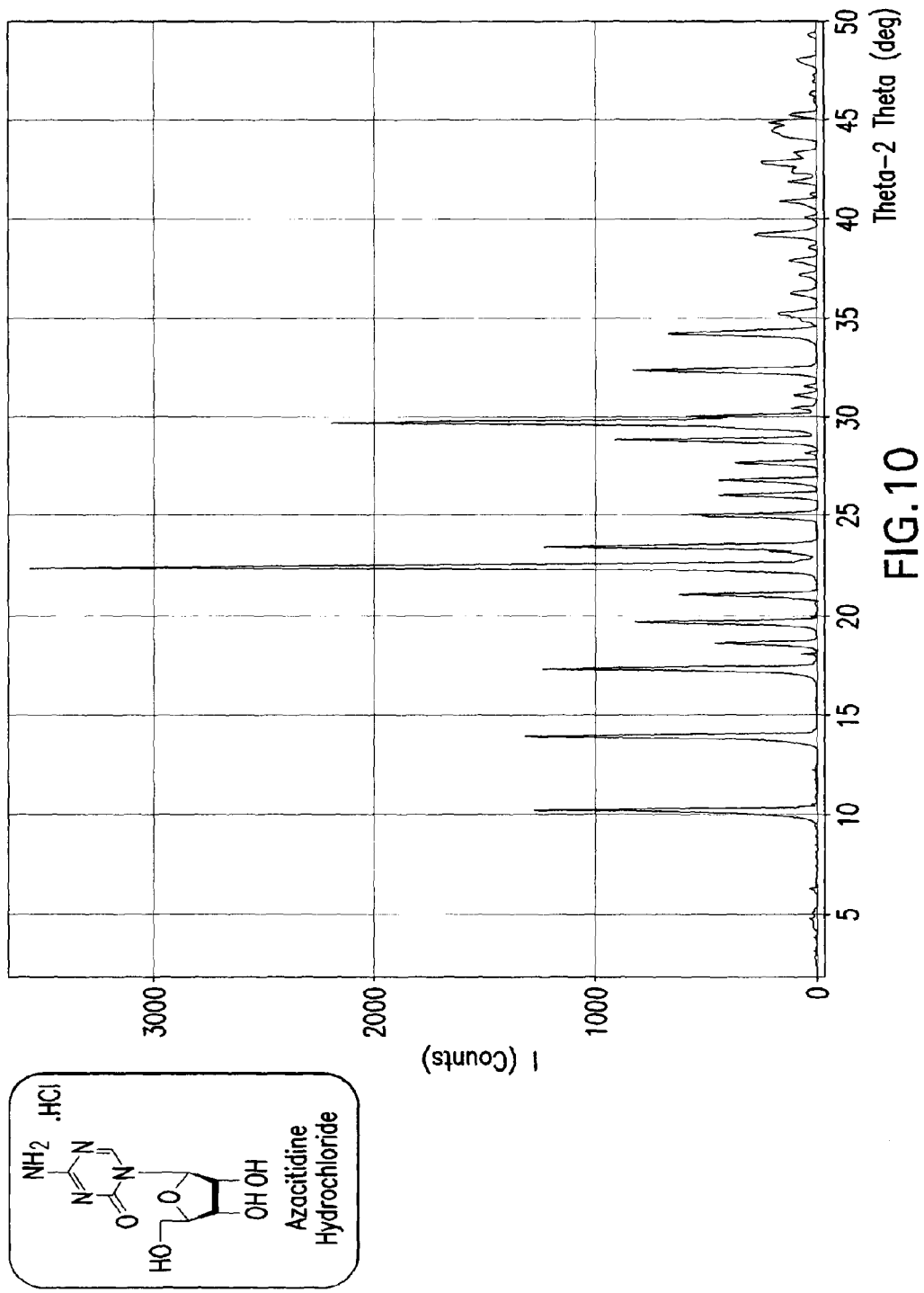
FIG. 10 represents an XRPD pattern of a 5-azacytidine mono-hydrochloride salt.

The IR spectrum of 5-azacytidine mono-hydrochloride salt is shown in FIG. 7; the DSC plot of 5-azacytidine mono-hydrochloride salt is shown in FIG. 8. For 5-azacytidine mono-hydrochloride salt obtained from the stannic chloride route, the XRPD pattern is shown in FIG. 9. For 5-azacytidine mono-hydrochloride salt obtained from the ferric chloride route, the XRPD pattern is shown in FIG. 10. The XRPD data are further provided in the tables below:

TABLE 23

XRPD (Stannic Chloride Route) - Strongest 3 peaks

| Peak no. | Peak no. | 2Theta (deg) | d (A) | I/I1 | FWHM (deg) | Intensity (Counts) | Integrated Int (Counts) |
|---|---|---|---|---|---|---|---|
| 1 | 10 | 22.4151 | 3.96319 | 100 | 0.16700 | 2575 | 23714 |
| 2 | 19 | 29.6437 | 3.01117 | 70 | 0.17140 | 1806 | 16497 |
| 3 | 1 | 10.1820 | 8.68063 | 38 | 0.15390 | 967 | 9694 |

TABLE 24

XRPD (Stannic Chloride Route) - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 10.1820 | 8.68063 | 38 | 0.15390 | 967 | 9694 |
| 2 | 13.5600 | 6.52479 | 3 | 0.16000 | 81 | 1615 |
| 3 | 13.8880 | 6.37142 | 34 | 0.15420 | 886 | 7580 |

TABLE 24-continued

XRPD (Stannic Chloride Route) - Peak Data List

| Peak no. | 2Theta (deg) | d (A) | I/I1 | FWHM (deg) | Intensity (Counts) | Integrated Int (Counts) |
|---|---|---|---|---|---|---|
| 4 | 17.2906 | 5.12450 | 32 | 0.17580 | 836 | 8843 |
| 5 | 18.5819 | 4.77120 | 12 | 0.17910 | 298 | 3115 |
| 6 | 19.4600 | 4.55784 | 4 | 0.10820 | 102 | 912 |
| 7 | 19.6480 | 4.51465 | 19 | 0.17090 | 495 | 4403 |
| 8 | 21.0139 | 4.22418 | 16 | 0.15630 | 406 | 3852 |
| 9 | 22.1200 | 4.01539 | 6 | 0.14120 | 163 | 2682 |
| 10 | 22.4151 | 3.96319 | 100 | 0.16700 | 2575 | 23714 |
| 11 | 23.3341 | 3.80914 | 32 | 0.17430 | 822 | 8661 |
| 12 | 24.9266 | 3.56927 | 18 | 0.18980 | 464 | 5140 |
| 13 | 25.9609 | 3.42937 | 13 | 0.14690 | 342 | 2980 |
| 14 | 26.7005 | 3.33603 | 11 | 0.16860 | 290 | 2812 |
| 15 | 27.5877 | 3.23073 | 9 | 0.17970 | 230 | 2320 |
| 16 | 28.7607 | 3.10157 | 22 | 0.17130 | 556 | 5415 |
| 17 | 29.2000 | 3.05590 | 3 | 0.11360 | 80 | 557 |
| 18 | 29.3400 | 3.04164 | 10 | 0.15880 | 269 | 2565 |
| 19 | 29.6437 | 3.01117 | 70 | 0.17140 | 1806 | 16497 |
| 20 | 29.9278 | 2.98323 | 16 | 0.18500 | 416 | 4216 |
| 21 | 30.3686 | 2.94092 | 3 | 0.19730 | 83 | 862 |
| 22 | 31.0303 | 2.87970 | 3 | 0.18460 | 87 | 1019 |
| 23 | 32.2457 | 2.77388 | 22 | 0.16050 | 565 | 5201 |
| 24 | 34.1244 | 2.62534 | 21 | 0.23380 | 549 | 7173 |
| 25 | 35.0000 | 2.56164 | 3 | 0.18660 | 81 | 1120 |
| 26 | 35.1400 | 2.55175 | 5 | 0.25500 | 121 | 1271 |
| 27 | 38.9800 | 2.30876 | 4 | 0.11600 | 104 | 619 |
| 28 | 39.1250 | 2.30054 | 9 | 0.25000 | 239 | 2803 |
| 29 | 40.8414 | 2.20773 | 5 | 0.18940 | 138 | 1917 |
| 30 | 41.8511 | 2.15677 | 4 | 0.20630 | 102 | 1137 |
| 31 | 42.2800 | 2.13588 | 3 | 0.15140 | 80 | 1171 |
| 32 | 42.5000 | 2.12533 | 3 | 0.00000 | 83 | 0 |
| 33 | 42.7600 | 2.11301 | 6 | 0.19640 | 165 | 1745 |
| 34 | 42.9000 | 2.10643 | 5 | 0.16200 | 122 | 940 |
| 35 | 43.2009 | 2.09246 | 3 | 0.24180 | 77 | 949 |
| 36 | 44.0600 | 2.05363 | 4 | 0.21240 | 104 | 1331 |
| 37 | 44.1800 | 2.04833 | 5 | 0.00000 | 125 | 0 |
| 38 | 44.3800 | 2.03956 | 7 | 0.00000 | 180 | 0 |
| 39 | 44.6000 | 2.03001 | 4 | 0.00000 | 95 | 0 |
| 40 | 44.8044 | 2.02122 | 6 | 0.18660 | 153 | 1761 |
| 41 | 45.2044 | 2.00426 | 3 | 0.20520 | 86 | 927 |

TABLE 25

XRPD (Ferric Chloride Route) - Strongest 3 peaks

| no. | Peak no. | 2Theta (deg) | d (A) | I/I1 | FWHM (deg) | Intensity (Counts) | Integrated Int (Counts) |
|---|---|---|---|---|---|---|---|
| 1 | 9 | 22.4639 | 3.95469 | 100 | 0.16700 | 2537 | 23682 |
| 2 | 17 | 29.6916 | 3.00642 | 65 | 0.17360 | 1647 | 14121 |
| 3 | 3 | 13.9291 | 6.35272 | 36 | 0.16820 | 916 | 9501 |

TABLE 26

XRPD (Ferric Chloride Route) - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 9.8800 | 8.94528 | 3 | 0.18000 | 77 | 1671 |
| 2 | 10.2256 | 8.64371 | 34 | 0.16640 | 870 | 7850 |
| 3 | 13.9291 | 6.35272 | 36 | 0.16820 | 916 | 9501 |
| 4 | 17.3347 | 5.11156 | 34 | 0.18500 | 851 | 9333 |
| 5 | 18.6294 | 4.75914 | 13 | 0.17450 | 326 | 3241 |
| 6 | 19.6938 | 4.50426 | 23 | 0.17410 | 585 | 5889 |
| 7 | 21.0636 | 4.21433 | 18 | 0.15630 | 447 | 4150 |
| 8 | 22.1400 | 4.01181 | 4 | 0.13200 | 93 | 1691 |
| 9 | 22.4639 | 3.95469 | 100 | 0.16720 | 2537 | 23682 |
| 10 | 23.3813 | 3.80156 | 34 | 0.17920 | 874 | 9272 |
| 11 | 24.9741 | 3.56259 | 18 | 0.17900 | 465 | 4759 |
| 12 | 26.0052 | 3.42363 | 13 | 0.16080 | 328 | 3022 |
| 13 | 26.7511 | 3.32984 | 13 | 0.14980 | 335 | 2995 |
| 14 | 27.6414 | 3.22457 | 11 | 0.17420 | 272 | 2656 |
| 15 | 28.8062 | 3.09678 | 27 | 0.16880 | 688 | 6568 |
| 16 | 29.4200 | 3.03355 | 12 | 0.18700 | 315 | 3812 |
| 17 | 29.6916 | 3.00642 | 65 | 0.17360 | 1647 | 14121 |
| 18 | 29.9843 | 2.97773 | 17 | 0.18330 | 439 | 4665 |
| 19 | 30.4169 | 2.93636 | 4 | 0.16390 | 93 | 917 |
| 20 | 31.0784 | 2.87535 | 3 | 0.15680 | 87 | 882 |
| 21 | 32.2948 | 2.76977 | 26 | 0.16090 | 651 | 6016 |
| 22 | 34.1649 | 2.62232 | 19 | 0.24330 | 491 | 6587 |
| 23 | 35.0400 | 2.55881 | 3 | 0.16660 | 84 | 1159 |
| 24 | 35.2000 | 2.54754 | 5 | 0.23140 | 124 | 1328 |
| 25 | 36.2228 | 2.47792 | 3 | 0.22960 | 86 | 1220 |
| 26 | 37.8751 | 2.37353 | 4 | 0.22680 | 96 | 1184 |
| 27 | 39.1998 | 2.29632 | 8 | 0.24830 | 207 | 3189 |
| 28 | 40.8791 | 2.20578 | 5 | 0.16480 | 139 | 1711 |
| 29 | 41.8962 | 2.15455 | 4 | 0.21640 | 102 | 1131 |
| 30 | 42.3800 | 2.13107 | 4 | 0.17720 | 93 | 1161 |
| 31 | 42.8537 | 2.10860 | 8 | 0.27740 | 196 | 2950 |
| 32 | 43.2513 | 2.09014 | 3 | 0.22840 | 82 | 965 |
| 33 | 44.1000 | 2.05186 | 5 | 0.20280 | 117 | 2531 |
| 34 | 44.4000 | 2.03869 | 6 | 0.00000 | 152 | 0 |
| 35 | 44.6000 | 2.03001 | 5 | 0.00000 | 124 | 0 |
| 36 | 44.8398 | 2.01971 | 7 | 0.19340 | 179 | 2303 |
| 37 | 45.2368 | 2.00290 | 5 | 0.15160 | 116 | 967 |

3. 5-Azacytidine Hemisulfate Salt Methanol Solvate $^{1}$H NMR (DMSO-$d_6$) δ 8.76 (s, 1H), 8.69 (s, 1H), 8.25 (s, 1H), 5.61 (d, 1H, J=2.4 Hz), 4.09 (m, 1H), 4.02 (m, 1H), 3.87 (m, 1H), 3.72 (m, 1H), 3.57 (m, 1H), 3.14 (s, 3H) (CH$_3$OH).

$^{13}$C NMR (DMSO-$d_6$) δ 162.8, 157.5, 150.2, 90.2, 84.5, 74.2, 68.5, 59.7, 48.9 (CH$_3$OH).

LC-MS ESI: m/z 245.2 (M+H$^+$).

Figure 11:
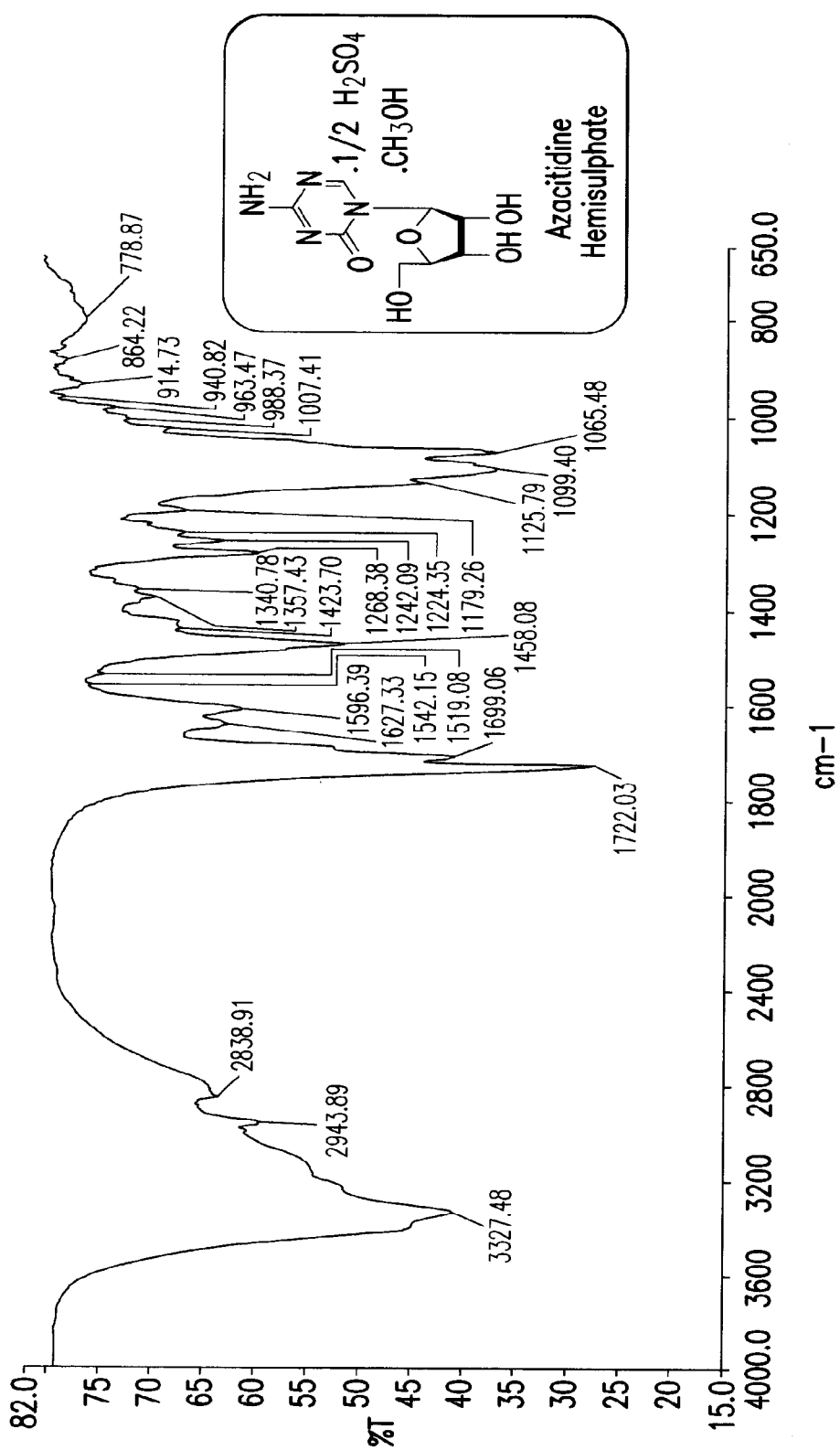
FIG. 11 represents an IR spectrum of a methanol solvate of 5-azacytidine hemisulfate salt.
Figure 12:
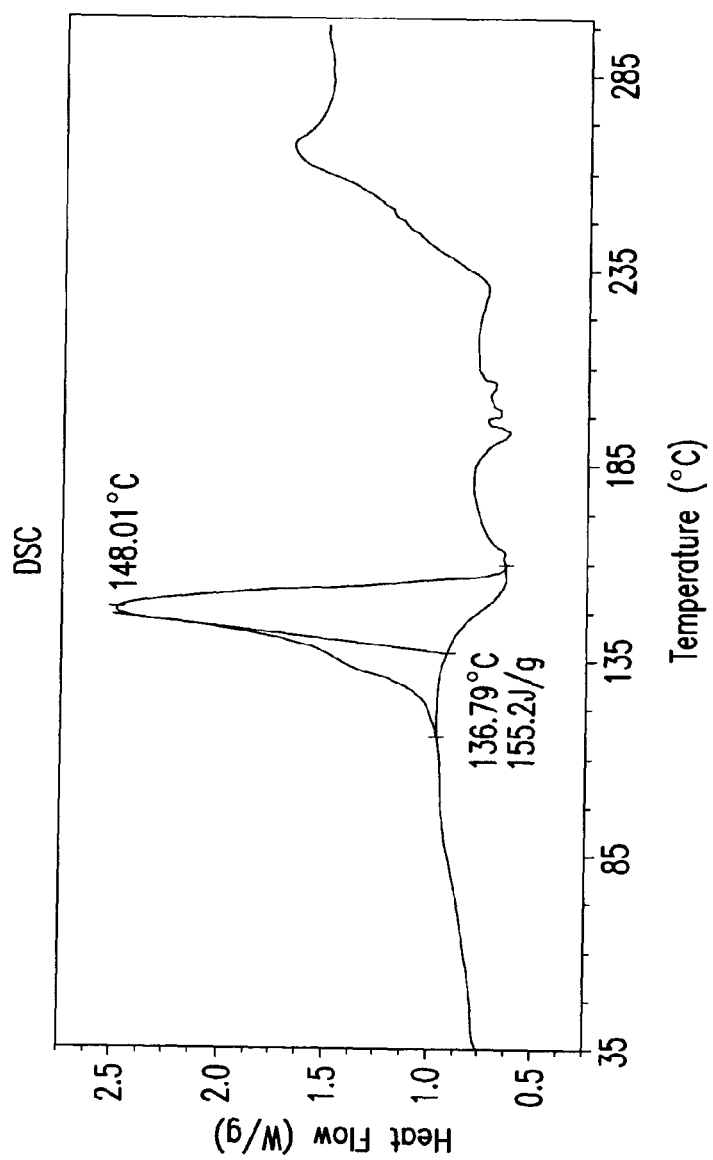
FIG. 12 represents a DSC plot of a methanol solvate of 5-azacytidine hemisulfate salt.
Figure 12:
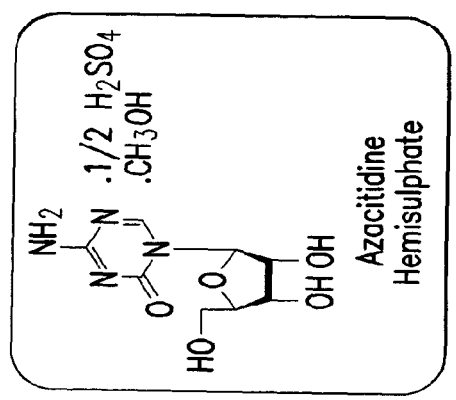
Figure 13:
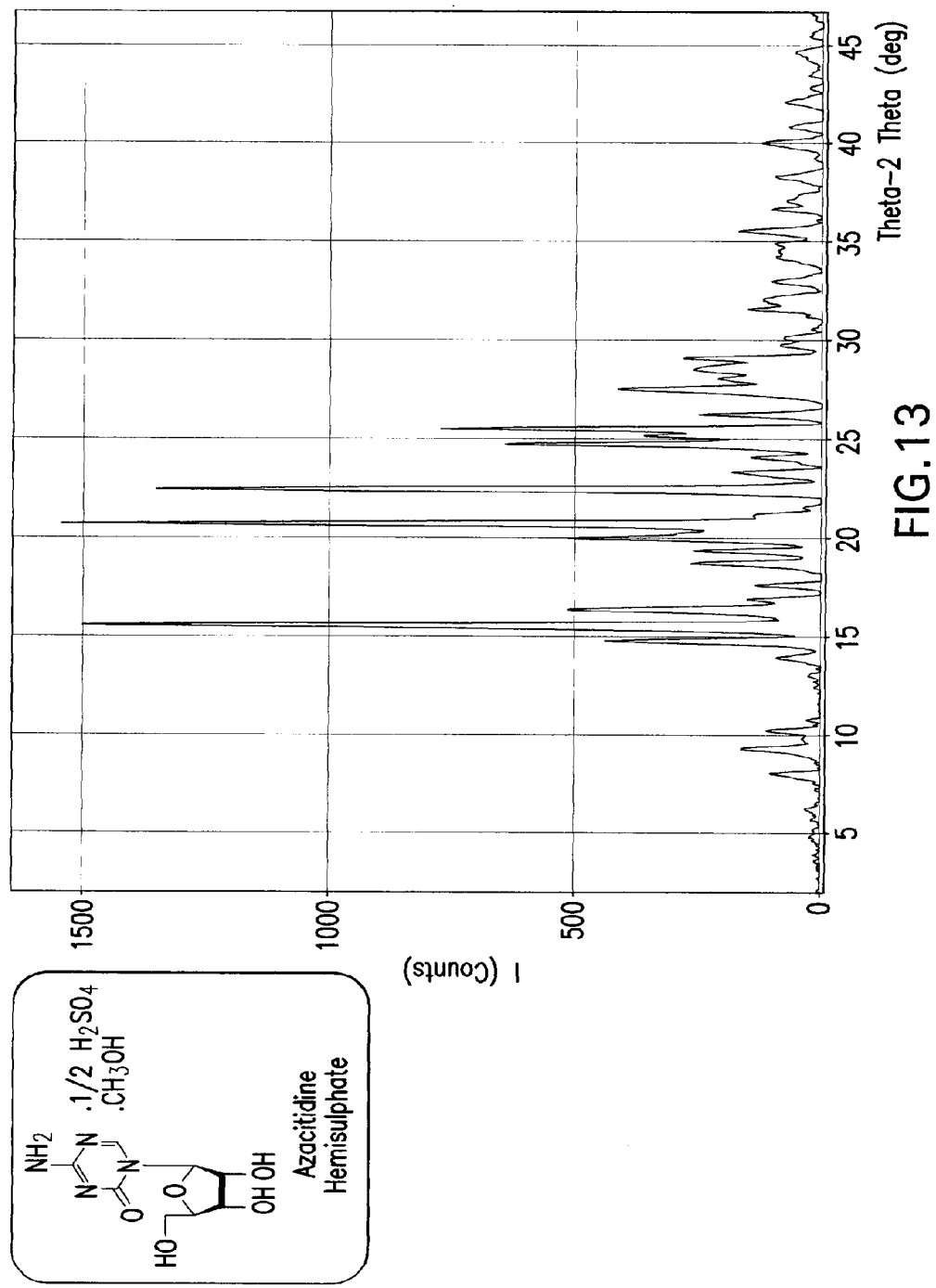
FIG. 13 represents an XRPD pattern of a methanol solvate of 5-azacytidine hemisulfate salt.

The IR spectrum of 5-azacytidine hemisulfate salt methanol solvate is shown in FIG. 11; the DSC plot of 5-azacytidine hemisulfate salt methanol solvate is shown in FIG. 12. The XRPD pattern of 5-azacytidine hemisulfate salt methanol solvate is shown in FIG. 13. The XRPD data is further provided in the table below:

TABLE 27

XRPD - Strongest 3 peaks

| no. | Peak no. | 2Theta (deg) | d (A) | I/I1 | FWHM (deg) | Intensity (Counts) | Integrated Int (Counts) |
|---|---|---|---|---|---|---|---|
| 1 | 15 | 20.7054 | 4.28642 | 100 | 0.24550 | 1073 | 14977 |
| 2 | 7 | 15.5303 | 5.70116 | 95 | 0.27540 | 1014 | 15758 |
| 3 | 17 | 22.4492 | 3.95725 | 87 | 0.25300 | 937 | 13242 |

TABLE 28

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 7.7800 | 11.35446 | 3 | 0.18660 | 35 | 484 |
| 2 | 8.0200 | 11.01521 | 7 | 0.20000 | 70 | 752 |
| 3 | 9.2841 | 9.51805 | 10 | 0.32170 | 111 | 2488 |

TABLE 28-continued

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 4 | 10.2184 | 8.64979 | 7 | 0.27690 | 75 | 1498 |
| 5 | 13.8860 | 6.37234 | 6 | 0.33200 | 61 | 1289 |
| 6 | 14.7439 | 6.00342 | 28 | 0.30600 | 299 | 5182 |
| 7 | 15.5303 | 5.70116 | 95 | 0.27540 | 1014 | 15758 |
| 8 | 16.3058 | 5.43172 | 33 | 0.33420 | 351 | 6494 |
| 9 | 16.8200 | 5.26680 | 10 | 0.26340 | 105 | 1672 |
| 10 | 17.5682 | 5.04415 | 9 | 0.22980 | 93 | 1144 |
| 11 | 18.6876 | 4.74445 | 17 | 0.31930 | 183 | 3260 |
| 12 | 19.3369 | 4.58658 | 17 | 0.24440 | 179 | 2462 |
| 13 | 19.9800 | 4.44038 | 33 | 0.30820 | 350 | 6176 |
| 14 | 20.2200 | 4.38821 | 19 | 0.00000 | 203 | 0 |
| 15 | 20.7054 | 4.28642 | 100 | 0.24550 | 1073 | 14977 |
| 16 | 21.0800 | 4.21109 | 9 | 0.42660 | 99 | 3355 |
| 17 | 22.4492 | 3.95725 | 87 | 0.25300 | 937 | 13242 |
| 18 | 23.0800 | 3.85050 | 7 | 0.19000 | 75 | 834 |
| 19 | 23.3000 | 3.81464 | 12 | 0.26880 | 130 | 1613 |
| 20 | 24.0475 | 3.69773 | 9 | 0.27910 | 100 | 1609 |
| 21 | 24.4200 | 3.64216 | 7 | 0.16000 | 77 | 869 |
| 22 | 24.7239 | 3.59808 | 42 | 0.26190 | 448 | 5628 |
| 23 | 25.1600 | 3.53669 | 23 | 0.34900 | 250 | 4362 |
| 24 | 25.5017 | 3.49007 | 51 | 0.23860 | 542 | 6193 |
| 25 | 26.2202 | 3.39604 | 16 | 0.23670 | 176 | 2431 |
| 26 | 27.0600 | 3.29252 | 4 | 0.17000 | 45 | 730 |
| 27 | 27.4793 | 3.24323 | 26 | 0.35370 | 284 | 6993 |
| 28 | 28.0400 | 3.17963 | 14 | 0.00000 | 151 | 0 |
| 29 | 28.4200 | 3.13798 | 17 | 0.00000 | 180 | 0 |
| 30 | 29.0313 | 3.07328 | 19 | 0.29870 | 208 | 6146 |
| 31 | 29.7535 | 3.00030 | 5 | 0.40710 | 59 | 1075 |
| 32 | 30.1250 | 2.96415 | 5 | 0.33000 | 57 | 1037 |
| 33 | 31.6000 | 2.82907 | 10 | 0.28000 | 107 | 2309 |
| 34 | 31.9600 | 2.79802 | 8 | 0.00000 | 82 | 0 |
| 35 | 32.1200 | 2.78445 | 8 | 0.47560 | 83 | 1624 |
| 36 | 32.9980 | 2.71234 | 7 | 0.31600 | 72 | 1298 |
| 37 | 34.1600 | 2.62268 | 6 | 0.35200 | 65 | 1547 |
| 38 | 34.4200 | 2.60347 | 6 | 0.00000 | 60 | 0 |
| 39 | 34.8400 | 2.57304 | 7 | 0.32000 | 70 | 1862 |
| 40 | 35.4883 | 2.52750 | 12 | 0.32790 | 126 | 2292 |
| 41 | 36.6527 | 2.44984 | 7 | 0.23680 | 78 | 886 |
| 42 | 37.0600 | 2.42384 | 5 | 0.37200 | 50 | 855 |
| 43 | 37.3600 | 2.40507 | 3 | 0.24500 | 37 | 481 |
| 44 | 38.2516 | 2.35103 | 7 | 0.29670 | 70 | 1353 |
| 45 | 39.6800 | 2.26963 | 4 | 0.16800 | 40 | 453 |
| 46 | 39.9326 | 2.25585 | 8 | 0.45730 | 85 | 1544 |
| 47 | 40.8125 | 2.20923 | 5 | 0.33500 | 53 | 867 |

4. 5-Azacytidine Mesylate Salt Methanol Solvate $^1$H NMR (DMSO-$d_6$) δ 9.74 (s, 1H), 9.07 (s, 1H), 8.94 (s, 1H), 5.58 (d, 1H, J=0.9 Hz), 4.11 (m, 1H), 4.05 (m, 1H), 3.90 (m, 1H), 3.78 (m, 1H), 3.59 (m, 1H), 3.15 (s, 3H) (CH$_3$OH), 2.49 (s, 3H) (CH$_3$SO$_3$H).

$^{13}$C NMR (DMSO-$d_6$) δ 160.0, 158.3, 146.9, 90.7, 84.4, 74.2, 67.9, 59.2, 48.9 (CH$_3$OH), 40.0 (CH$_3$SO$_3$H).

LC-MS ESI: m/z 245.2 (M+H$^+$).

Figure 14:
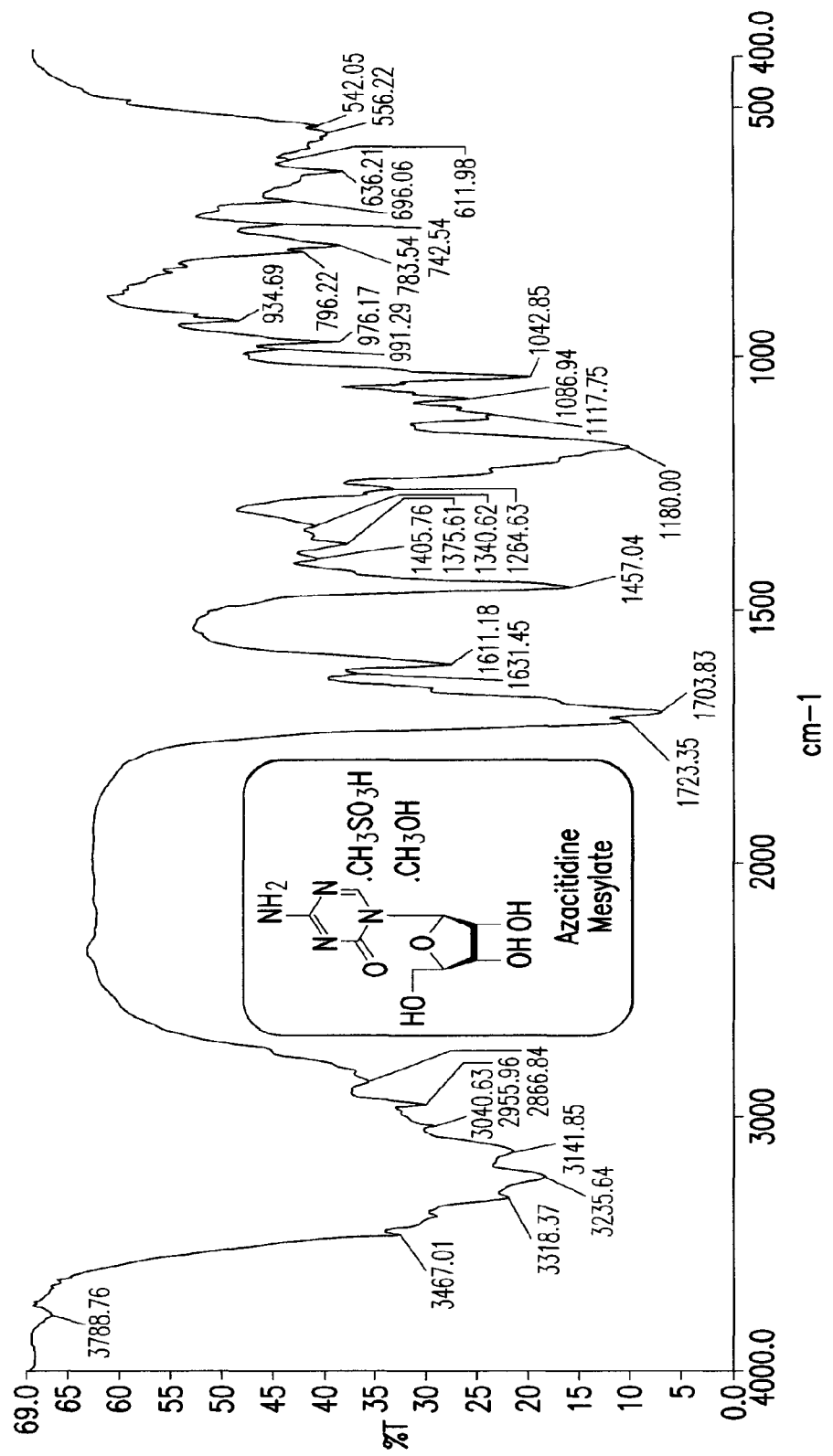
FIG. 14 represents an IR spectrum of a methanol solvate of 5-azacytidine mesylate salt.
Figure 15:
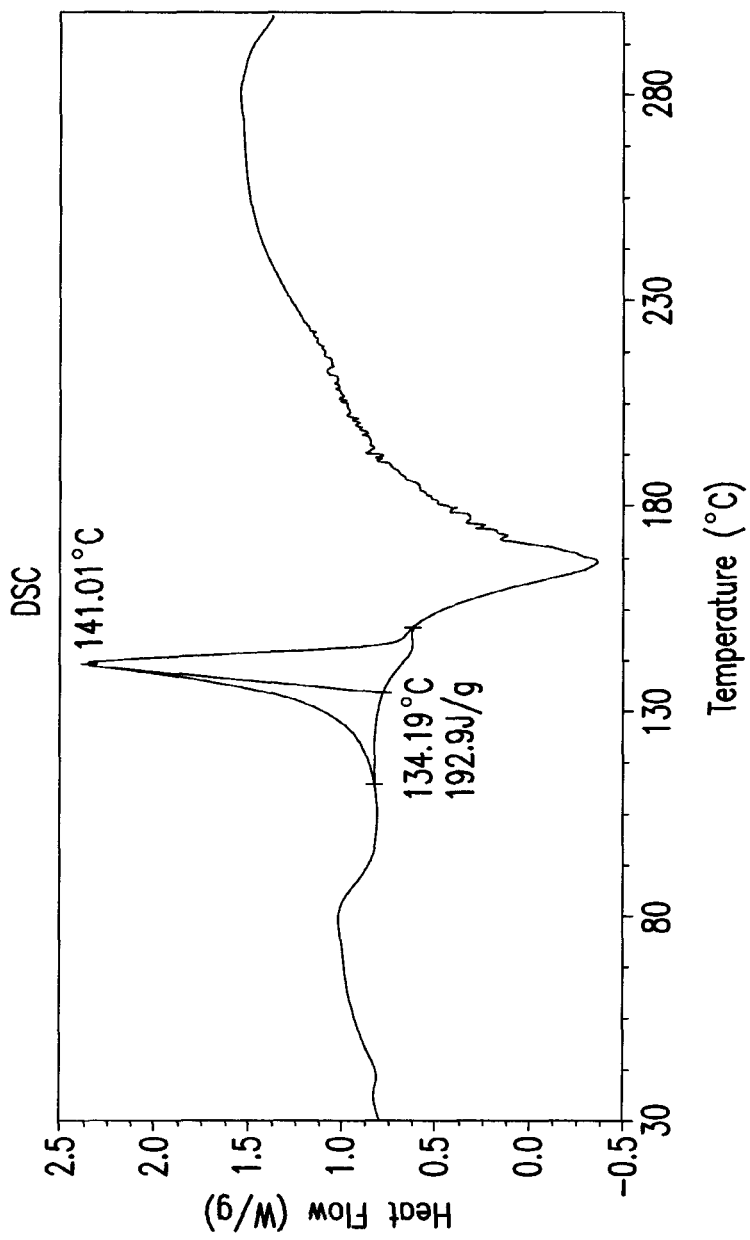
FIG. 15 represents a DSC plot of a methanol solvate of 5-azacytidine mesylate salt.
Figure 15:
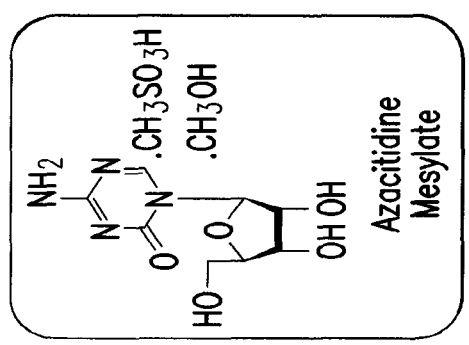
Figure 16:
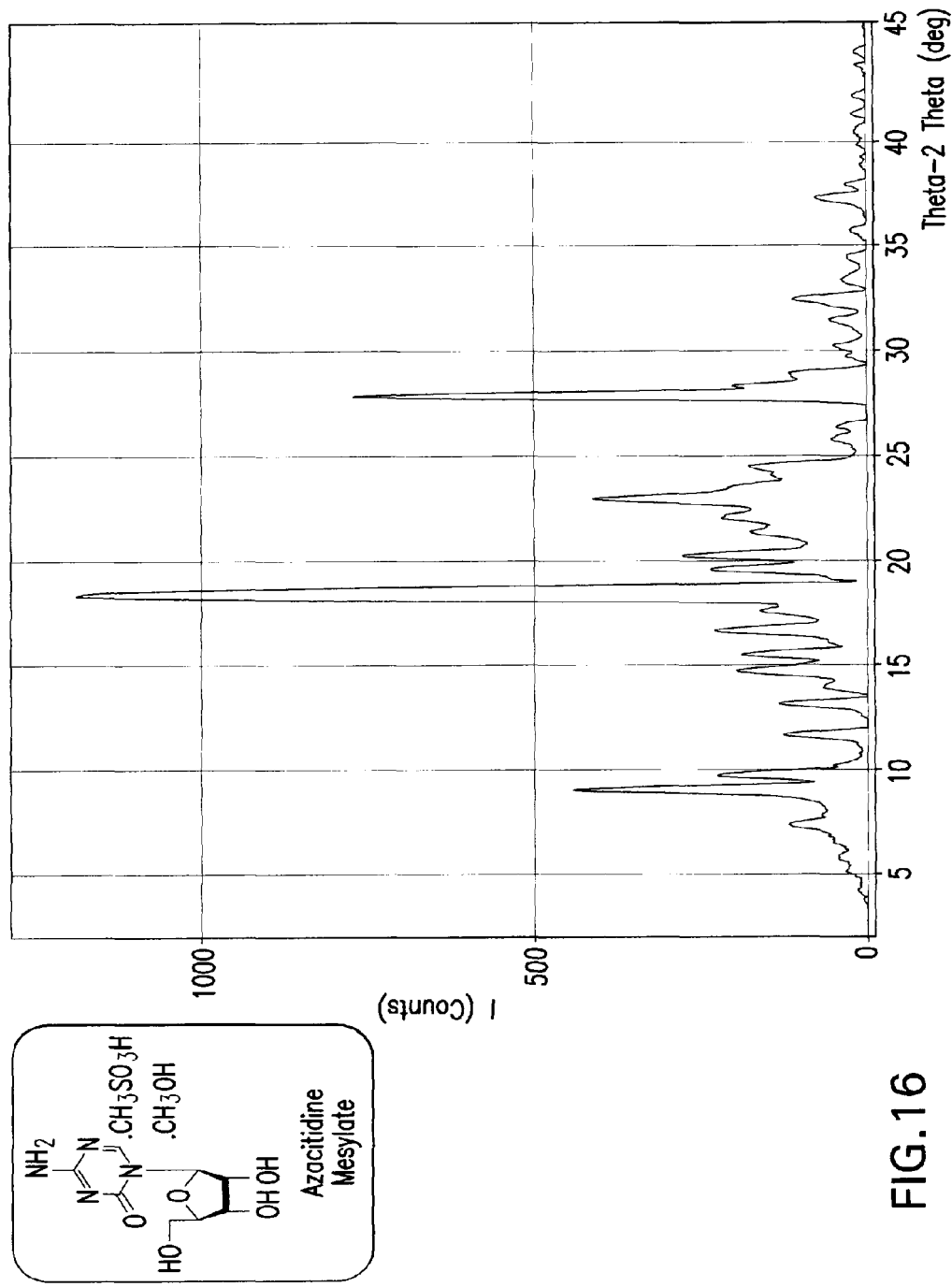
FIG. 16 represents an XRPD pattern of a methanol solvate of 5-azacytidine mesylate salt.

The IR spectrum of 5-azacytidine mesylate salt methanol solvate is shown in FIG. 14; the DSC plot of 5-azacytidine mesylate salt methanol solvate is shown in FIG. 15. The XRPD pattern of 5-azacytidine mesylate salt methanol solvate is shown in FIG. 16. The XRPD data is further provided in the table below:

TABLE 29

XRPD - Strongest 3 peaks

| Peak no. | Peak no. | 2Theta (deg) | d (A) | I/I1 | FWHM (deg) | Intensity (Counts) | Integrated Int (Counts) |
|---|---|---|---|---|---|---|---|
| 1 | 14 | 18.4114 | 4.81500 | 100 | 0.71380 | 796 | 27178 |
| 2 | 24 | 27.8449 | 3.20147 | 66 | 0.40900 | 527 | 11554 |
| 3 | 5 | 9.0287 | 9.78671 | 38 | 0.43740 | 299 | 7573 |

TABLE 30

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 5.1200 | 17.24595 | 3 | 0.36000 | 24 | 1341 |
| 2 | 5.8400 | 15.12125 | 4 | 0.00000 | 31 | 0 |
| 3 | 6.4800 | 13.62916 | 5 | 0.00000 | 36 | 0 |
| 4 | 7.3400 | 12.03410 | 10 | 0.74660 | 81 | 4815 |
| 5 | 9.0287 | 9.78671 | 38 | 0.43740 | 299 | 7573 |
| 6 | 9.7322 | 9.08079 | 19 | 0.50890 | 152 | 4481 |
| 7 | 11.6904 | 7.56374 | 11 | 0.39420 | 87 | 1951 |
| 8 | 13.1008 | 6.75245 | 11 | 0.37830 | 91 | 1818 |
| 9 | 13.8600 | 6.38423 | 6 | 0.32800 | 48 | 1041 |
| 10 | 14.7266 | 6.01044 | 17 | 0.62670 | 134 | 4254 |
| 11 | 15.5183 | 5.70554 | 16 | 0.46160 | 131 | 3257 |
| 12 | 16.6612 | 5.31664 | 20 | 0.49250 | 156 | 4279 |
| 13 | 17.5600 | 5.04649 | 14 | 0.76000 | 112 | 4315 |
| 14 | 18.4114 | 4.81500 | 100 | 0.71380 | 796 | 27178 |
| 15 | 19.5860 | 4.52880 | 20 | 0.50300 | 160 | 4059 |
| 16 | 20.2466 | 4.38250 | 24 | 0.50670 | 190 | 4721 |
| 17 | 21.3800 | 4.15267 | 15 | 1.12000 | 122 | 6951 |
| 18 | 22.0200 | 4.03340 | 19 | 0.00000 | 149 | 0 |
| 19 | 23.0149 | 3.86124 | 35 | 0.79870 | 280 | 12958 |
| 20 | 23.5000 | 3.78262 | 18 | 0.00000 | 143 | 0 |
| 21 | 24.5000 | 3.63045 | 15 | 0.42000 | 122 | 6939 |
| 22 | 25.8160 | 3.44829 | 5 | 0.51200 | 39 | 1204 |
| 23 | 26.3750 | 3.37646 | 5 | 0.45000 | 36 | 649 |
| 24 | 27.8449 | 3.20147 | 66 | 0.40900 | 527 | 11664 |
| 25 | 28.8800 | 3.08903 | 10 | 0.45000 | 80 | 3453 |
| 26 | 29.7000 | 3.00559 | 3 | 0.24000 | 26 | 377 |
| 27 | 30.1800 | 2.95887 | 5 | 0.46000 | 36 | 929 |
| 28 | 31.4515 | 2.84209 | 5 | 0.47300 | 42 | 1195 |
| 29 | 32.4275 | 2.75874 | 10 | 0.57500 | 78 | 2146 |
| 30 | 33.4000 | 2.68060 | 4 | 0.56000 | 29 | 1319 |
| 31 | 37.2825 | 2.40989 | 7 | 0.41500 | 55 | 1282 |
| 32 | 37.8893 | 2.37268 | 3 | 0.24530 | 27 | 410 |

5. 5-Azacytidine Mono-Hydrobromide Salt $^1$H NMR (DMSO-$d_6$) δ 9.50 (s, 1H), 8.91 (s, 1H), 8.56 (s, 1H), 5.60 (d, 1H, J=1.7 Hz), 4.12 (m, 1H), 4.05 (m, 1H), 3.90 (m, 1H), 3.77 (m, 1H), 3.59 (m, 1H).

$^{13}$C NMR (DMSO-$d_6$) δ 160.0, 158.3, 147.0, 90.7, 84.6, 74.2, 68.1, 59.3.

LC-MS ESI: m/z 245.0 (M+H$^+$).

Figure 17:
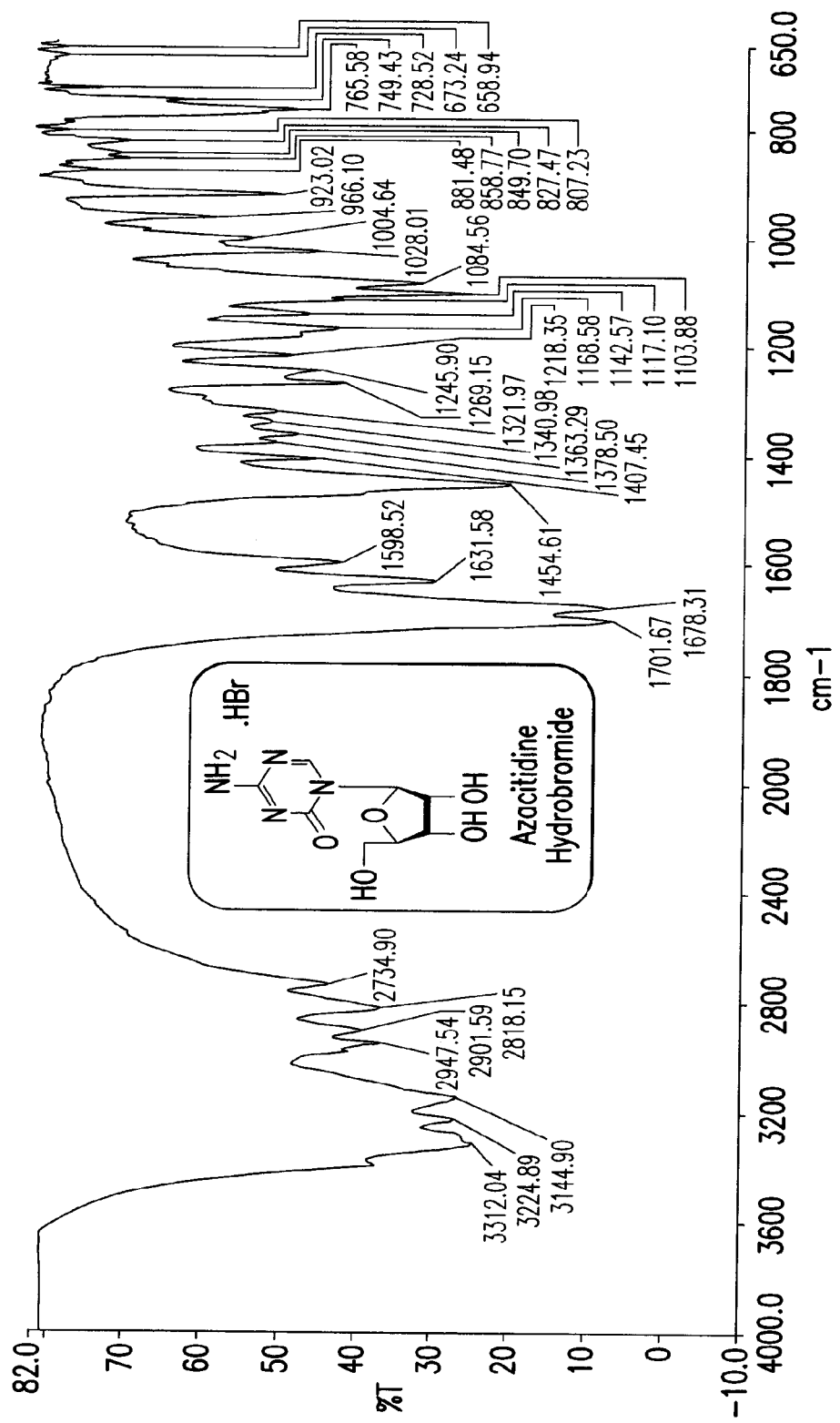
FIG. 17 represents an IR spectrum of a 5-azacytidine hydrobromide salt.
Figure 18:
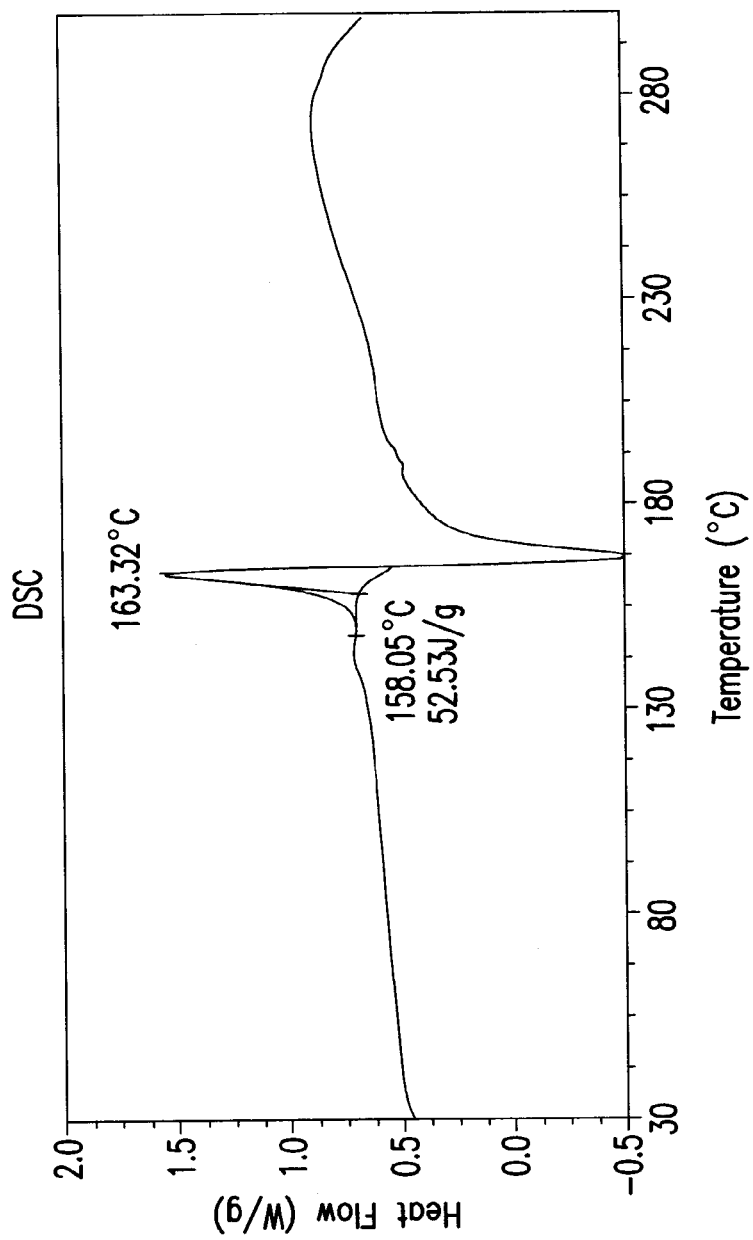
FIG. 18 represents a DSC plot of a 5-azacytidine hydrobromide salt.
Figure 18:
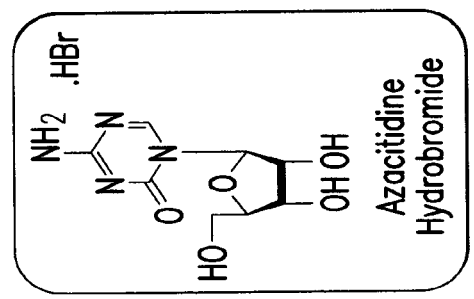
Figure 19:
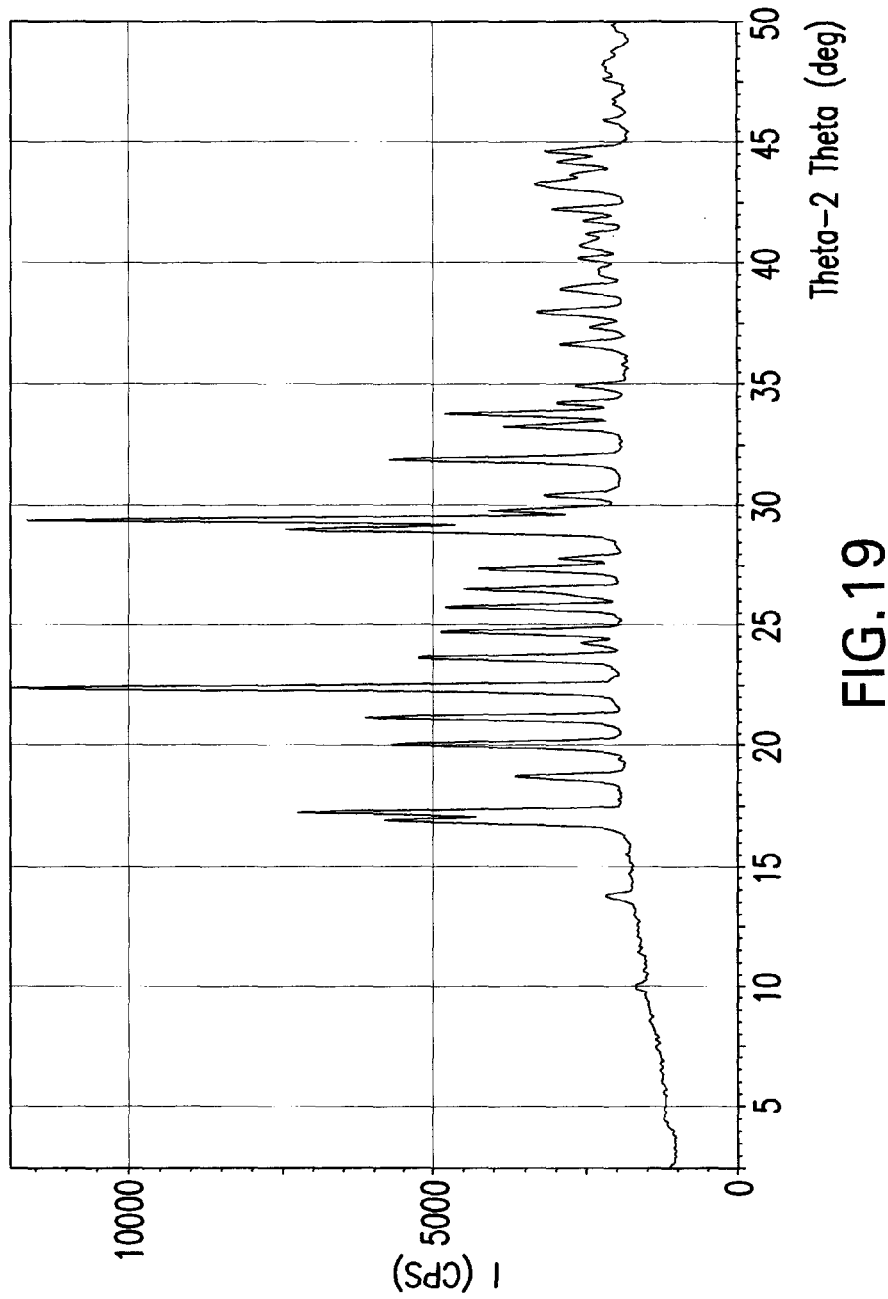
FIG. 19 represents an XRPD pattern of a 5-azacytidine hydrobromide salt.
Figure 19:
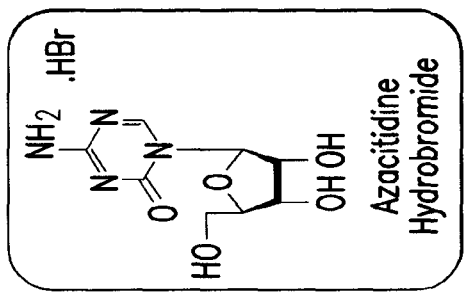

The IR spectrum of 5-azacytidine hydrobromide salt is shown in FIG. 17; the DSC plot of 5-azacytidine hydrobromide salt is shown in FIG. 18. The XRPD pattern of 5-azacytidine hydrobromide salt is shown in FIG. 19. The XRPD data is further provided in the table below:

TABLE 31

XRPD - Strongest 3 peaks

| Peak no. | Peak no. | 2Theta (deg) | d (A) | I/I1 | FWHM (deg) | Intensity (Counts) | Integrated Int (Counts) |
|---|---|---|---|---|---|---|---|
| 1 | 17 | 29.3754 | 3.03806 | 100 | 0.21090 | 3561 | 45176 |
| 2 | 7 | 22.3855 | 3.96836 | 99 | 0.23060 | 3520 | 53273 |
| 3 | 16 | 28.9891 | 3.07766 | 54 | 0.27900 | 1931 | 34036 |

TABLE 32

XRPD - Peak Data List

| Peak no. | 2Theta (deg) | d (A) | I/I1 | FWHM (deg) | Intensity (Counts) | Integrated Int (Counts) |
|---|---|---|---|---|---|---|
| 1 | 13.7653 | 6.42794 | 5 | 0.30940 | 163 | 3756 |
| 2 | 16.9160 | 5.23713 | 38 | 0.30120 | 1369 | 24687 |
| 3 | 17.2377 | 5.14011 | 52 | 0.25120 | 1867 | 26905 |
| 4 | 18.6943 | 4.74276 | 17 | 0.25010 | 623 | 10585 |
| 5 | 20.0218 | 4.43120 | 37 | 0.26200 | 1322 | 22877 |
| 6 | 21.1485 | 4.19760 | 41 | 0.23030 | 1468 | 21781 |
| 7 | 22.3855 | 3.96836 | 99 | 0.23060 | 3520 | 53273 |
| 8 | 23.6281 | 3.76240 | 33 | 0.22880 | 1160 | 17423 |
| 9 | 24.2286 | 3.67050 | 6 | 0.20170 | 212 | 2901 |
| 10 | 24.7088 | 3.60024 | 29 | 0.22290 | 1040 | 14307 |
| 11 | 25.7251 | 3.46027 | 29 | 0.20130 | 1021 | 13071 |
| 12 | 26.1470 | 3.40538 | 5 | 0.17260 | 192 | 3293 |
| 13 | 26.4765 | 3.36374 | 26 | 0.21120 | 910 | 11758 |
| 14 | 27.3328 | 3.26028 | 23 | 0.22590 | 811 | 11753 |
| 15 | 27.7680 | 3.21016 | 10 | 0.20890 | 359 | 4594 |
| 16 | 28.9891 | 3.07766 | 54 | 0.27900 | 1931 | 34036 |
| 17 | 29.3754 | 3.03806 | 100 | 0.21090 | 3561 | 45176 |
| 18 | 29.7689 | 2.99879 | 22 | 0.21720 | 776 | 10904 |
| 19 | 30.3935 | 2.93857 | 12 | 0.21880 | 443 | 6695 |
| 20 | 31.8694 | 2.80577 | 39 | 0.22910 | 1391 | 20971 |
| 21 | 33.2273 | 2.69414 | 20 | 0.20570 | 712 | 9758 |
| 22 | 33.7458 | 2.65392 | 31 | 0.20350 | 1096 | 14388 |
| 23 | 34.1908 | 2.62039 | 12 | 0.19960 | 412 | 5206 |
| 24 | 34.8996 | 2.56878 | 9 | 0.21060 | 305 | 4108 |
| 25 | 36.6147 | 2.45229 | 11 | 0.21930 | 408 | 6358 |
| 26 | 37.3233 | 2.40735 | 6 | 0.20880 | 218 | 3006 |
| 27 | 37.9283 | 2.37033 | 14 | 0.28880 | 498 | 8915 |
| 28 | 38.8907 | 2.31386 | 10 | 0.32320 | 370 | 6970 |
| 29 | 39.4410 | 2.28283 | 4 | 0.14740 | 130 | 1135 |
| 30 | 39.6960 | 2.26875 | 3 | 0.32120 | 119 | 2296 |
| 31 | 40.1470 | 2.24430 | 8 | 0.18330 | 273 | 3009 |
| 32 | 40.6990 | 2.21512 | 7 | 0.41120 | 252 | 4839 |
| 33 | 40.9030 | 2.20455 | 4 | 0.00000 | 148 | 0 |
| 34 | 41.1653 | 2.19110 | 6 | 0.22630 | 208 | 3523 |
| 35 | 41.7244 | 2.16303 | 7 | 0.17980 | 258 | 2908 |
| 36 | 42.2041 | 2.13954 | 12 | 0.22730 | 444 | 6246 |
| 37 | 43.2388 | 2.09071 | 14 | 0.45860 | 516 | 13010 |
| 38 | 43.6740 | 2.07088 | 9 | 0.26780 | 322 | 5023 |
| 39 | 44.1942 | 2.04770 | 12 | 0.30470 | 412 | 7454 |
| 40 | 44.6363 | 2.02844 | 15 | 0.22970 | 518 | 7908 |
| 41 | 45.9267 | 1.97441 | 4 | 0.15080 | 153 | 1806 |
| 42 | 47.6170 | 1.90819 | 4 | 0.21110 | 144 | 1915 |
| 43 | 47.9580 | 1.89541 | 3 | 0.24780 | 120 | 2775 |
| 44 | 48.2300 | 1.88536 | 4 | 0.00000 | 144 | 0 |
| 45 | 48.3830 | 1.87975 | 3 | 0.36980 | 112 | 2169 |
| 46 | 48.7606 | 1.86608 | 3 | 0.24530 | 109 | 1694 |

Figure 20:
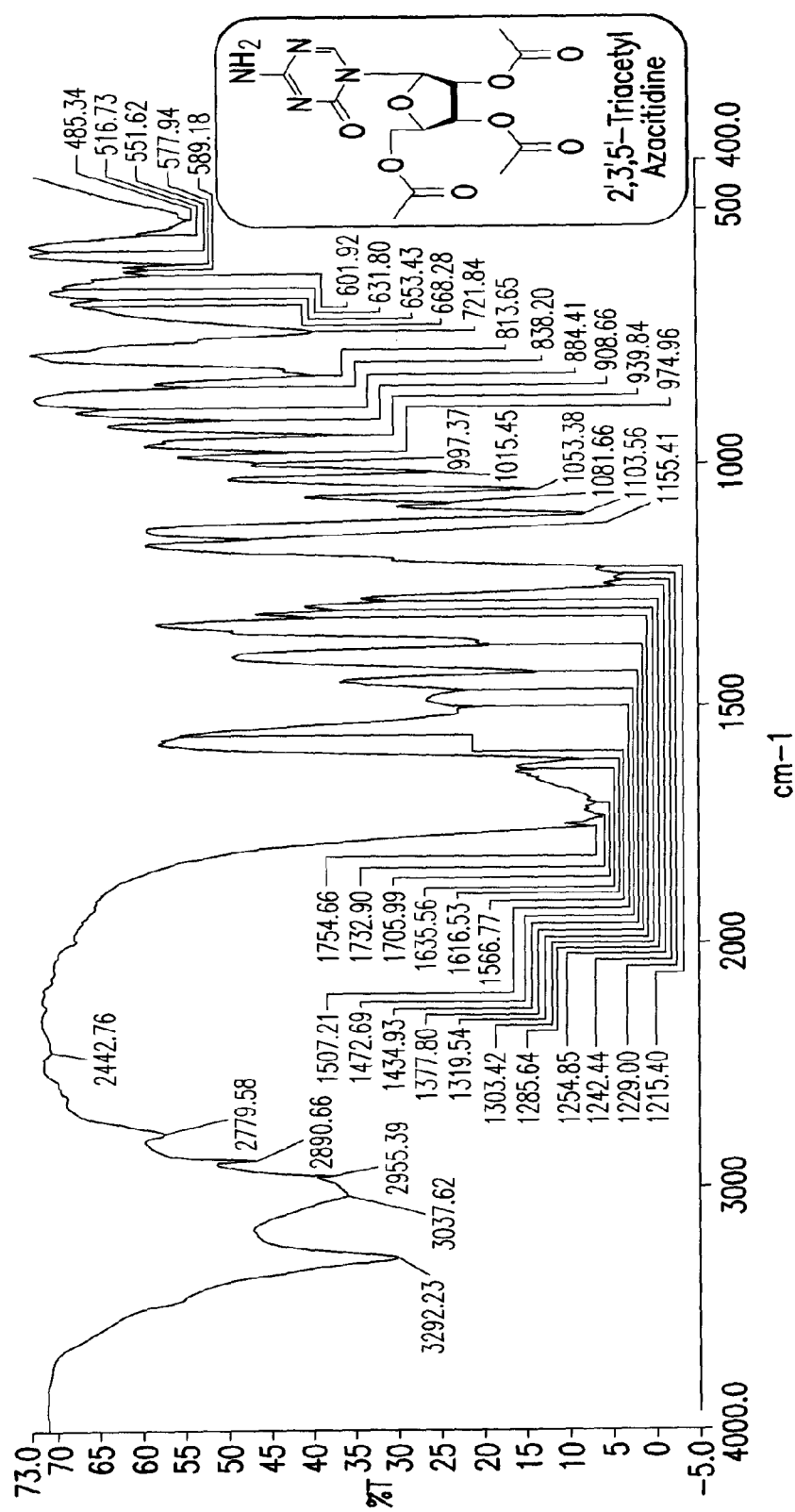
FIG. 20 represents an IR spectrum of 2',3',5'-triacetyl-5-azacytidine.

6. 2',3',5'-Triacetyl-5-Azacytidine $^1$H NMR (DMSO-d$_6$) δ 8.32 (s, 1H), 7.72 (d, 2H, J=9.1 Hz), 5.66 (d, 1H, J=3.2 Hz), 5.53 (m, 1H), 5.41 (t, 1H, J=6.6 Hz), 4.32 (dd, 1H, JJ=2.8, 11.6 Hz), 4.20 (m, 1H), 4.14 (m, 1H), 2.04 (s, 1H), 2.02 (s, 1H), 2.00 (s, 1H).
$^{13}$C NMR (DMSO-d$_6$) δ 170.5, 169.9, 169.7, 166.2, 158.0, 152.9, 90.8, 79.3, 72.9, 70.0, 63.2, 20.8, 20.6, 20.6.
LC-MS ESI: m/z 371.2 (M+H$^+$), 393.1 (M+Na$^+$).
The IR spectrum of 2',3',5'-triacetyl-5-azacytidine is shown in FIG. 20.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed:

1. A process for preparing 5-azacytidine, or a solvate, hydrate, or polymorph thereof, comprising the steps of:

(a) reacting 5-azacytosine with a silylating reagent to yield a silylated 5-azacytosine;

(b) reacting the silylated 5-azacytosine with an acyl protected β-D-ribofuranose in the presence of a metallic Lewis acid; and quenching the reaction with water and at least one neutralizing reagent to yield a protected 5-azacytidine;

(c) reacting the protected 5-azacytidine with a base, selected from the group consisting of alkoxide, ammonia, and tetra-substituted ammonium hydroxide, in an alcohol to yield 5-azacytidine;

(d) contacting the 5-azacytidine from step (c) with an acid in an organic solvent to yield a salt of 5-azacytidine;

(e) contacting the salt of 5-azacytidine from step (d) with a base in an organic solvent to yield 5-azacytidine free base; and (f) re-crystallizing the 5-azacytidine from step (e).

2. The process of claim 1, wherein the silylated 5-azacytosine is a compound of formula (A):

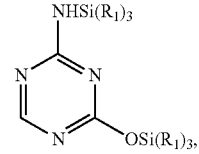

wherein each R$_1$ is independently optionally substituted C$_1$-C$_{10}$ alkyl, optionally substituted C$_3$-C$_{10}$ cycloalkyl, or optionally substituted C$_6$-C$_{10}$ aryl.

3. The process of claim 2, wherein R$_1$ is methyl.

4. The process of claim 1, wherein the silylating reagent used in step (a) is a trimethylsilyl reagent.

5. The process of claim 1, wherein the silylating reagent used in step (a) is hexamethyldisilazane.

6. The process of claim 1, wherein the silylation reaction of step (a) is carried out in the presence of ammonium sulfate.

7. The process of claim 1, wherein the protected β-D-ribofuranose is a compound of formula (B):

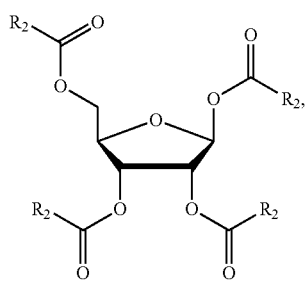

(B)

wherein each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl.

8. The process of claim 1, wherein the protected β-D-ribofuranose is:

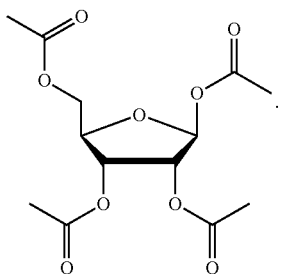

9. The process of claim 1, wherein the metallic Lewis acid is stannic chloride or ferric chloride.

10. The process of claim 1, wherein the metallic Lewis acid is stannic chloride.

11. The process of claim 1, wherein the metallic Lewis acid is ferric chloride.

12. The process of claim 1, wherein the protected 5-azacytidine is a compound of formula (C):

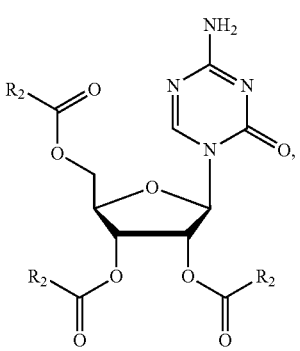

(C)

wherein each $R_2$ is independently hydrogen, optionally substituted $C_1$-$C_{10}$ alkyl, optionally substituted $C_3$-$C_{10}$ cycloalkyl, or optionally substituted $C_6$-$C_{10}$ aryl.

13. The process of claim 1, wherein the protected 5-azacytidine is:

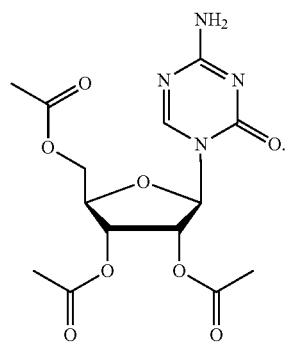

14. The process of claim 1, wherein the coupling reaction of step (b) is carried out in a solvent with low water solubility.

15. The process of claim 14, wherein the solvent with low water solubility is dichloromethane.

16. The process of claim 1, wherein the coupling reaction of step (b) is carried out at a temperature of between about 0° C. and about 5° C.

17. The process of claim 1, wherein the neutralizing reagent in step (b) is a carbonate or bicarbonate salt.

18. The process of claim 1, wherein the neutralizing reagent in step (b) is sodium bicarbonate.

19. The process of claim 1, wherein the reaction of step (b) is quenched at a temperature of less than about 10° C.

20. The process of claim 1, wherein the base in step (c) is an alkoxide.

21. The process of claim 20, wherein the alkoxide is sodium methoxide.

22. The process of claim 1, wherein the alcohol in step (c) is methanol.

23. The process of claim 1, wherein the acid used in step (d) is hydrochloric acid, hydrobromic acid, sulfuric acid, or methanesulfonic acid.

24. The process of claim 1, wherein the acid used in step (d) is hydrochloric acid.

25. The process of claim 1, wherein the organic solvent used in step (d) is an alcohol.

26. The process of claim 1, wherein the organic solvent used in step (d) is methanol.

27. The process of claim 1, wherein the salt of 5-azacytidine formed in step (d) is 5-azacytidine mono-hydrochloride salt.

28. The process of claim 1, wherein the base used in step (e) is an organic base.

29. The process of claim 28, wherein the organic base is triethylamine.

30. The process of claim 1, wherein the organic solvent used in step (e) is an alcohol.

31. The process of claim 1, wherein the organic solvent used in step (e) is methanol.

32. The process of claim 1, wherein step (f) comprises the steps of:
   (1) dissolving 5-azacytidine from step (e) in dimethylsulfoxide at a temperature sufficient to allow the 5-azacytidine to dissolve; and optionally filtering the solution to remove insoluble particles;
   (2) adding an anti-solvent to the solution of step (1); and
   (3) cooling the mixture of step (2) wherein 5-azacytidine re-crystallizes.

33. The process of claim 32, wherein the anti-solvent of step (f)(2) is an alcohol.

34. The process of claim 32, wherein the anti-solvent of step (f)(2) is methanol.

35. The process of claim 32, wherein step (f) further comprises the steps of:
   (4) collecting the re-crystallized 5-azacytidine from step (3) by filtration; and
   (5) drying the 5-azacytidine from step (4) under vacuum.

* * * * *